United States Patent [19]

Miyashiro et al.

[11] Patent Number: 4,642,335

[45] Date of Patent: Feb. 10, 1987

[54] ANTHRACYCLINE COMPOUNDS BOUND TO HYDROPHILIC POLYPEPTIDES

[75] Inventors: Shigeyoshi Miyashiro, Yokohama; Takao Kida, Yokosuka; Tsuyoshi Shiio, Kamakura; Hiroshiro Shibai, Chigasaki, all of Japan

[73] Assignee: Ajinomoto Co., Inc., Tokyo, Japan

[21] Appl. No.: 738,352

[22] Filed: May 28, 1985

[30] Foreign Application Priority Data

May 22, 1984 [JP] Japan .................................. 59-101673

[51] Int. Cl.$^4$ ....................... C07K 17/02; C07K 17/06
[52] U.S. Cl. ...................................... 530/409; 424/85; 424/88; 424/89; 424/92; 514/2; 514/21; 530/345; 530/350; 530/402; 530/405; 530/406; 530/410; 530/825; 530/812
[58] Field of Search ................ 424/85, 88, 89; 260/112 R, 112 B; 530/825, 812, 350, 345, 409, 410, 402; 514/2.21

[56] References Cited

U.S. PATENT DOCUMENTS 4,093,607  6/1978  Sela et al. ......................... 260/112 B
4,534,971  8/1985  Fisher ............................... 260/112 R

OTHER PUBLICATIONS

Cancer Research 35, 1175–1181 (1975), Hurwitz et al.
J. Antibiotics, 36 (9), 1136–1143 (1983), Miyashiro et al.
J. Antibiotics, 37 (1), 20–26 (Jan., 1984), Miyashiro et al.

Primary Examiner—Howard E. Schain
Attorney, Agent, or Firm—Oblon, Fisher, Spivak, McClelland, & Maier

[57] ABSTRACT

This invention relates to an antitumor composition of anthracycline compounds bonded to hydrophilic polypeptides having a molecular weight between 10,000 and 15,000.

17 Claims, 66 Drawing Figures

ANTHRACYCLINE COMPOUNDS BOUND TO HYDROPHILIC POLYPEPTIDES

DETAILED DESCRIPTION OF THE INVENTION

1. Technical Field

This invention relates to novel anthracycline compounds and anticancer agents containing the same as active ingredient.

2. Prior Arts

Antitumor substances of anthracycline family are among the various types of anticancer agents presently available. These are glycosides whose aglycones are represented by the following general formula:

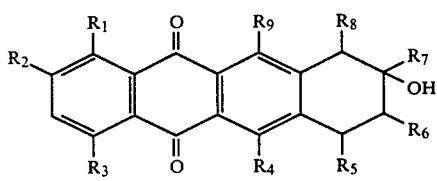

wherein $R_1$ is H or —OH, $R_2$ is —OH or —OCH$_3$, or $R_1$ and $R_2$ may unite together to form a radical of

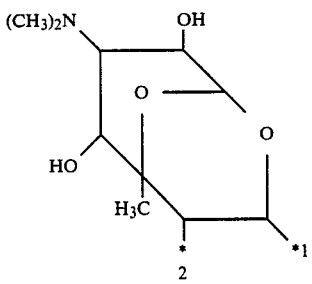

$R_3$ is —OH or —OCH$_3$; $R_4$ is H or —OH; $R_5$ is H or —OH; $R_6$ is H or —OCH$_3$; $R_7$ is —COCH$_2$OH, —CH(OH)CH$_2$OH, —COCH$_3$, —CH(OH)CH$_3$, —CH$_2$CH$_3$, —CH$_2$OCH$_3$, —CH$_2$COCH$_3$, —CH$_3$ or —CH(CH$_3$)$_2$; $R_8$ is H, —OH, —COOCH$_3$ or =O; and $R_9$ is H or —OH.

Typical examples of these anthracycline antitumor substances are daunomycin represented by the following formula:

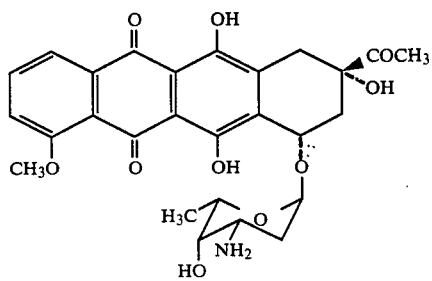

adriamycin represented by the following formula:

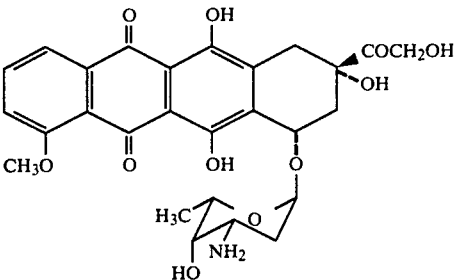

and aclacinomycin A represented by the following formula:

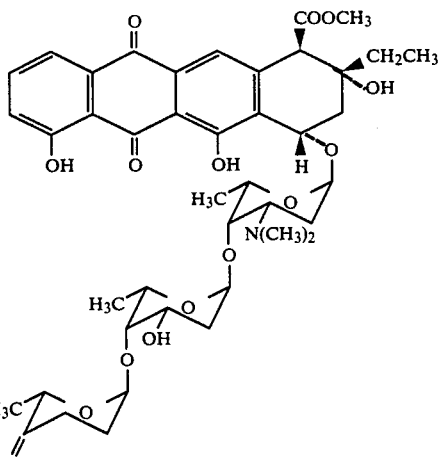

[refer to "The Merck Index" (10th edition), 2815, 3425 and 109].

Besides these, γ-rhodomycin Y (E. Biedermann, et al., Pharmazie, 782, 1972) and cosmomycin A (H. Brockmann, et al., Tetrahedron Letters, 831, 1975), represented by the following formulas respectively, are also known.

(γ-Rhodomycin Y)

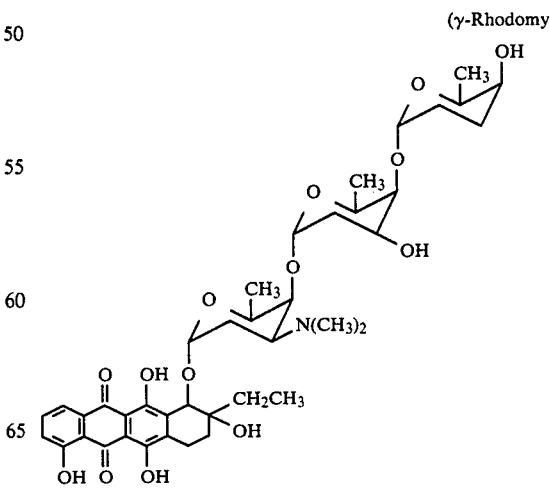

-continued

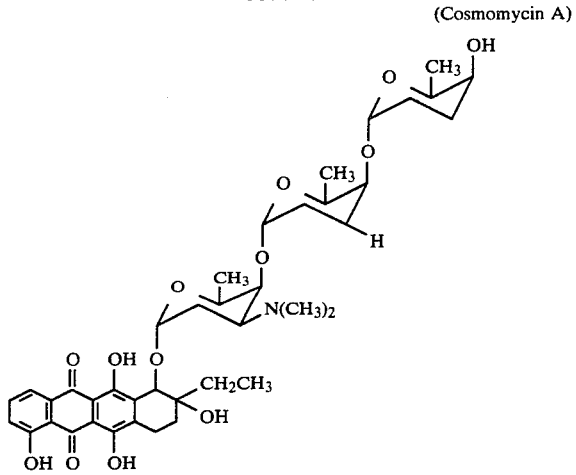
(Cosmomycin A)

However, the carcinocidal activity of these substances is not absolutely satisfactory like other types of anti-cancer agents sofar known, and there is a strong need for novel compounds having better anticancer activity.

OBJECT OF THE INVENTION

The object of this invention is to provide new anthracycline compounds with higher carcinocidal activity and broader carcinocidal spectrum accompanied by less toxicity, and to provide anticancer agents containing the same as active ingredient.

DETAILED DESCRIPTION OF THE PREFERRED EMBODIMENTS

The first item of this invention relates to anthracycline compounds composed of an antitumor substance of anthracycline family and a hydrophilic polypeptide rich in hydrophobic amino acids and having a molecular weight in the range from 10,000 to 15,000, said antitumor substance and said polypeptide being combined through hydrogen bond and/or a hydrophobic bond.

The second item of this invention relates to anticancer agents containing, as active ingredient, an anthracycline compound specified in the first item.

As examples of the hydrophilic polypeptides, which are one constituent of the compounds of this invention, may be mentioned the protein moiety of high-molecular polypeptide type anticancer agents, and a water-soluble basic polypeptide, AN-3, which the present inventors have isolated from a broth culture of Streptomyces albulus [J. Antibiotics, 36(9), p1136–1143 (1983)].

The high-molecular polypeptide anticancer agents referred to above include neocarzinostatin (hereinafter abbreviated as "NCS") [J. Antibiotics, serA 18(2), p68 (1965)], macromomycin [J. Antibiotics, 21, p44 (1968)], Sporamycin [J. Antibiotics, 29, p1249 (1976)], auromomycin [J. Antibiotics, 32, p330 (1979)], as well as AN-7A, AN-7B and AN-7D which the present inventors have isolated from a culture of Streptomyces griseoincarnatus AJ9424 (FERM-P6012) [Japanese Patent Application No. 89316 (1981); and J. Antibiotics, 37, p20 (1984)]. The corresponding protein moiety (hereinafter abbreviated as "apoprotein") can be obtained from each of the above-mentioned anticancer agents by decomposition under mild conditions. For example, suspending powder of the anticancer agent in a nonpolar organic solvent (e.g., lower alkanols) and stirring the resulting suspension gives a soluble fraction (apoprotein) and an insoluble fraction (non-protein moiety). One can thus easily separate the corresponding apoprotein from the non-protein moiety.

The compounds of this invention may be prepared by combining a hydrophilic polypeptide thus obtained with an antitumor substance of anthracycline family through hydrogen bond and/or a hydrophobic bond according, for example, to the method described below.

A solution of hydrophilic polypeptide in water is mixed with a solution of antitumor substance in water or in a water-miscible organic solvent (for example, water or methanol) in such a proportion that the two components will be present at an intended molar ratio, and the mixture is freeze-dried (after removal of organic solvent, if used). The dried powder is dissolved in water, insoluble matters, if present, are removed by centrifugation or filtration, and the water-soluble fraction thus obtained is purified by known techniques (gel filtration, salting out, dialysis, ion-exchange chromatography, etc.), followed by freeze-drying.

The compounds of this invention, in which a hydrophilic polypeptide and an anthracycline antitumor substance are combined through hydrogen bond and/or a hydrophobic bond, behave as a single polymer in water. But these bonds are broken to liberate the two components if the compounds are treated under certain conditions, such as treatment with 8M solution of urea (cleavage of hydrogen bond), treatment with 1% solution of sodium dodecylsulfate (hereinafter abbreviated as "SDS"), and extraction with methanol or ethyl acetate (cleavage of hydrophobic bond).

The preferable molar ratio of the hydrophilic polypeptide to the anthracycline antitumor substance in the compounds of this invention is in the range from 0.25 to 10.

This ratio can be determined by the measurement of molecular weight (gel filtration method) and from the molar extinction coefficient of the absorption bands characteristic to the anthracycline antitumor substance contained.

The compounds of this invention thus prepared show higher carcinocidal activity at less dose than the antitumor substances of anthracycline family, and also have antibacterial activity.

Examples of preparative methods for the hydrophilic polypeptides (one of the constituents of the compounds of this invention) are described below.

Preparative Example 1

Sixty milliliters of NCS (product of Yamanouchi Pharmaceutical Co., Ltd.) was subjected to gel filtration by using Bio-Gel P30, and a fraction having a molecular weight of 13,000 and showing antibacterial activity against Micrococcus luteus was collected and freeze-dried, giving 48 mg of desalted NCS powder. Five milliliters of cold methanol was added to this powder, and the mixture was stirred in the dark for four hours under ice cooling and then centrifuged at 0° C. (10,000 rpm, 10 minutes), affording 40 mg of methanol-insoluble fraction (NCS-apoprotein) and 0.2 mg of soluble fraction (nonprotein moiety).

Preparative Example 2

Powder of AN-7D (1 gram) was treated in the same way as in Preparative Example 1, giving 800 mg of AN-7D-apoprotein and 8 mg of nonprotein moiety.

The following lists the physical and chemical properties of the polypeptides used in Examples describe later.

NCS-apoprotein (1) Appearance: White powder
(2) Molecular weight: 12,400 (electrophoresis on SDS polyacrylamide gel)
(3) N-terminated amino acid: Alanine (dansyl method)
(4) Isoelectric point: pH 3.2
(5) Melting point: Shows no definite melting point; chars with decomposition at above 230° C.
(6) Elemental analysis: 14.48% N, 48.16% C, 6.43%H, 1.98% S, 28.99% O
(7) Ninhydrin and biuret reactions: Positive response to both.
(8) Aanthrone and Blix reactions: Negative response to both (no hexose nor hexosamine included).
(9) Solubility: Soluble in water; insoluble in methanol, ethanol, acetone, butanol and propanol.
(10) UV absorption spectrum: As shown in FIG. 1 [optical density (O.D) plotted against wavelength (nm)].
(11) IR absorption spectrum: As shown in FIG. 2 [KBr disk; transmittance (%) plotted against wave number $(cm^{-1})$].

AN-7D-apoprotein (1) Appearance: White powder
(2) Molecular weight: 12,400 (electrophoresis on SDS polyacrylamide gel)
(3) N-terminated amino acid: Alanine (dansyl method)
(4) Isoelectric point: pH 3.2
(5) Melting point: Shows no definite melting point; chars with decomposition at above 230° C.
(6) Elemental anslysis: 14.39% N, 48.19% C, 6.56% H, 2.00% S, 28.86% O
(7) Ninhydrin and biuret reactions: Positive response to both.
(8) Aanthrone and Blix reactions: Negative response to both (no hexose nor hexosamine included).
(9) Solubility: Soluble in water; insoluble in methanol, ethanol, acetone, butanol and propanol.
(10) UV absorption spectrum: As shown in FIG. 3 [optical density (O.D) plotted against wavelength (nm)].
(11) IR absorption spectrum: As shown in FIG. 4 [KBr disk; transmittance (%) plotted against wave number $(cm^{-1})$].

AN-3

(1) Appearance: White powder
(2) Molecular weight: 12,000 (gel filtration with Bio-Gel P-30) 12,500 (electrophoresis on SDS polyacrylamide gel)
(3) N-terminated amino acid: Alanine (dansyl method)
(4) Isoelectric point: pH 7.6 (approximately)
(5) Melting point: Shows no definite melting point; chars with decomposition at above 230° C.
(6) Elemental anslysis: 9.91% N, 36.66% C, 5.56% H
(7) Ninhydrin and biuret reactions: Positive response to both.
(8) Aanthrone and Blix reactions: Negative response to both.
(9) Solubility: Soluble in water; insoluble in organic solvents such as ethanol, butanol and acetone.
(10) UV absorption spectrum: As shown in FIG. 5 [extinction coefficient ($E_1 \, _{cm}^{1\%}$) plotted against wavelength (nm).
(11) IR absorption spectrum: As shown in FIG. 6 [KBr disk; transmittance (%) plotted against wave number $(cm^{-1})$].

EXAMPLES

The following Examples further illustrate this invention but are not intended to limit its scope.

EXAMPLE 1

AN-7D-apoprotein (39 mg, $3 \times 10^{-6}$ mole) obtained in Preparative Example 2 was dissolved in 4 ml water to make its aqueous solution of 9.75 mg/ml concentration. Separately, adriamycin (1.63 mg, $3 \times 10^{-6}$ mole; product of Kyowa Hakko Kogyo, Co., Ltd.) was dissolved in 4 ml methanol. The two solutions were mixed at room temperature, methanol was distilled off from the mixture by using a rotary evaporator, and the resulting liquor was freeze-dried, giving 41 mg of powder. This powder was dissolved in 4 ml water, the aqueous solution was centrifuged, the supernatant was subjected to gel filtration by using Bio-Gel P-30, and a fraction corresponding to a molecular weight of 13,000 was collected. Freeze drying of this fraction gave 24.4 mg of substance HB-6(A) in which AN-7D-apoprotein and adriamycin are bound together through hydrogen bond and/or hydrophobic bond at a molar ratio of 1:1.

Similarly, substances HB-6(B), HB-6(C) and HB-6(D) were obtained in which AN-7D-apoprotein is combined with adriamycin at a molar ratio of 1:10, 2:1 and 4:1, respectively.

The physical and chemical properties of these substances are shown below.
(1) Appearance: Red powder (for all)
(2) Molecular weight (gel filtration):
  13,000 [HB-6(A)]
  13,000 [HB-6(B)]
  26,000 [HB-6(C)]
  52,000 [HB-6(D)]
(3) N-terminated amino acid: Alanine (for all)
(4) Isoelectric point: pH 3.2 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 7 [optical density (O.D) plotted against wavelength (nm)].
(9) IR absorption spectrum: As shown in FIG. 8 [KBr disk; transmittance (%) plotted against wave number $(cm^{-1})$].

These HB-6 substances were tested for their antitumor activity in terms of mouse L1210 leukemia. L1210 leukemia cells ($1 \times 10^5$) were abdominally injected to each mouse, and the test sample was administered once a day for consecutive five days, with the first administration being started 24 hours after injection of the tumor cells. The result is summarized in Table 1, in which the antitumor activity of each drug is expressed as life prolongation rate, taking the survival day for the control group as 100%.

TABLE 1

| Drug | Dose (mg/Kg) | Life Prolongation Rate (%) |
|---|---|---|
| HB-6(A) | 2 | 280 |
| HB-6(B) | 2 | 295 |
| HB-6(C) | 2 | 240 |

TABLE 1-continued

| Drug | Dose (mg/Kg) | Life Prolongation Rate (%) |
| --- | --- | --- |
| HB-6(D) | 2 | 200 |
| Adriamycin | 2 | 150 |
| AN-7D-apoprotein | 2 | 100 |

EXAMPLE 2

AN-7D-apoprotein (39 mg, $3 \times 10^{-6}$ mole) obtained in Preparative Example 2 was dissolved in 4 ml water to make its aqueous solution of 9.75 mg/ml concentration. Separately, adriamycin (1.63 mg, $3 \times 10^{-6}$ mole; product of Kyowa Hakko Kogyo, Co., Ltd.) was dissolved in 4 ml water. The two solutions were mixed at room temperature, and the mixture was freeze-dried, giving 41 mg of powder. This powder was dissolved in 4 ml water, the aqueous solution was centrifuged, the supernatant was subjected to gel filtration by using Bio-Gel P-30, and a fraction corresponding to a molecular weight of 13,000 was collected. Freeze drying of this fraction gave 24.4 mg of substance HBW-6(A) in which AN-7D-apoprotein and adriamycin are bound together through hydrogen bond and/or hydrophobic bond at a molar ratio of 1:1.

Similarly, substance HBW-6(B), in which AN-7D-apoprotein is combined with adriamycin at a molar ratio of 1:5, was obtained.

The physical and chemical properties of these substances are shown below.

(1) Appearance: Red powder
(2) Molecular weight (gel filtration):
    13,000 [HBW-6(A)]
    13,000 [HBW-6(B)]
(3) N-terminated amino acid: Alanine
(4) Isoelectric point: pH 3.2
(5) Melting point: Show no definite melting point, both charring with decomposition at above 230° C.
(6) Ninhydrin and biuret reactions: Positive response to both
(7) Solubility: Soluble in water; insoluble in methanol, ethanol, butanol and propanol (for all).
(8) UV absorption spectrum: As shown in FIG. 9 [optical density (O.D) plotted against wavelength (nm)].
(9) IR absorption spectrum: As shown in FIG. 10 [KBr disk; transmittance (%) plotted against wave number ($cm^{-1}$)].

These HBW-6 substances were tested for their antitumor activity in terms of mouse L1210 leukemia. L1210 leukemia cells ($1 \times 10^5$) were abdominally injected to each mouse, and the test sample was administered once a day for consecutive five days, with the first administration being started 24 hours after injection of the tumor cells. The result is summarized in Table 2, in which the antitumor activity of each drug is expressed as life prolongation rate, taking the survival day for the control group as 100%.

TABLE 2

| Drug | Dose (mg/Kg) | Life Prolongation Rate (%) |
| --- | --- | --- |
| HBW-6(A) | 1 | 295 |
| HBW-6(B) | 1 | 298 |
| Adriamycin | 2 | 150 |
| AN-7D-apoprotein | 2 | 100 |

EXAMPLE 3

NCS-apoprotein, obtained in Preparative Example 1, and daunomycin (product of Meiji Seika Co., Ltd.) were bound together by the same way as in Example 1 to give substances HB-10(A), (B), (C) and (D), in which the two constituents are combined at molar ratios of 1:1, 1:10, 2:1 and 4:1, respectively. The phsyical and chemical properties of these substances are shown below, and their antitumor activity against mouse L1210 cells is summarized in Table 3.

(1) Appearance: Red powder (for all)
(2) Molecular weight (gel filtration):
    13,000 [HB-10(A)]
    13,000 [HB-20(B)]
    26,000 [HB-10(C)]
    52,000 [HB-10(D)]
(3) N-terminated amino acid: Alanine (for all)
(4) Isoelectric point: pH 3.2 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 11 [optical density (O.D) plotted against wavelength (nm)].
(9) IR absorption spectrum: As shown in FIG. 12 [KBr disk; transmittance (%) plotted against wave number ($cm^{-1}$)].

TABLE 3

| Drug | Dose (mg/Kg) | Life Prolongation Rate (%) |
| --- | --- | --- |
| HB-10(A) | 2 | 250 |
| HB-10(B) | 2 | 265 |
| HB-10(C) | 2 | 230 |
| HB-10(D) | 2 | 200 |
| Daunomycin | 2 | 145 |
| NCS-apoprotein | 2 | 101 |

EXAMPLE 4

NCS-apoprotein and daunomycin were bound together through hydrogen bond and/or hydrophobic bond by the same way as in Example 2 to give substances HBW-10(A) and HBW-10(B).

The physical and chemical properties of these substances are shown below, and their anticancer activity against mouse L1210 cells is summarized in Table 4.

Molar ratio of NCS-apoprotein to daunomycin: 1:1 for (A), and 1:5 for (B)
(1) Appearance: Red powder (for all)
(2) Molecular weight (gel filtration):
    13,000 [HBW-10(A)]
    13,000 [HBW-10(B)]
(3) N-terminated amino acid: Alanine (for all)
(4) Isoelectric point: pH 3.2 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 13 [optical density (O.D) plotted against wavelength (nm)].
(9) IR absorption spectrum: As shown in FIG. 14 [KBr disk; transmittance (%) plotted against wave number ($cm^{-1}$)].

TABLE 4

| Drug | Dose (mg/Kg) | Life Prolongation Rate (%) |
|---|---|---|
| HBW-10(A) | 1 | 260 |
| HBW-10(B) | 1 | 270 |
| NCS-apoprotein | 2 | 101 |
| Daunomycin | 2 | 145 |

EXAMPLE 5

AN-7D-apoprotein and aclacinomycin A (product of Yamanouchi Pharmaceutical Co., Ltd.) were bound together through hydrogen bond and/or hydrophobic bond by the same way as in Example 1 to give substances HB-12(A), (B), (C) and (D).

The physical and chemical properties of these HB-12 substances are shown below, and their anticancer activity against mouse L1210 cells is summarized in Table 5.

Molar ratio of AN-7D-apoprotein to aclacinomycin A: 1:1 for (A), 1:10 for (B), 2:1 for (C), and 4:1 for (D)

(1) Appearance: Yellow powder (for all)
(2) Molecular weight (gel filtration):
   13,000 [HB-12(A)]
   13,000 [HB-12(B)]
   26,000 [HB-12(C)]
   52,000 [HB-12(D)]
(3) N-terminated amino acid: Alanine (for all)
(4) Isoelectric point: pH 3.2 (for all
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 15 [optical density (O.D) plotted against wavelength (nm)].
(9) IR absorption spectrum: As shown in FIG. 16 [KBr disk; transmittance (%) plotted against wave number (cm$^{-1}$)].

TABLE 5

| Drug | Dose (mg/Kg) | Life Prolongation Rate (%) |
|---|---|---|
| HB-12(A) | 2 | 210 |
| HB-12(B) | 2 | 250 |
| HB-12(C) | 2 | 170 |
| HB-12(D) | 2 | 155 |
| AN-7D-apoprotein | 2 | 101 |
| Aclacinomycin A | 2 | 135 |

EXAMPLE 6

AN-7D-apoprotein and aclacinomycin A (product of Yamanouchi Pharmaceutical Co., Ltd.) were bound together through hydrogen bond and/or hydrophobic bond by the same way as in Example 2 to give substances HBW-12(A) and (B).

The physical and chemical properties of these HBW-12 substances are shown below, and their anticancer activity against mouse L1210 cells is summarized in Table 6.

Molar ratio of AN-7D-apoprotein to aclacinomycin A: 1:1 for (A), and 1:5 for (B)

(1) Appearance: Yellow powder (for all)
(2) Molecular weight (gel filtration):
   13,000 [HBW-12(A)]
   13,000 [HBW-12(B)]
(3) N-terminated amino acid: Alanine (for all)
(4) Isoelectric point: pH 3.2 (for all
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 17 [optical density (O.D) plotted against wavelength (nm)].
(9) IR absorption spectrum: As shown in FIG. 18 [KBr disk; transmittance (%) plotted against wave number (cm$^{-1}$)].

TABLE 6

| Drug | Dose (mg/Kg) | Life Prolongation Rate (%) |
|---|---|---|
| HBW-12(A) | 1 | 185 |
| HBW-12(B) | 1 | 190 |
| AN-7D-apoprotein | 2 | 100 |
| Aclacinomycin A | 2 | 135 |

EXAMPLE 7

AN-3 and adriamycin were bound together through hydrogen bond and/or hydrophobic bond by the same way as in Example 1 to give substances HB-13(A), (B), (C) and (D).

The physical and chemical properties of these HB-13 substances are shown below, and their anticancer activity against mouse L1210 cells is summarized in Table 7.

Molar ratio of AN-3 to adriamycin: 1:1 for (A), 1:10 for (B), 2:1 for (C), and 4:1 for (D)

(1) Appearance: Red powder (for all)
(2) Molecular weight (gel filtration):
   13,000 [HB-13(A)]
   13,000 [HB-13(B)]
   26,000 [HB-13(C)]
   52,000 HB-13(D)]
(3) N-terminated amino acid: Alanine (for all)
(4) Isoelectric point: pH 7.6 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 19 [optical density (O.D) plotted against wavelength (nm)].
(9) IR absorption spectrum: As shown in FIG. 20 [KBr disk; transmittance (%) plotted against wave number (cm$^{-1}$)].

TABLE 7

| Drug | Dose (mg/Kg) | Life Prolongation Rate (%) |
|---|---|---|
| HB-13(A) | 2 | 290 |
| HB-13(B) | 2 | 310 |
| HB-13(C) | 2 | 230 |
| HB-13(D) | 2 | 220 |
| AN-3 | 2 | <100 |
| Adriamycin | 2 | 150 |

EXAMPLE 8

AN-3 and adriamycin were bound together through hydrogen bond and/or hydrophobic bond by the same way as in Example 2 to give substances HBW-13(A) and (B).

The physical and chemical properties of these HBW-13 substances are shown below, and their anticancer activity against mouse L1210 cells is summarized in Table 8.

Molar ratio of AN-3 to adriamycin: 1:1 for (A), and 1:5 for (B)
(1) Appearance: Red powder (for all)
(2) Molecular weight (gel filtration):
    13,000 [HBW-13(A)]
    13,000 [HBW-13(B)]
(3) N-terminated amino acid: Alanine (for all)
(4) Isoelectric point: pH 7.6 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 21 [optical density (O.D) plotted against wavelength (nm)].
(9) IR absorption spectrum: As shown in FIG. 22 [KBr disk; transmittance (%) plotted against wave number $(cm^{-1})$].

TABLE 8

| Drug | Dose (mg/Kg) | Life Prolongation Rate (%) |
| --- | --- | --- |
| HBW-13(A) | 1 | 293 |
| HBW-13(B) | 1 | 320 |
| AN-3 | 2 | <100 |
| Adriamycin | 2 | 150 |

EXAMPLE 9

AN-3 and daunomycin were bound together through hydrogen bond and/or hydrophobic bond by the same way as in Example 1 to give substances HB-14(A), (B), (C) and (D).

The physical and chemical properties of these HB-14 substances are shown below, and their anticancer activity against mouse L1210 cells is summarized in Table 9.

Molar ratio of AN-3 to daunomycin: 1:1 for (A), 1:10 for (B), 2:1 for (C), and 4:1 for (D)
(1) Appearance: Red powder (for all)
(2) Molecular weight (gel filtration):
    13,000 [HB-14(A)]
    13,000 [HB-14(B)]
    26,000 [HB-14(C)]
    52,000 [HB-14(D)]
(3) N-terminated amino acid: Alanine (for all)
(4) Isoelectric point: pH 7.6 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 23 [optical density (O.D) plotted against wavelength (nm)].
(9) IR absorption spectrum: As shown in FIG. 24 [KBr disk; transmittance (%) plotted against wave number $(cm^{-1})$].

TABLE 9

| Drug | Dose (mg/Kg) | Life Prolongation Rate (%) |
| --- | --- | --- |
| HB-14(A) | 2 | 210 |
| HB-14(B) | 2 | 280 |
| HB-14(C) | 2 | 200 |
| HB-14(D) | 2 | 190 |
| AN-3 | 2 | <100 |
| Daunomycin | 2 | 145 |

EXAMPLE 10

AN-3 and daunomycin were bound together through hydrogen bond and/or hydrophobic bond by the same way as in Example 2 to give substances HBW-14(A) and (B).

The physical and chemical properties of these HBW-14 substances are shown below, and their anticancer activity against mouse L1210 cells is summarized in Table 10.

Molar ratio of AN-3 to daunomycin: 1:1 for (A), and 1:5 for (B)
(1) Appearance: Red powder (for all)
(2) Molecular weight (gel filtration):
    13,000 [HBW-14(A)]
    13,000 [HBW-14(B)]
(3) N-terminated amino acid: Alanine (for all)
(4) Isoelectric point: pH 7.6 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 25 [optical density (O.D) plotted against wavelength (nm)].
(9) IR absorption spectrum: As shown in FIG. 26 [KBr disk; transmittance (%) plotted against wave number $(cm^{-1})$].

TABLE 10

| Drug | Dose (mg/Kg) | Life Prolongation Rate (%) |
| --- | --- | --- |
| HBW-14(A) | 1 | 220 |
| HBW-14(B) | 1 | 285 |
| AN-3 | 2 | <100 |
| Daunomycin | 2 | 145 |

EXAMPLE 11

AN-3 and aclacinomycin A were bound together through hydrogen bond and/or hydrophobic bond by the same way as in Example 1 to give substances HB-15(A), (B), (C) and (D).

The physical and chemical properties of these HB-15 substances are shown below, and their anticancer activity against mouse L1210 cells is summarized in Table 11.

Molar ratio of AN-3 to aclacinomycin A: 1:1 for (A), 1:10 for (B), 2:1 for (C), and 4:1 for (D)
(1) Appearance: Yellow powder (for all)
(2) Molecular weight (gel filtration):
    13,000 [HB-15(A)]
    13,000 [HB-15(B)]
    26,000 [HB-15(C)]
    52,000 [HB-15(D)]
(3) N-terminated amino acid: Alanine (for all)
(4) Isoelectric point: pH 7.6 (for all)
(5) Melting point: Show no definite melting point, all charring with decomposition at above 230° C.
(6) Ninhydrin and biuret reactions: Positive response to both (for all).

(7) Solubility: Soluble in water; insoluble in methanol, ethanol, butanol and propanol (for all).
(8) UV absorption spectrum: As shown in FIG. 27 [optical density (O.D) plotted against wavelength (nm)].
(9) IR absorption spectrum: As shown in FIG. 28 [KBr disk; transmittance (%) plotted against wave number (cm$^{-1}$)].

TABLE 11

| Drug | Dose (mg/Kg) | Life Prolongation Rate (%) |
|---|---|---|
| HB-15(A) | 2 | 240 |
| HB-15(B) | 2 | 350 |
| HB-15(C) | 2 | 160 |
| HB-15(D) | 2 | 145 |
| AN-3 | 2 | 100 |
| Aclacinomycin A | 2 | 135 |

EXAMPLE 12

AN-3 and aclacinomycin A were bound together through hydrogen bond and/or hydrophobic bond by the same way as in Example 2 to give substances HBW-15(A) and (B).

The physical and chemical properties of these HBW-15 substances are shown below, and their anticancer activity against mouse L1210 cells is summarized in Table 12.

Molar ratio of AN-3 to aclacinomycin A: 1:1 for (A), and 1:5 for (B)
(1) Appearance: Yellow powder (for all)
(2) Molecular weight (gel filtration):
   13,000 [HBW-15(A)]
   13,000 [HBW-15(B)]
(3) N-terminated amino acid: Alanine (for all)
(4) Isoelectric point: pH 7.6 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 29 [optical density (O.D) plotted against wavelength (nm)].
(9) IR absorption spectrum: As shown in FIG. 30 [KBr disk; transmittance (%) plotted against wave number (cm$^{-1}$)].

TABLE 12

| Drug | Dose (mg/Kg) | Life Prolongation Rate (%) |
|---|---|---|
| HBW-15(A) | 1 | 245 |
| HBW-15(B) | 1 | 360 |
| AN-3 | 2 | 100 |
| Aclacinomycin A | 2 | 135 |

EXAMPLE 13

NCS-apoprotein, obtained in Preparative Example 1, and adriamycin (product of Kyowa Hakko Kogyo Co., Ltd.) were bound together through hydrogen bond and/or hydrophobic bond by the same way as in Example 1 to give substances HB-20(A) and (B), in which the two constituents are combined at molar ratios of 1:1 and 1:5 respectively.

The physical and chemical properties of these HB-20 substances are shown below, and their anticancer activity against mouse L1210 cells is summarized in Table 13.
(1) Appearance: Red powder (for all)
(2) Molecular weight (gel filtration):
   13,000 [HB-20(A)]
   13,000 [HB-20(B)]
(3) N-terminated amino acid: Alanine (for all)
(4) Isoelectric point: pH 3.2 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 31 [optical density (O.D) plotted against wavelength (nm)].
(9) IR absorption spectrum: As shown in FIG. 32 [KBr disk; transmittance (%) plotted against wave number (cm$^{-1}$)].

TABLE 13

| Drug | Dose (mg/Kg) | Life Prolongation Rate (%) |
|---|---|---|
| HB-20(A) | 2 | 200 |
| HB-20(B) | 2 | 205 |
| NCS-apoprotein | 2 | 101 |
| Adriamycin | 2 | 150 |

EXAMPLE 14

NCS-apoprotein, obtained in Preparative Example 1, and adriamycin (product of Kyowa Hakko Kogyo Co., Ltd.) were bound together through hydrogen bond and/or hydrophobic bond by the same way as in Example 2 to give substances HBW-20(A) and (B), in which the two constituents are combined at molar ratios of 1:1 and 1:5 respectively.

The physical and chemical properties of these HBW-20 substances are shown below, and their anticancer activity against mouse L1210 cells is summarized in Table 14.
(1) Appearance: Red powder (for all)
(2) Molecular weight (gel filtration):
   13,000 [HBW-20(A)]
   13,000 [HBW-20(B)]
(3) N-terminated amino acid: Alanine (for all)
(4) Isoelectric point: pH 3.2 (for all)
(5) melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 33 [optical density (O.D) plotted against wavelength (nm)].
(9) IR absorption spectrum: As shown in FIG. 34 [KBr disk; transmittance (%) plotted against wave number (cm$^{-1}$)].

TABLE 14

| Drug | Dose (mg/Kg) | Life Prolongation Rate (%) |
|---|---|---|
| HBW-20(A) | 1 | 268 |
| HBW-20(B) | 1 | 245 |
| NCS-apoprotein | 2 | 101 |
| Adriamycin | 2 | 150 |

EXAMPLE 15

An-7D-apoprotein and daunomycin were bound together through hydrogen bond and/or hydroprobic bond by the same way as in Example 1 to give substances HB-1(A) and (B).

The physical and chemical properties of these HB-1 substances are shown below, and their anticancer activity against mouse L1210 cells is summarized in Table 15.

Molar ratio of AN-7D-apoprotein to daunomycin: 1:1 for (A), and 1:5 for (B)
(1) Appearance: Read powder (for all)
(2) Molecular weight (gel filtration):
  13,000 [HB-1(A)]
  13,000 [HB-1(B)]
(3) N-terminated amino acid: Alanine (for all)
(4) Isoelectric point: pH 3.2 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 35 [optical density (O.D) plotted against wavelength (nm)].
(9) IR absorption spectrum: As shown in FIG. 36 [KBr disk; transmittance (%) plotted against wave number $(cm^{-1})$.]

TABLE 15

| Drug | Dose (mg/Kg) | Life Prolongation Rate (%) |
|---|---|---|
| HB-1(A) | 2 | 195 |
| HB-1(B) | 2 | 197 |
| AN-7D-apoprotein | 2 | 100 |
| Daunomycin | 2 | 145 |

EXAMPLE 16

AN-7D-apoprotein and daunomycin were bound together through hydrogen bond and/or hydrophobic bond by the same way as in Example 2 to give substances HBW-1(A) and (B).

The physical and chemical properties of these HBW-1 substances are shown below, and their anticancer activity against mouse L1210 cells is summarized in Table 16.

Molar ratio of AN-7D-apoprotein to daunomycin: 1:1 for (A), and 1:5 for (B)
(1) Appearance: Red powder (for all)
(2) Molecular weight (gel filtrateion):
  13,000 [HBW-1(A)]
  13,000 [HBW-1(B)]
(3) n-terminated amino acid: Alanine (for all)
(4) Isoelectric point: pH 3.2 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 37 [optical density (O.D) plotted against wavelength (nm)].
(9) IR absorption spectrum: As shown in FIG. 38 [KBr disk; transmittance (%) plotted against wave number $(cm^{-1})$].

TABLE 16

| Drug | Dose (mg/Kg) | Life Prolongation Rate (%) |
|---|---|---|
| HBW-1(A) | 1 | 155 |
| HBW-1(B) | 1 | 157 |
| AN-7D-apoprotein | 2 | 100 |

TABLE 16-continued

| Drug | Dose (mg/Kg) | Life Prolongation Rate (%) |
|---|---|---|
| Daunomycin | 2 | 145 |

EXAMPLE 17

AN-7D-apoprotein and γ-rhodomycin Y were bound together through hydrogen bond and/or hydrophobic bond by the same way as in Example 1 to give substances HB-2(A) and (B).

The physical and chemical properties of these HB-2 substances are shown below, and their anticancer activity against mouse L1210 cells is summarized in Table 17.

Molar ratio of AN-7D-apoprotein to γ-rhodomycin Y: 1:1 for (A), and 1:5 for (B)
(1) Appearance: Red powder (for all)
(2) Molecular weight (gel filtration):
  13,000 [HB-2(A)]
  13,000 [HB-2(B)]
(3) N-terminated amino acid: Alanine (for all)
(4) Isoelectric point: pH 3.2 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 39 [optical density (O.D) plotted against wavelength (nm)].
(9) IR absorption spectrum: As shown in FIG. 40 [KBr disk; transmittance (%) plotted against wave number $(cm^{-1})$].

TABLE 17

| Drug | Dose (mg/Kg) | Life Prolongation Rate (%) |
|---|---|---|
| HB-2(A) | 2 | 150 |
| HB-2(B) | 2 | 155 |
| AN-7D-apoprotein | 2 | 100 |
| γ-Rhodomycin Y | 2 | 104 |

EXAMPLE 18

AN-7D-apoprotein and γ-rhodomycin Y were bound together through hydrogen bond and/or hydrophobic bond by the same way as in Example 2 to give substances HBW-2(A) and (B).

The physical and chemical properties of these HBW-2 substances are shown below, and their anticancer activity against mouse L1210 cells is summarized in Table 18.

Molar ratio of AN-7D-apoprotein to γ-rhodomycin Y: 1:1 for (A), and 1:5 for (B)
(1) Appearance: Red powder (for all)
(2) Molecular weight (gel filtration)
  13,000 [HBW-2(A)]
  13,000 [HBW-2(B)]
(3) N-terminated amino acid: Alanine (for all)
(4) Isoelectric point: pH 3.2 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).

(8) UV absorption spectrum: As shown in FIG. 41 [optical density (O.D) plotted against wavelength (nm)].

(9) IR absorption spectrum: As shown in FIG. 42 [KBr disk; transmittance (%) plotted against wave number (cm$^{-1}$)].

TABLE 18

| Drug | Dose (mg/Kg) | Life Prolongation Rate (%) |
|---|---|---|
| HBW-2(A) | 1 | 212 |
| HBW-2(B) | 1 | 285 |
| AN-7D-apoprotein | 2 | 100 |
| γ-Rhodomycin Y | 2 | 104 |

EXAMPLE 19

NCS-apoprotein and γ-rhodomycin Y were bound together through hydrogen bond and/or hydrophobic bond by the same way as in Example 1 to give substances HB-22(A) and (B).

The physical and chemical properties of these HB-22 substances are shown below, and their anticancer activity against mouse L1210 cells is summarized in Table 19.

Molar ratio of NCS-apoprotein to γ-rhodomycin Y: 1:1 for (A), and 1:5 for (B)

(1) Appearance: Red powder (for all)
(2) Molecular weight (gel filtration):
   13,000 [HB-22(A)]
   13,000 [HB-22(B)]
(3) N-terminated amino acid: Alanine (for all)
(4) Isoelectric point: pH 3.2 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 43 [optical density (O.D) plotted against wavelength (nm)].
(9) IR absorption spectrum: As shown in FIG. 44 [KBr disk; transmittance (%) plotted against wave number (cm$^{-1}$)].

TABLE 19

| Drug | Dose (mg/Kg) | Life Prolongation Rate (%) |
|---|---|---|
| HB-22(A) | 1 | 145 |
| HB-22(B) | 1 | 150 |
| NCS-apoprotein | 2 | 101 |
| γ-Rhodomycin Y | 2 | 104 |

EXAMPLE 20

NCS-apoprotein and γ-rhodomycin Y were bound together through hydrogen bond and/or hydrophobic bond by the same way as in Example 2 to give substances HBW-22(A) and (B).

The physical and chemical properties of these HBW-22 substances are shown below, and their anticancer activity against mouse L1210 cells is summarized in Table 20.

Molar ratio of NCS-apoprotein to γ-rhodomycin Y: 1:1 for (A), and 1:5 for (B)

(1) Appearance: Red powder (for all)
(2) Molecular weight (gel filtration):
   13,000 [HBW-22(A)]
   13,000 [HBW-22(B)]
(3) N-terminated amino acid: Alanine (for all)
(4) Isoelectric point: pH 3.2 (for all)
(5) Melting pont: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 45 [optical density (O.D) plotted against wavelength (nm)].
(9) IR absorption spectrum: As shown in FIG. 46 [KBr disk; transmittance (%) plotted against wave number (cm$^{-1}$)].

TABLE 20

| Drug | Dose (mg/Kg) | Life Prolongation Rate (%) |
|---|---|---|
| HBW-22(A) | 1 | 158 |
| HBW-22(B) | 1 | 162 |
| NCS-apoprotein | 2 | 101 |
| γ-Rhodomycin Y | 2 | 104 |

EXAMPLE 21

AN-3 and γ-rhodomycin Y were bound together through hydrogen bond and/or hydrophobic bond by the same way as in Example 1 to give substances HB-23(A) and (B).

The physical and chemical properties of these HB-23 substances are shown below, and their anticancer activity against mouse L1210 cells is summarized in Table 21.

Molar ratio of AN-3 to γ-rhodomycin Y: 1:1 for (A), and 1:5 for (B)

(1) Appearance: Red powder (for all)
(2) Molecular weight (gel filtration)
   13,000 [HB-23(A)]
   13,000 [HB-23(B)]
(3) N-terminated amino acids: Alanine (for all)
(4) Isoelectric point: pH 7.6 (for all)
(5) Melting point: Show no definite melting point, all charring with decomposition at above 230° C.
(6) Ninhydrin and biuret reactions: Positive response to both (for all).
(7) Solubility: soluble in water; insoluble in methanol, ethanol, butanol and propanol (for all).
(8) UV absorption spectrum: As shown in FIG. 47 [optical density (O.D) plotted against wavelength (nm)].
(9) IR absorption spectrum: As shown in FIG. 48 [KBr disk; transmittance (%) plotted against wave number (cm$^{-1}$)].

TABLE 21

| Drug | Dose (mg/Kg) | Life Prolongation Rate (%) |
|---|---|---|
| HB-23(A) | 2 | 128 |
| HB-23(B) | 2 | 130 |
| AN-3 | 2 | <100 |
| γ-Rhodomycin Y | 2 | 104 |

EXAMPLE 22

AN-3 and γ-rhodomycin Y were bound together through hydrogen bond and/or hydrophobic bond by the same way as in Example 2 to give substances HBW-23(A) and (B).

The physical and chemical properties of these HBW-23 substances are shown below, and their anticancer activity against mouse L1210 cells is summarized in Table 22.

Molar ratio of AN-3 to γ-rhodomycin Y: 1:1 for (A), and 1:5 for (B)

(1) Appearance: Red powder (for all)
(2) Molecular weight (gel filtration):
    13,000 [HBW-23(A)]
    13,000 [HBW-23(B)]
(3) N-terminated amino acid: Alanine (for all)
(4) Isoelectric point: pH 7.6 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 49 [optical density (O.D) plotted against wavelength (nm)].
(9) IR absorption spectrum: As shown in FIG. 50 [KBr disk; transmittance (%) plotted against wave number $(cm^{-1})$].

TABLE 22

| Drug | Dose (mg/Kg) | Life Prolongation Rate (%) |
|---|---|---|
| HBW-23(A) | 1 | 130 |
| HBW-23(B) | 1 | 135 |
| AN-3 | 2 | <100 |
| γ-Rhodomycin Y | 2 | 104 |

EXAMPLE 23

AN-7D-apoprotein and cosmomycin A were bound together through hydrogen bond and/or hydrophobic bond by the same way as in Example 1 to give substances HB-3(A) and (B).

The physical and chemical properties of these HB-3 substances are shown below, and their anticancer activity against mouse L1210 cells is summarized in Table 23.
Molar ratio of AN-7D-apoprotein to cosmomycin A: 1:1 for (A), and 1:5 for (B)
(1) Appearance: Red powder (for all)
(2) Molecular weight (gel filtration):
    13,000 [HB-3(A)]
    13,000 [HB-3(B)]
(3) N-terminated amino acid: Alanine (for all)
(4) Isoelectric point: pH 3.2 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 51 [optical density (O.D) plotted against wavelength (nm)].
(9) IR absorption spectrum: As shown in FIG. 52 [KBr disk; transmittance (%) plotted against wave number $(cm^{-1})$].

TABLE 23

| Drug | Dose (mg/Kg) | Life Prolongation Rate (%) |
|---|---|---|
| HB-3(A) | 2 | 175 |
| HB-3(B) | 2 | 182 |
| AN-7D-apoprotein | 2 | 100 |
| Cosmomycin A | 2 | 126 |

EXAMPLE 24

AN-7D-apoprotein and cosmomycin A were bound together through hydrogen bond and/or hydrophobic bond by the same way as in Example 2 to give substances HBW-3(A) and (B).

The physical and chemical properties of these HBW-3 substances are shown below, and their anticancer activity against mouse L1210 cells is summarized in Table 24.
Molar ratio of AN-7D-apoprotein to cosmomycin A: 1:1 for (A), and 1:5 for (B)
(1) Appearance: Red powder (for all)
(2) Molecular weight (gel filtration):
    13,000 [HBW-3(A)]
    13,000 [HBW-3(B)]
(3) N-terminated amino acid: Alanine (for all)
(4) Isoelectric point: pH 3.2 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 53 [optical density (O.D) plotted against wavelength (nm)].
(9) IR absorption spectrum: As shown in FIG. 54 [KBr disk; transmittance (%) plotted against wave number $(cm^{-1})$].

TABLE 24

| Drug | Dose (mg/Kg) | Life Prolongation Rate (%) |
|---|---|---|
| HBW-3(A) | 1 | 182 |
| HBW-3(B) | 1 | 185 |
| AN-7D-apoprotein | 2 | 100 |
| Cosmomycin A | 2 | 126 |

EXAMPLE 25

NCS-apoprotein and cosmomycin A were bound together through hydrogen bond and/or hydrophobic bond by the same way as in Example 1 to give substances HB-18(A) and (B).

The physical and chemical properties of these HB-18 substances are shown below, and their anticancer activity against mouse L1210 cells is summarized in Table 25.
Molar ratio of NCS-apoprotein to cosmomycin A: 1:1 for (A), and 1:5 for (B)
(1) Appearance: Red powder (for all)
(2) Molecular weight (gel filtration):
    13,000 [HB-18(A)]
    13,000 [HB-18(B)]
(3) N-terminated amino acid: Alanine (for all)
(4) Isoelectric point: pH 3.2 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 55 [optical density (O.D) plotted against wavelength (nm)].
(9) IR absorption spectrum: As shown in FIG. 56 [KBr disk; transmittance (%) plotted against wave number $(cm^{-1})$].

TABLE 25

| Drug | Dose (mg/Kg) | Life Prolongation Rate (%) |
|---|---|---|
| HB-18(A) | 2 | 168 |
| HB-18(B) | 2 | 170 |
| NCS-apoprotein | 2 | 101 |
| Cosmomycin A | 2 | 126 |

EXAMPLE 26

NCS-apoprotein and cosmomycin A were bound together through hydrogen bond and/or hydrophobic bond by the same way as in Example 2 to give substances HBW-18(A) and (B).

The physical and chemical properties at these HBW-18 substances are shown below, and their anticancer activity against mouse L1210 cells is summarized in Table 26.

Molar ratio of NCS-apoprotein to cosmomycin A: 1:1 for (A), and 1:5 for (B)

(1) Appearance: Red powder (for all)
(2) Molecular weight (gel filtration):
    13,000 [HBW-18(A)]
    13,000 [HBW-18(B)]
(3) N-terminated amino acid: Alanine (for all)
(4) Isoelectric point: pH 3.2 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 57 [optical density (O.D) plotted against wavelength (nm)].
(9) IR absorption spectrum: As shown in FIG. 58 [KBr disk; transmittance (%) plotted against wave number $(cm^{-1})$].

TABLE 26

| Drug | Dose (mg/Kg) | Life Prolongation Rate (%) |
|---|---|---|
| HBW-18(A) | 1 | 170 |
| HBW-18(B) | 1 | 175 |
| NCS-apoprotein | 2 | 101 |
| Cosmomycin A | 2 | 126 |

EXAMPLE 27

AN-3 and cosmomycin A were bound together through hydrogen bond and/or hydrophobic bond by the same way as in Example 1 to give substances HB-19(A) and (B).

The physical and chemical properties of these HB-19 substances are shown below, and their anticancer activity against mouse L1210 cells is summarized in Table 27.

Molar ratio of AN-3 to cosmomycin A: 1:1 for (A), and 1:5 for (B)

(1) Appearance: Red powder (for all)
(2) Molecular weight (gel filtration):
    13,000 [HB-19(A)]
    13,000 [HB-19(B)]
(3) N-terminated amino acid: Alanine (for all)
(4) Isoelectric point: pH 7.6 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 59 [optical density (O.D) plotted against wavelength (nm)].
(9) IR absorption spectrum: As shown in FIG. 60 [KBr disk; transmittance (%) plotted against wave number $(cm^{-1})$].

TABLE 27

| Drug | Dose (mg/Kg) | Life Prolongation Rate (%) |
|---|---|---|
| HB-19(A) | 1 | 150 |
| HB-19(B) | 1 | 158 |
| AN-3 | 2 | <100 |
| Cosmomycin A | 2 | 126 |

EXAMPLE 28

AN-3 cosmomycin A were bound together through hydrogen bond and/or hydrophobic bond by the same way as in Example 2 to give substances HBW-19(A) and (B).

The physical and chemical properties of these HBW-19 substances are shown below, and their anticancer activity against mouse L1210 cells is summarized in Table 28.

Molar ratio of AN-3 to cosmomycin A: 1:1 for (A), and 1:5 for (B)

(1) Appearance: Red powder (for all)
(2) Molecular weight (gel filtration):
    13,000 [HBW-19(A)]
    13,000 [HBW-19(B)]
(3) N-terminated amino acid: Alanine (for all)
(4) Isoelectric point: pH 7.6 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 61 [optical density (O.D) plotted against wavelength (nm)].
(9) IR absorption spectrum: As shown in FIG. 62 [KBr disk; transmittance (%) plotted against wave number $(cm^{-1})$].

TABLE 28

| Drug | Dose (mg/Kg) | Life Prolongation Rate (%) |
|---|---|---|
| HBW-19(A) | 1 | 155 |
| HBW-19(B) | 1 | 163 |
| AN-3 | 2 | <100 |
| Cosmomycin A | 2 | 126 |

EXAMPLE 29

NCS-apoprotein and aclacinomycin A were bound together through hydrogen bond and/or hydrophobic bond by the same was as in Example 1 to give substances HB-21(A) and (B).

The physical and chemical properties of these HB-21 substances are shown below, and their anticancer activity against mouse L1210 cells is summarized in Table 29.

Molar ratio of NCS-apoprotein to aclacinomycin A: 1:1 for (A), and 1:5 for (B)

(1) Appearance: Yellow powder (for all)
(2) Molecular weight (gel filtration):
    13,000 [HB-21(A)]
    13,000 [HB-21(B)]
(3) N-terminated amino acid: Alanine (for all)
(4) Isoelectric point: pH 3.2 (for all)
(5) Melting point: Show no definite melting point, all charring with decomposition at above 230° C.
(6) Ninhydrin and biuret reactions: Positive response to both (for all).

(7) Solubility: Soluble in water; insoluble in methanol, ethanol, butanol and propanol (for all).
(8) UV absorption spectrum: As shown in FIG. 63 [optical density (O.D) plotted against wavelength (nm)].
(9) IR absorption spectrum: As shown in FIG. 64 [KBr disk; transmittance (%) plotted against wave number $(cm^{-1})$].

TABLE 29

| Drug | Dose (mg/Kg) | Life Prolongation Rate (%) |
|---|---|---|
| HB-21(A) | 2 | 142 |
| HB-21(B) | 2 | 145 |
| NCS-apoprotein | 2 | 101 |
| Aclacinomycin A | 2 | 135 |

EXAMPLE 30

NCS-apoprotein and aclacinomycin A were bound together through hydrogen bond and/or hydrophobic bond by the same way as in Example 2 to give substances HBW-21(A) and (B).

The physical and chemical properties of these HBW-21 substances are shown below, and their anticancer activity against mouse L1210 cells is summarized in Table 30.

Molar ratio of NCS-apoprotein to acalacinomycin A: 1:1 for (A), and 1:5 for (B)
(1) Appearance: Yellow powder (for all)
(2) Molecular weight (gel filtration):
    13,000 [HBW-21(A)]
    13,000 [HBW-21(B)]
(3) N-terminated amino acid: Alanine (for all)
(4) Isoelectric point: pH 3.2 (for all)
(5) Melting point: Show no definite melting point, all charring with decomposition at above 230° C.
(6) Ninhydrin and biuret reactions: Positive response to both (for all).
(7) Solubility: Soluble in water; insoluble in methanol, ethanol, butanol and propanol (for all).
(8) UV absorption spectrum: As shown in FIG. 65 [optical density (O.D) plotted against wavelength (nm)].
(9) IR absorption spectrum: As shown in FIG. 66 [KBr disk; transmittance (%) plotted against wave number $(cm^{-1})$].

TABLE 30

| Drug | Dose (mg/Kg) | Life Prolongation Rate (%) |
|---|---|---|
| HBW-21(A) | 1 | 135 |
| HBW-21(B) | 1 | 162 |
| NCS-apoprotein | 2 | 101 |
| Aclacinomycin A | 2 | 135 |

EXAMPLE 31

Antibacterial activity of a compound of this invention, HBW10(A), is shown in Table 31.

TABLE 31

| | MIC (μg/ml) | | |
|---|---|---|---|
| | HBW-10(A) | Daunomycin | NCS-apoprotein |
| *Bacillus subtilis* ATCC6633 | 2.3 | 5.8 | >100 |
| *Micrococcus luteus* ATCC9341 | 0.30 | 1.2 | >100 |
| *Pseudomonas aeruginosa* ATCC10145 | >10 | >10 | >100 |

Effects of the Invention

As is apparent from the foregoing, the novel compounds of this invention exhibit carcinocidal activity at lower doses and show more powerful carcinocidal action at the same dose level, compared with conventional anthracycline anti-tumor substances. In addition, the compounds of this invention also have antibacterial activity.

Figure 1:
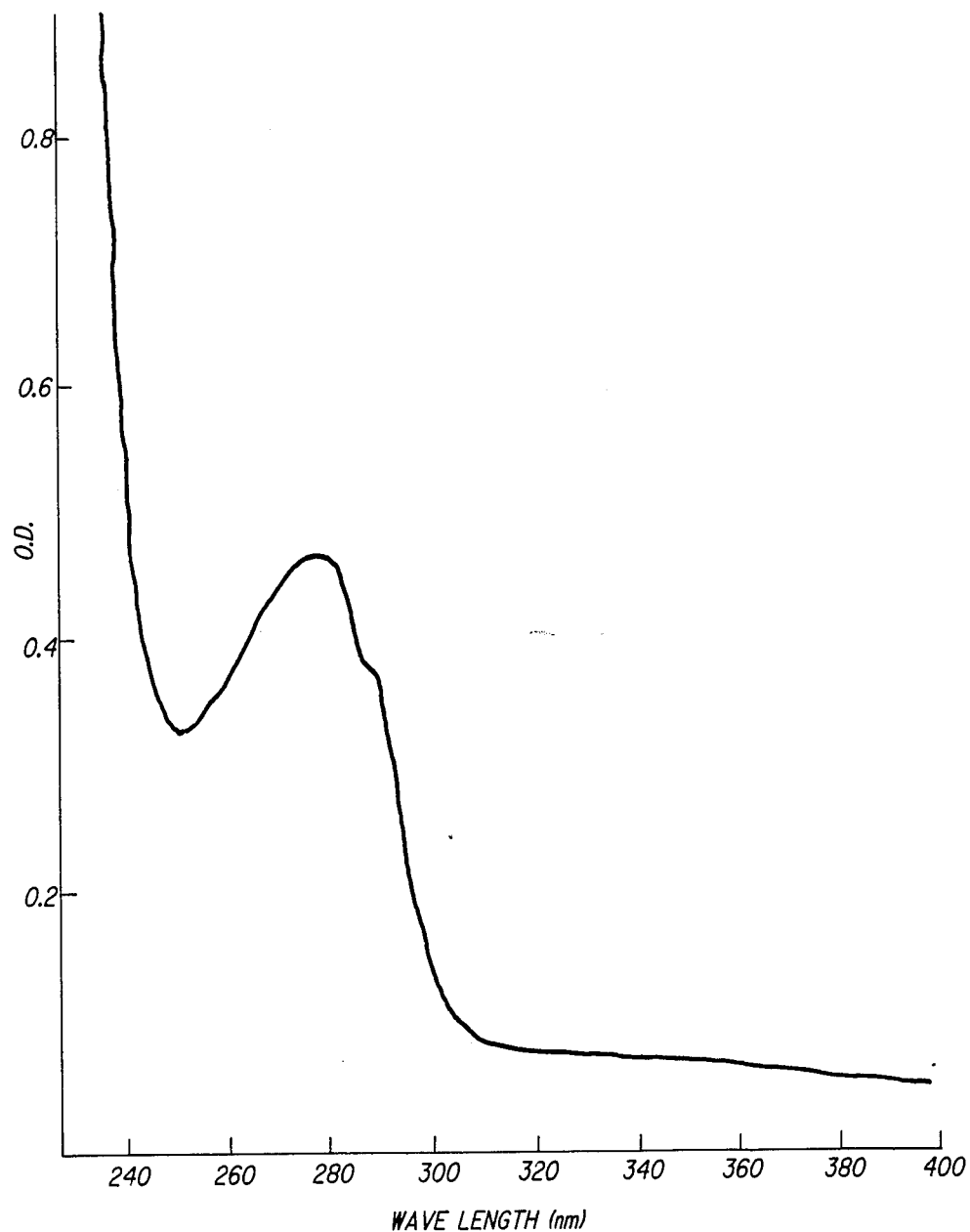
FIG. 1 is UV absorption spectrum of the apoprotein of neocarzinostatin.
Figure 2:
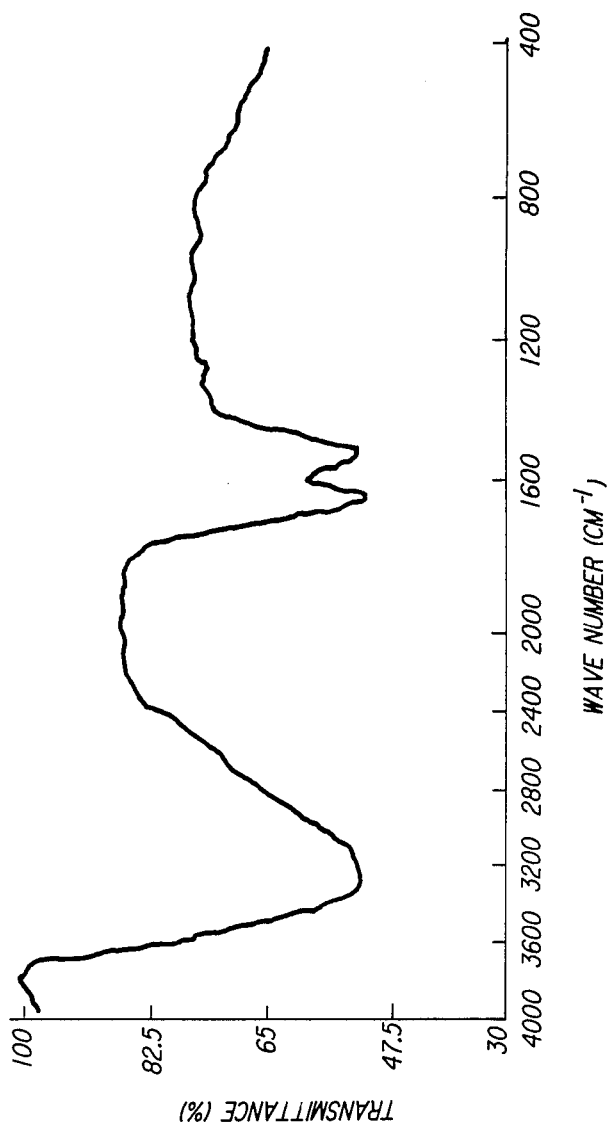
FIG. 2 is IR absorption spectrum of the same.
Figure 3:
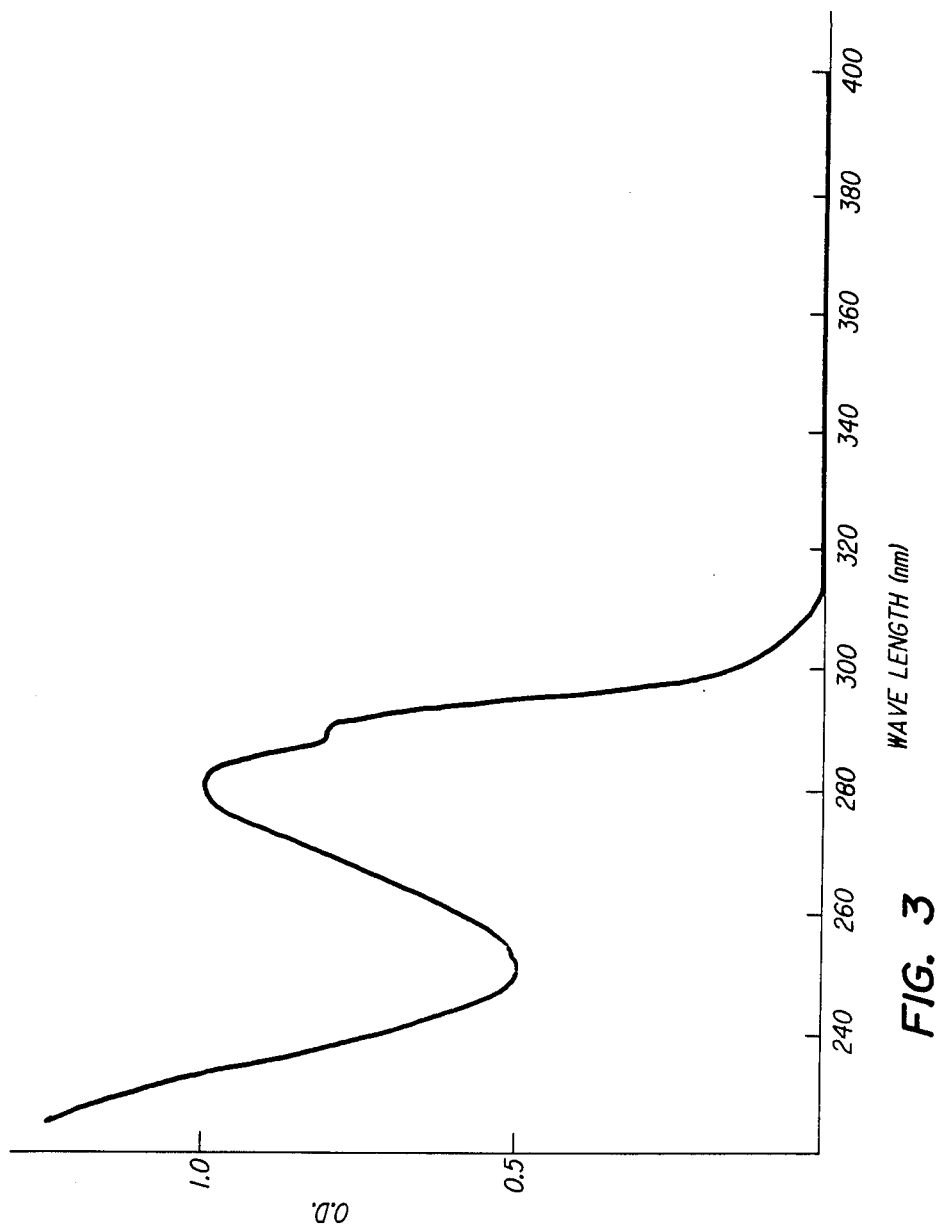
FIG. 3 is UV absorption spectrum of AN-7D-apoprotein.
Figure 4:
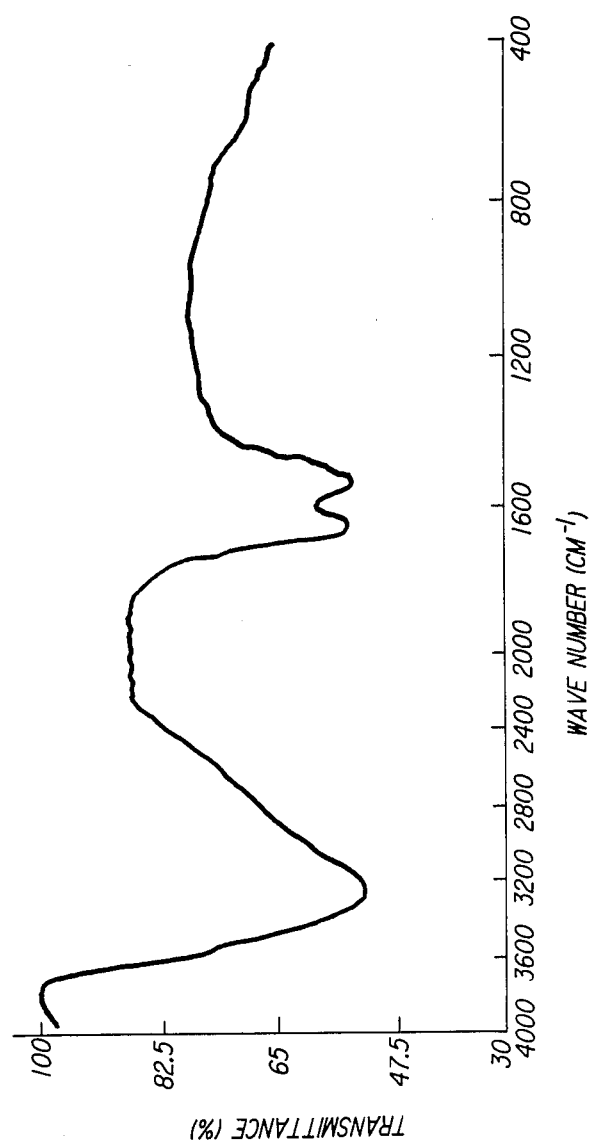
FIG. 4 is IR absorption spectrum of the same.
Figure 5:
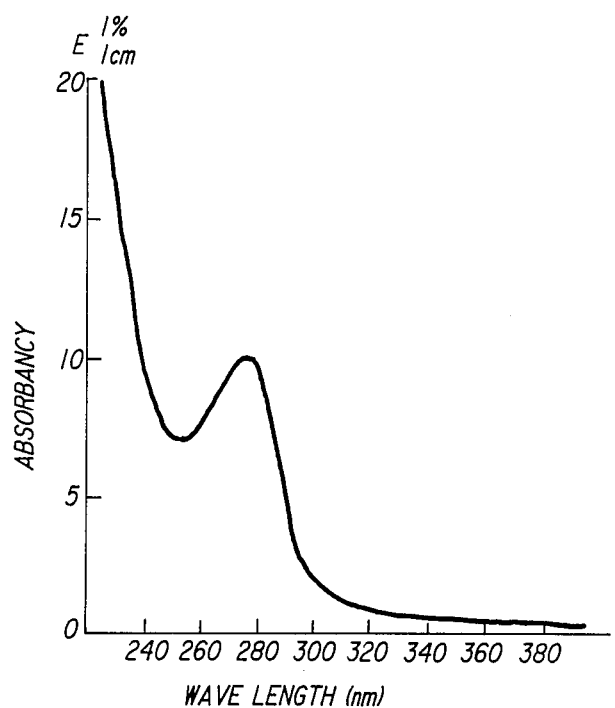
FIG. 5 is UV absorption spectrum of AN-3.
Figure 6:
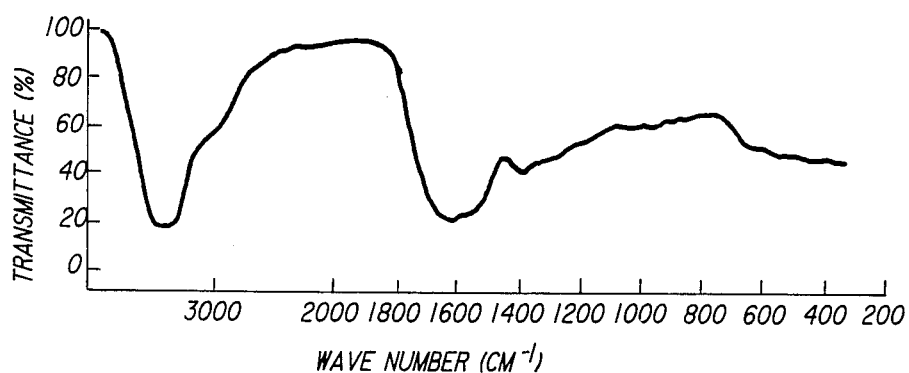
FIG. 6 is IR absorption spectrum of the same.
Figure 7:
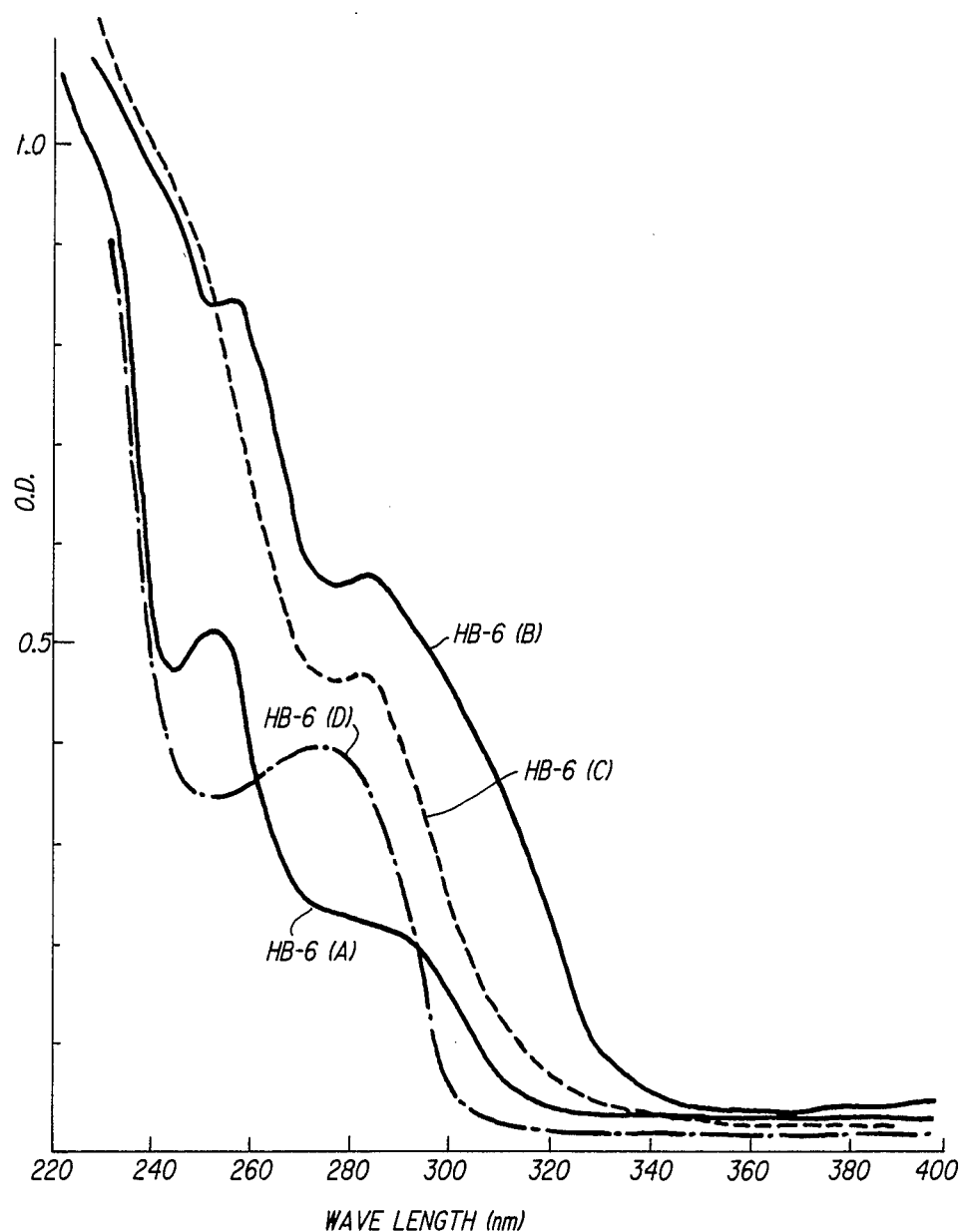
FIGS. 7, 9, 11, 13, 15, 17, 19, 21, 23, 25, 27, 29, 31, 33, 35, 37, 39, 41, 43, 45, 47, 49, 51, 53, 55, 57, 59, 61, 63 and 65 are UV absorption spectra of the compounds of this invention described in Examples; and
IR absorption spectra of the respective compounds are shown in FIGS. 8, 10, 12, 14, 16, 18, 20, 22, 24, 26, 28, 30, 32, 34, 36, 38, 40, 42, 44, 46, 48, 50, 52, 54, 56, 58, 60, 62, 64 and 66.
Figure 8:
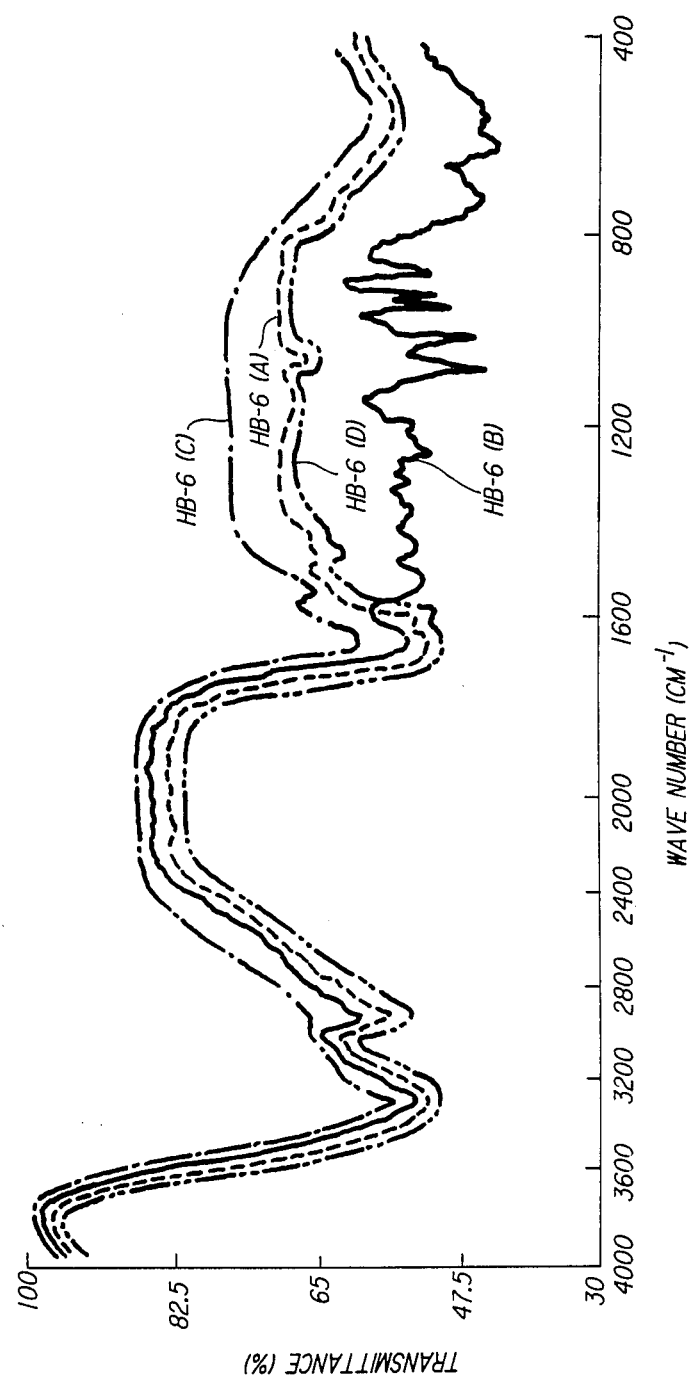
Figure 9:
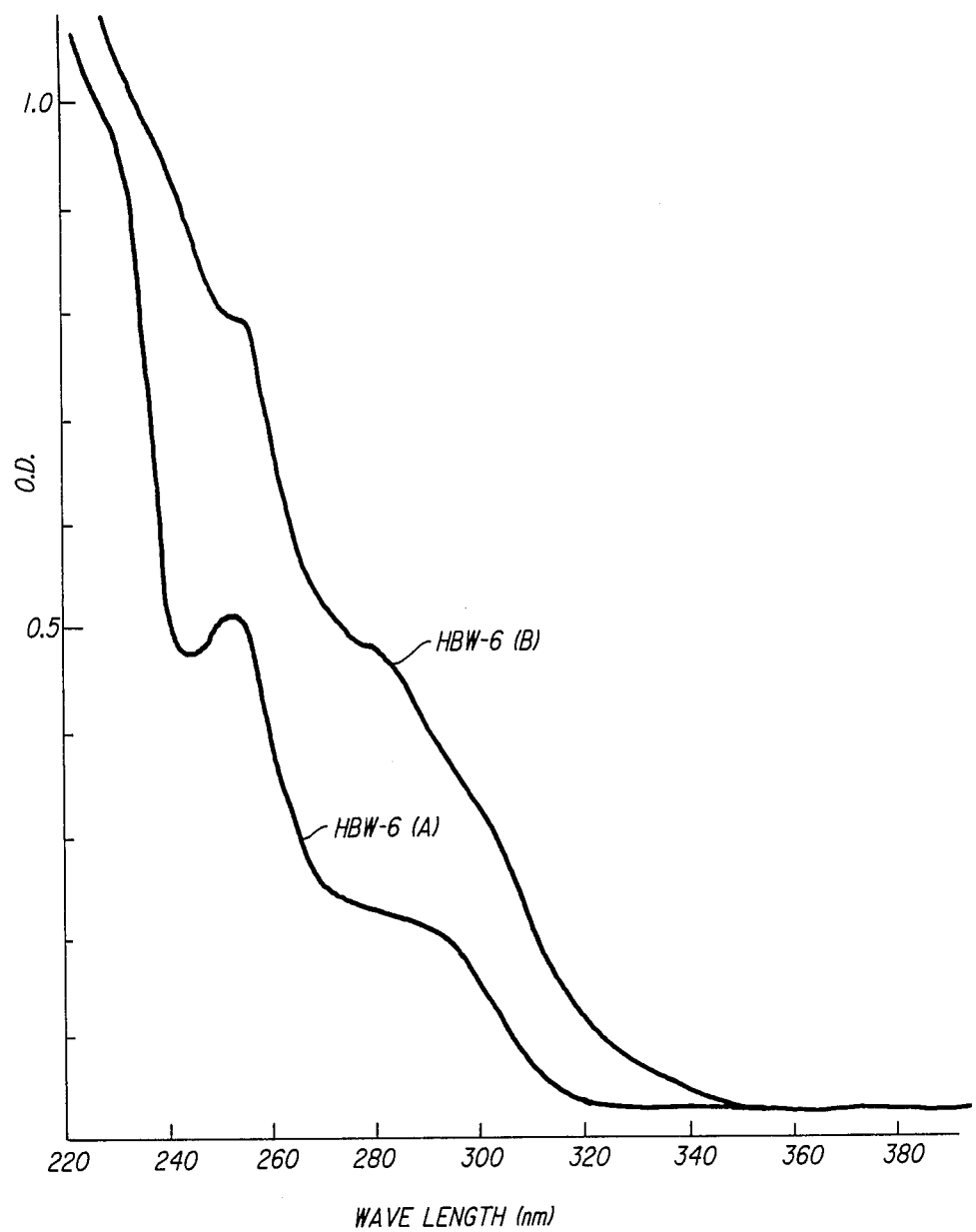
Figure 10:
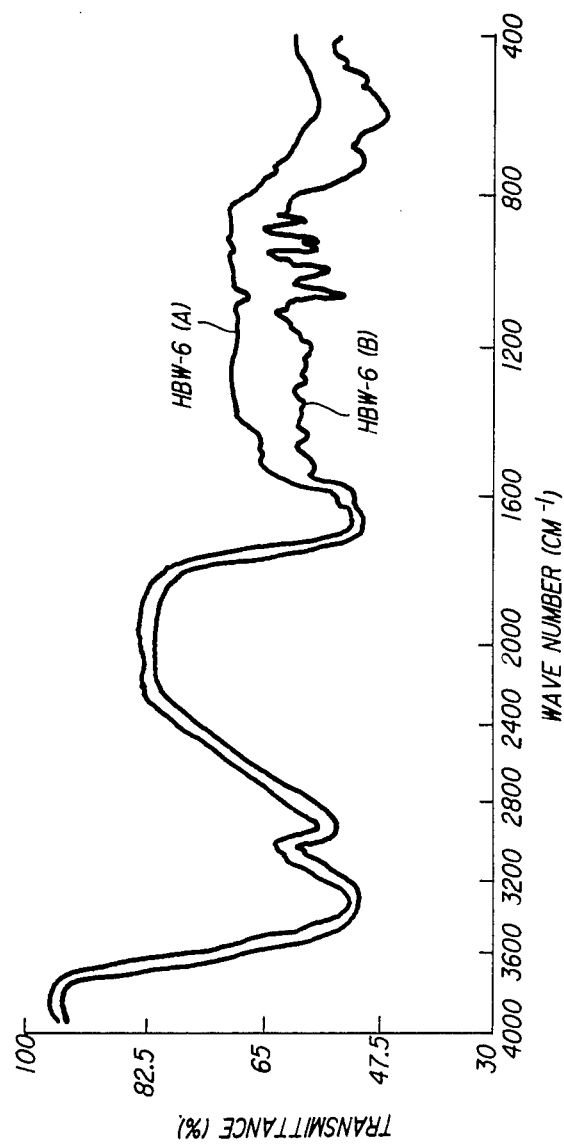
Figure 11:
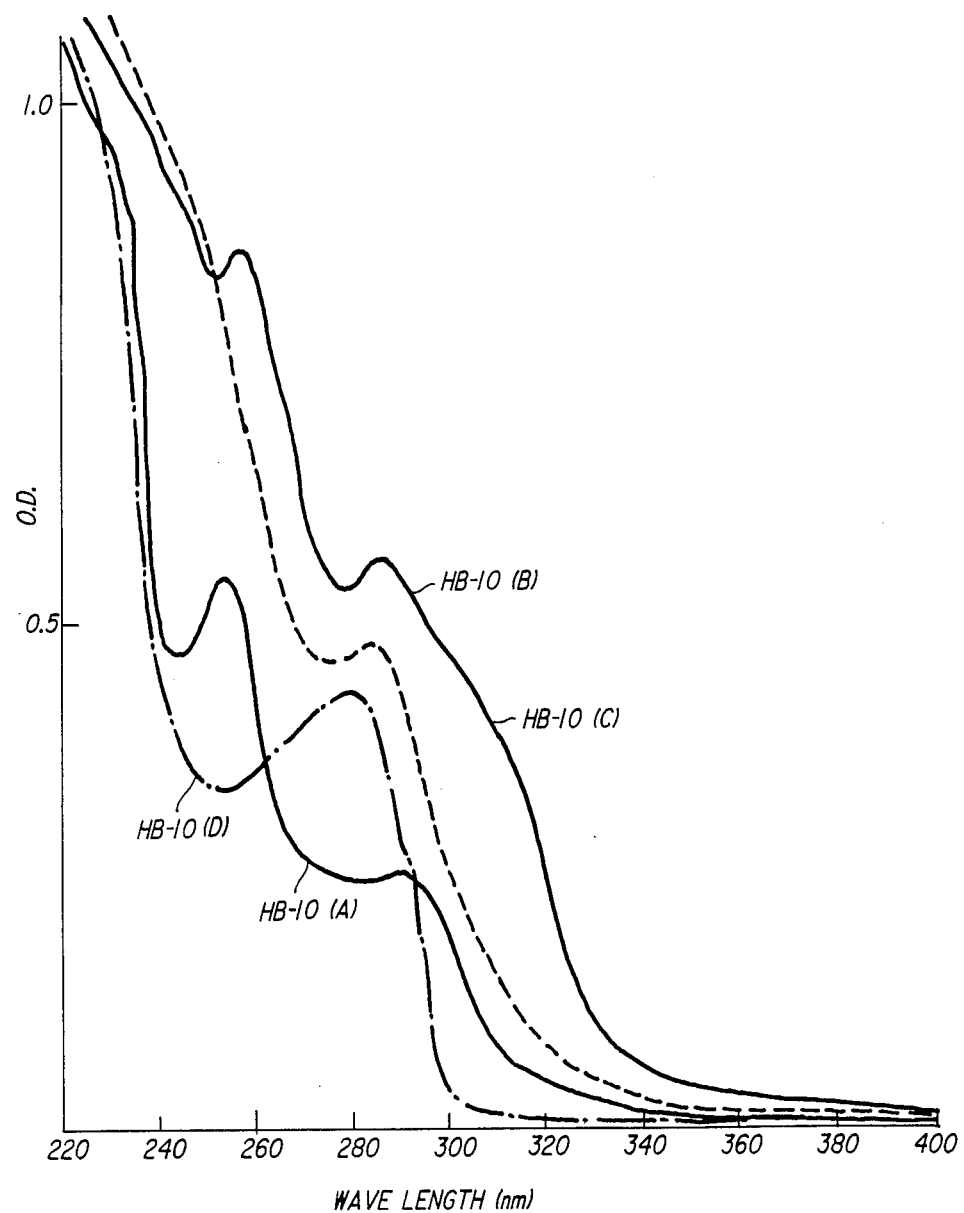
Figure 12:
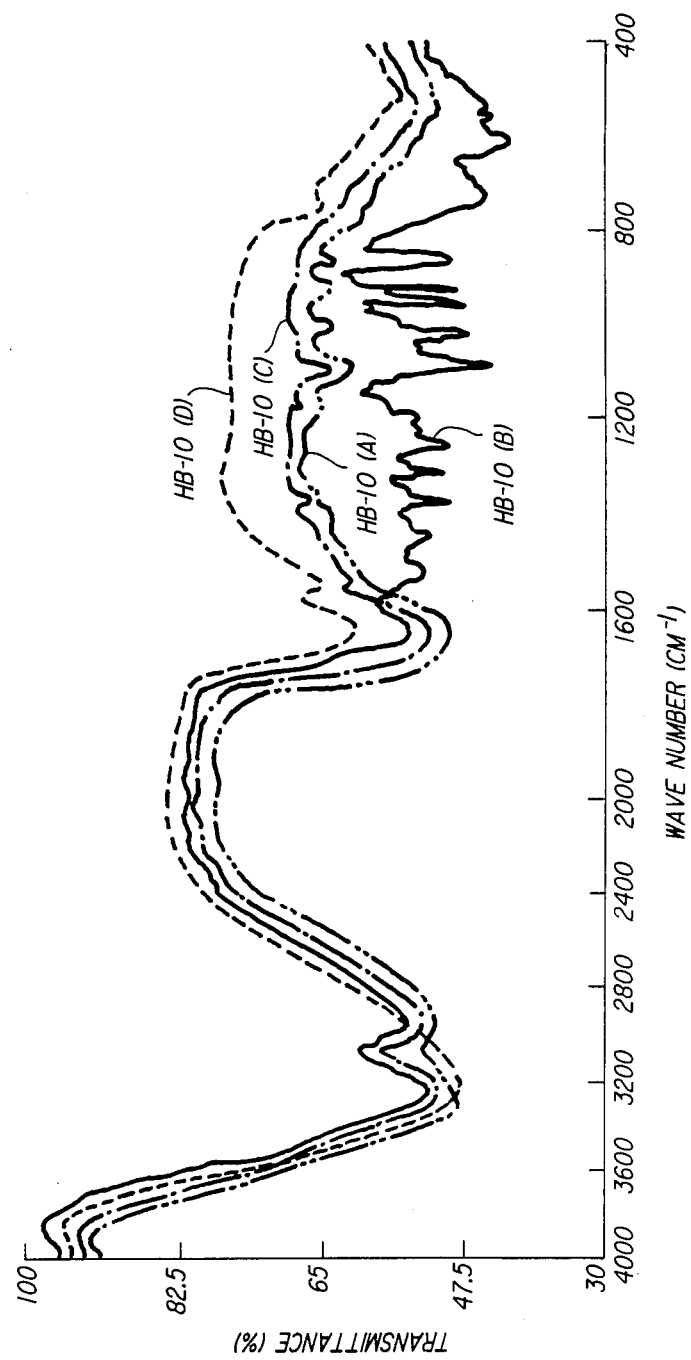
Figure 13:
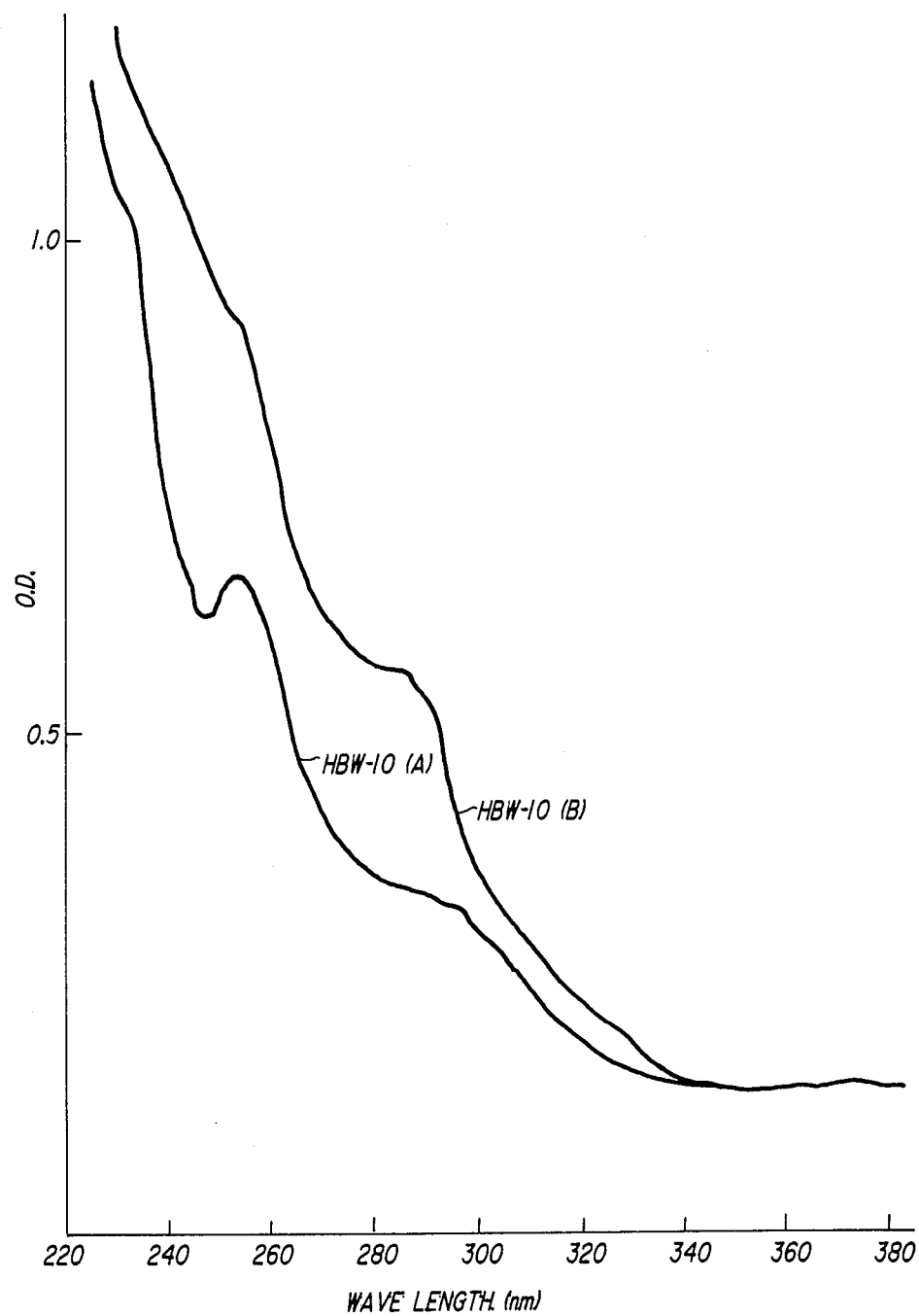
Figure 14:
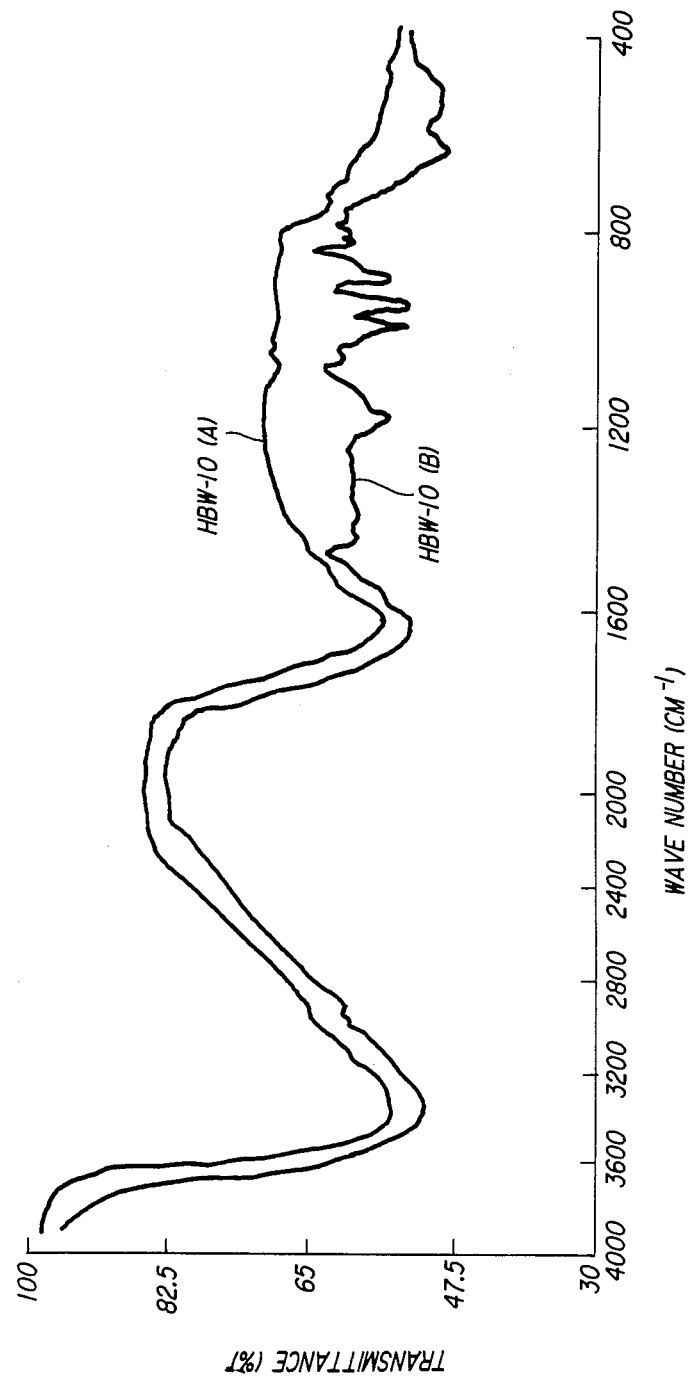
Figure 15:
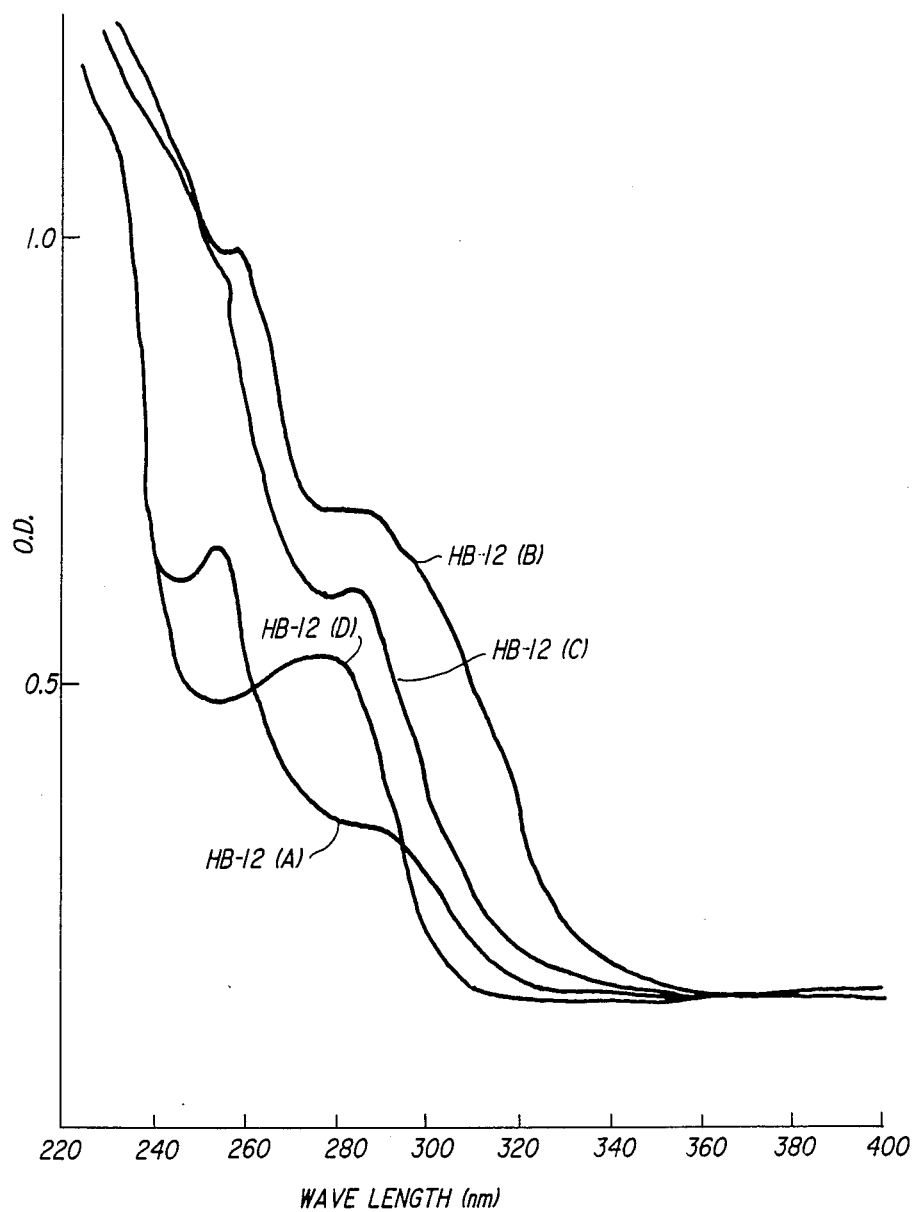
Figure 16:
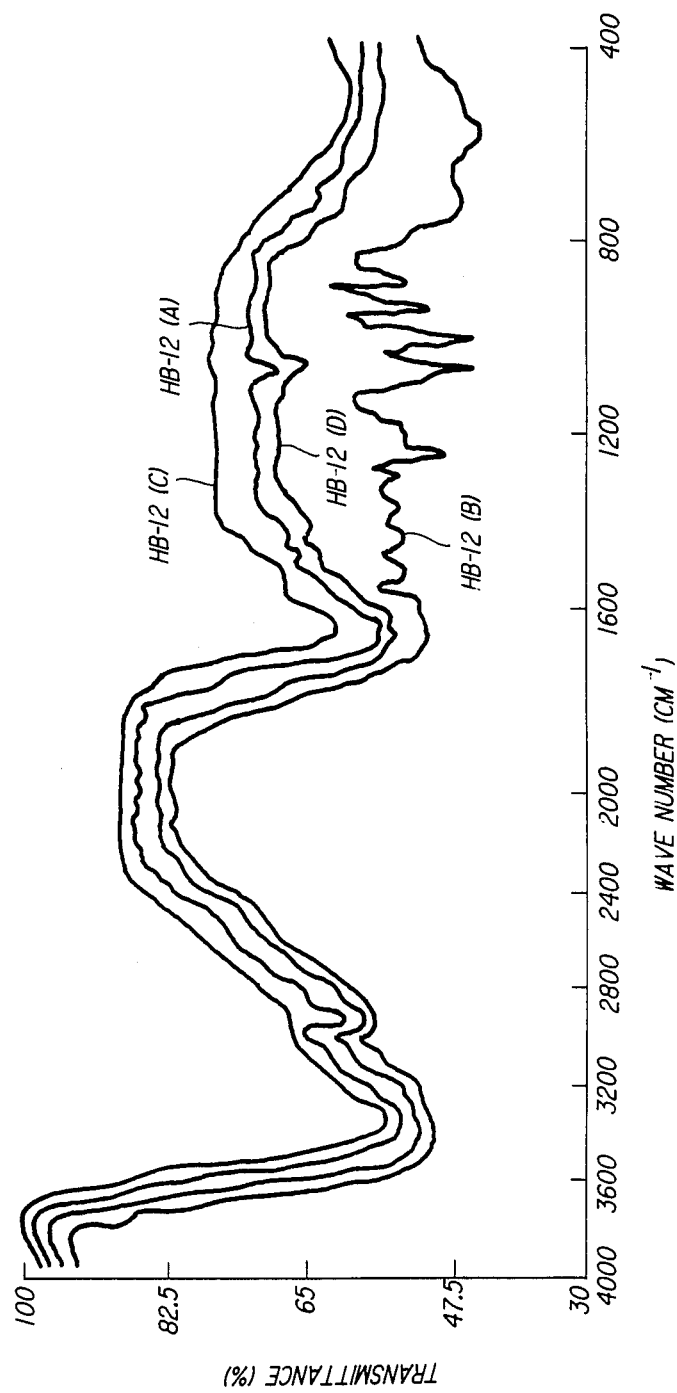
Figure 17:
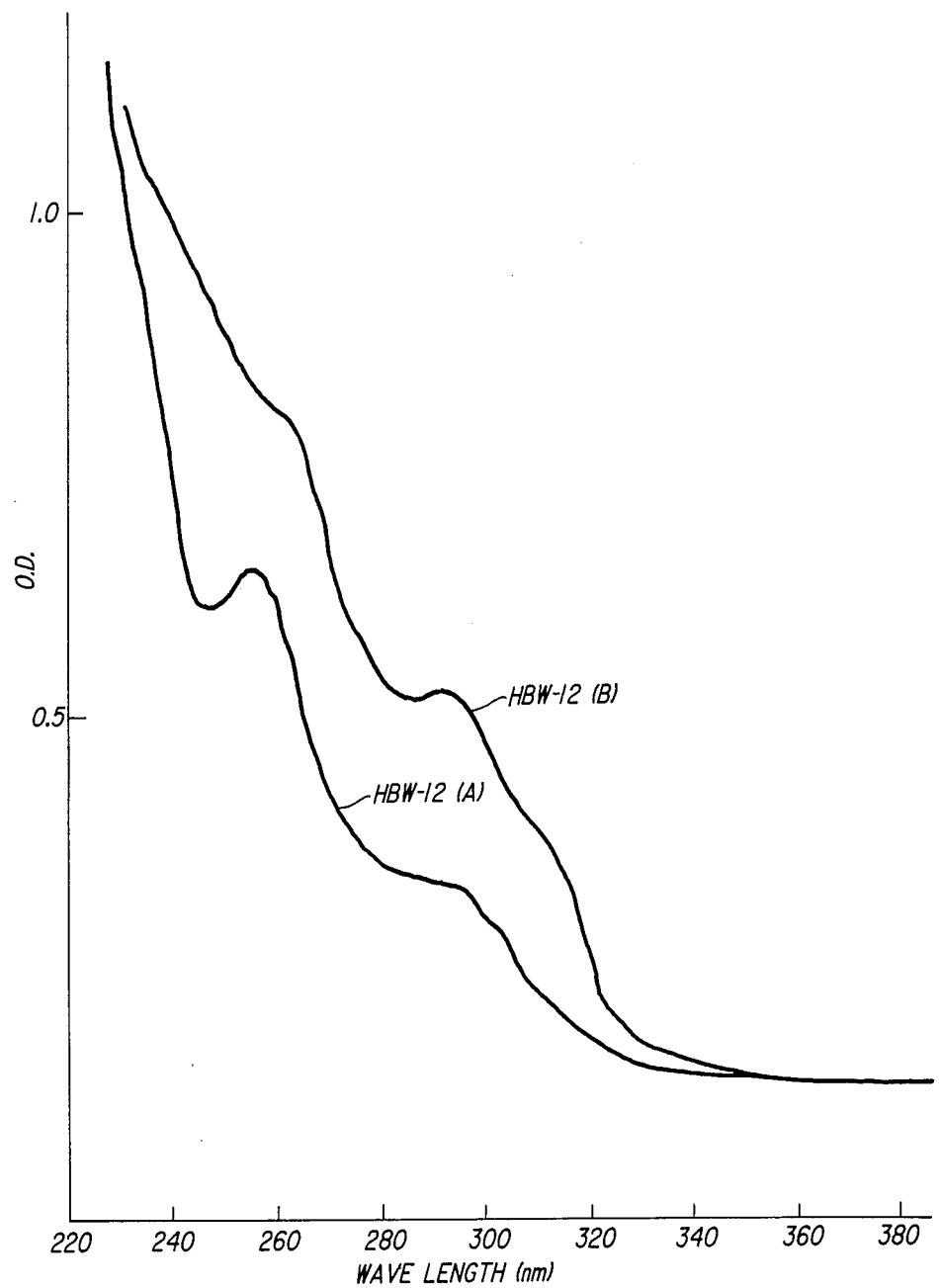
Figure 18:
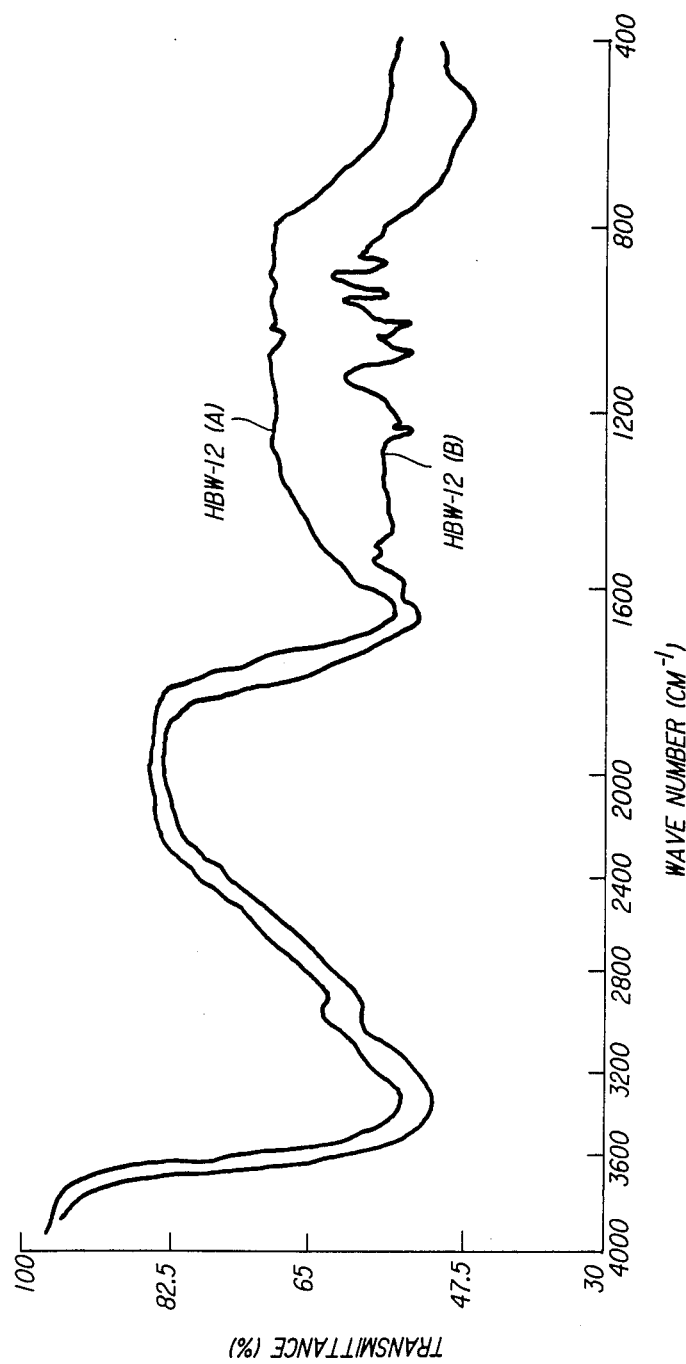
Figure 19:
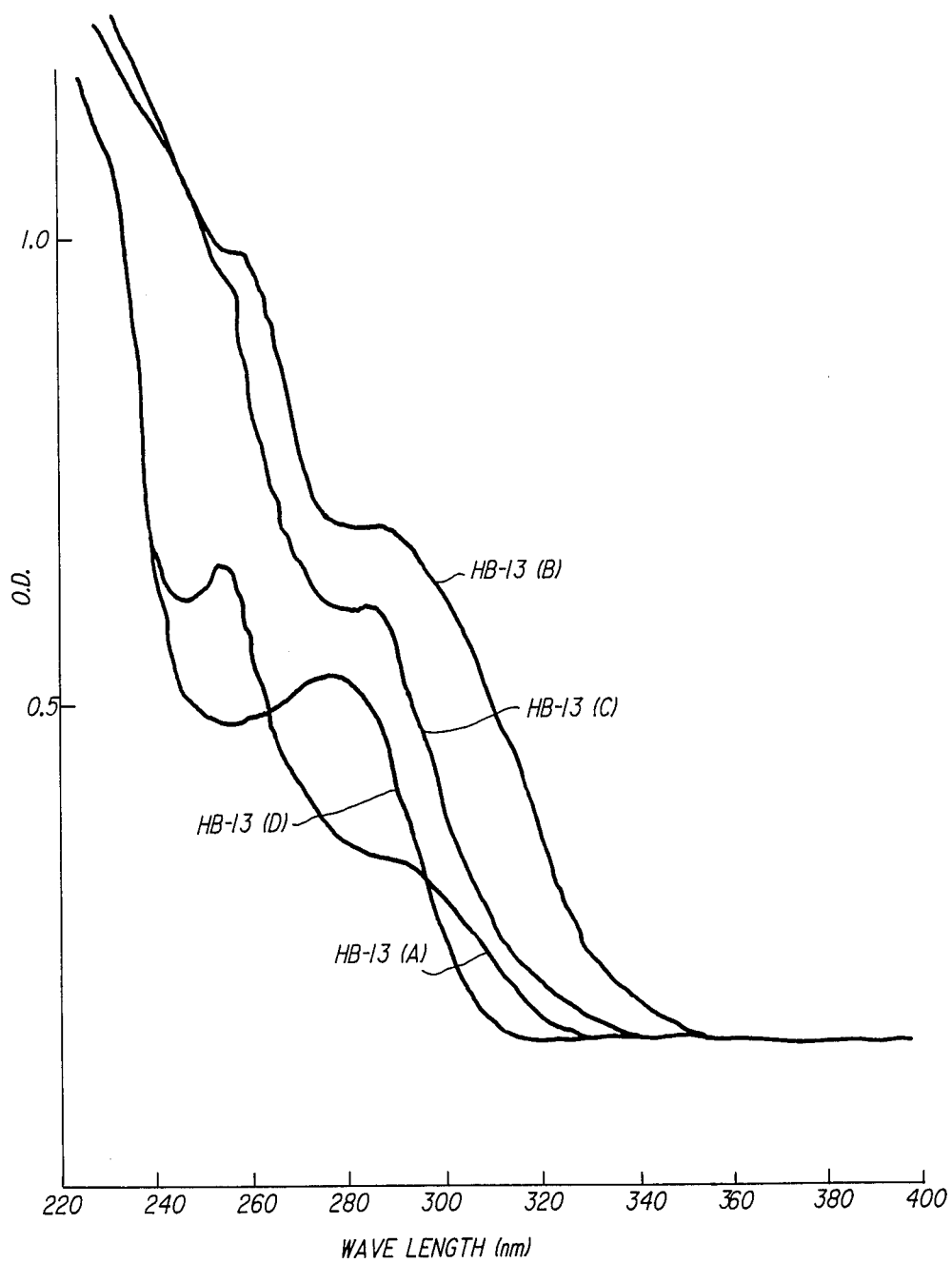
Figure 20:
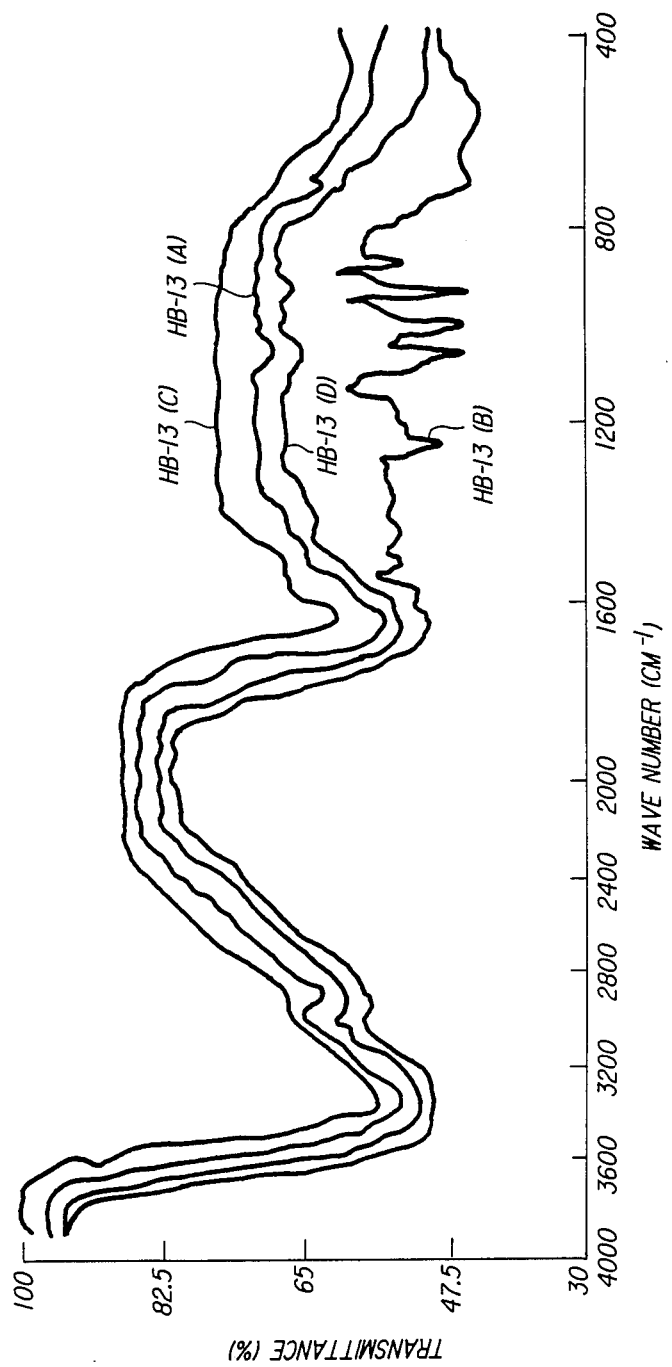
Figure 21:
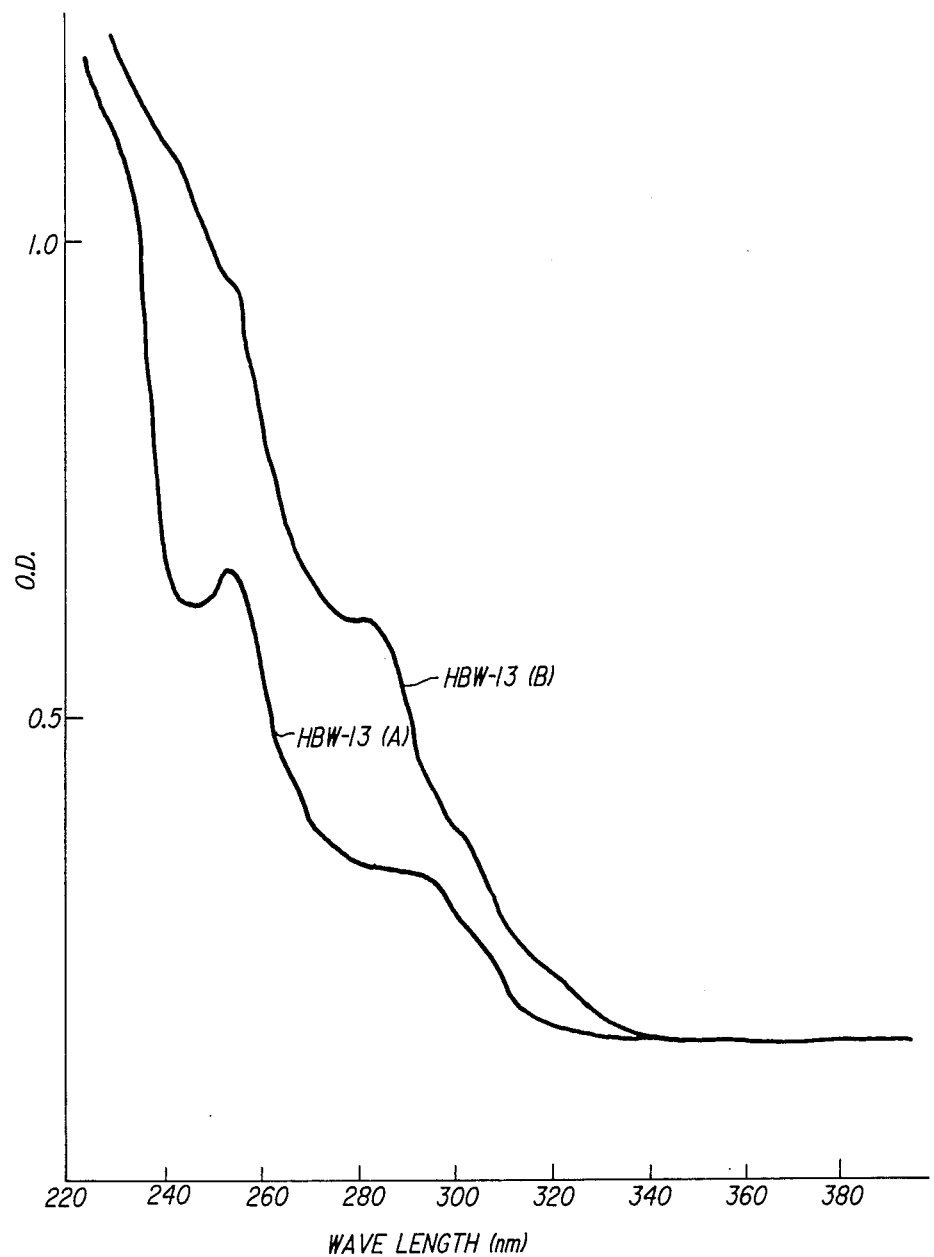
Figure 22:
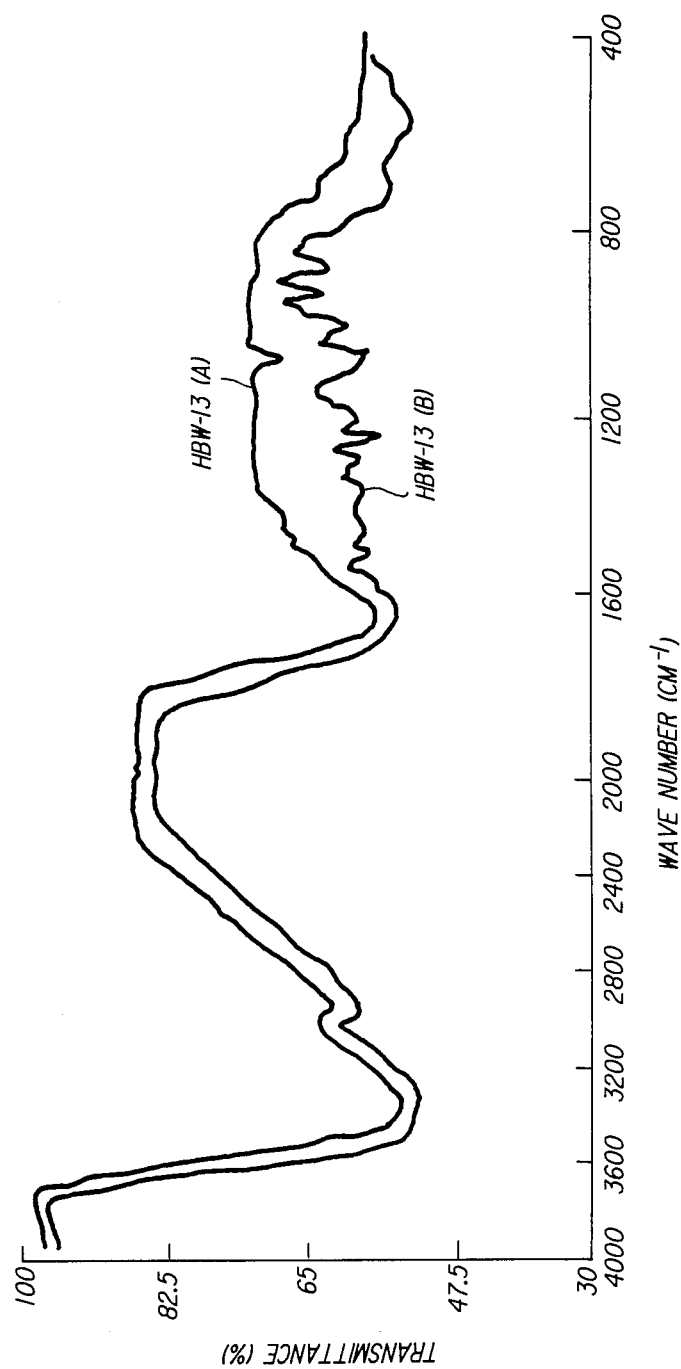
Figure 23:
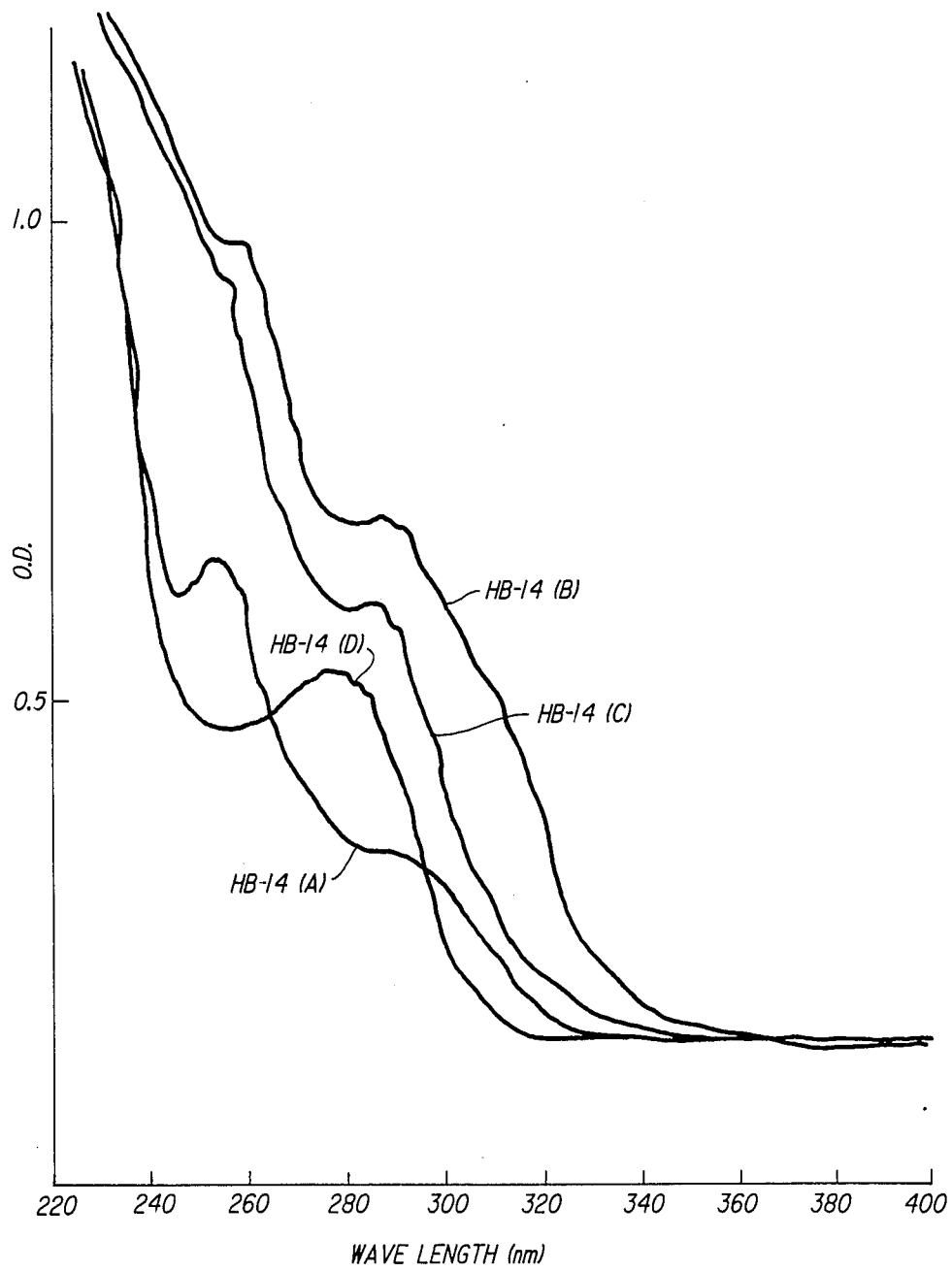
Figure 24:
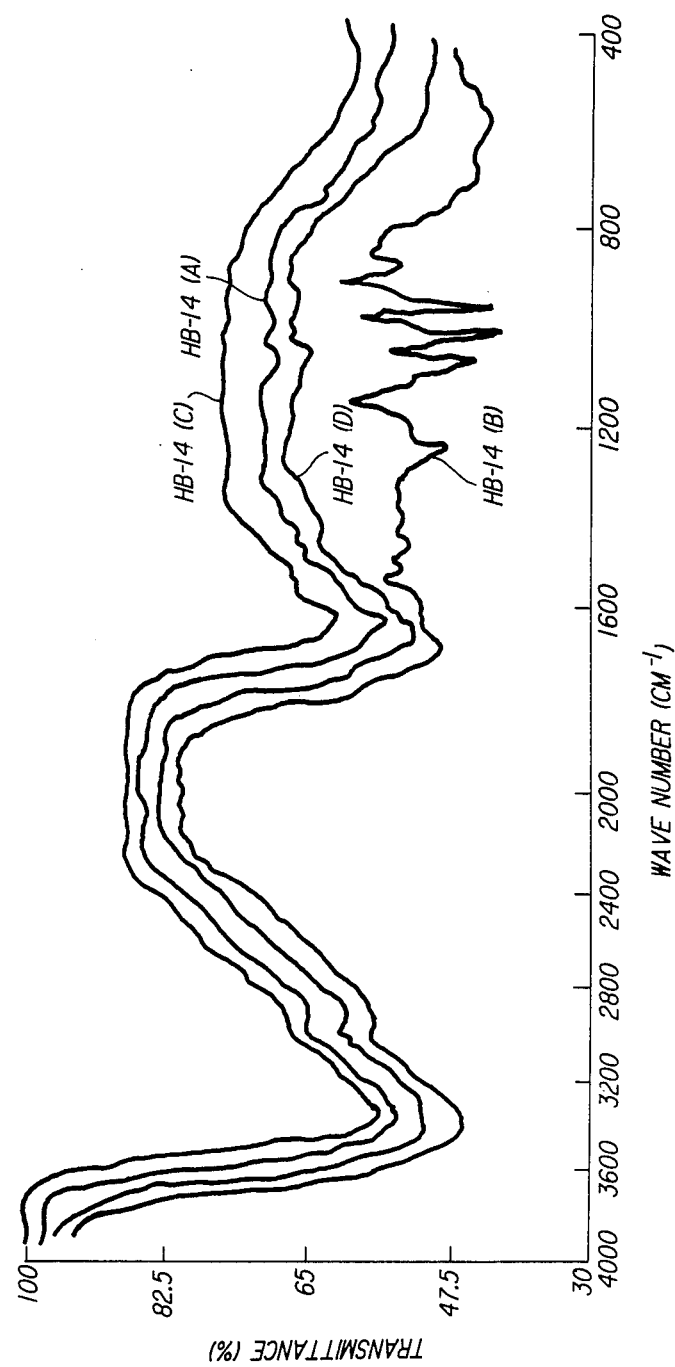
Figure 25:
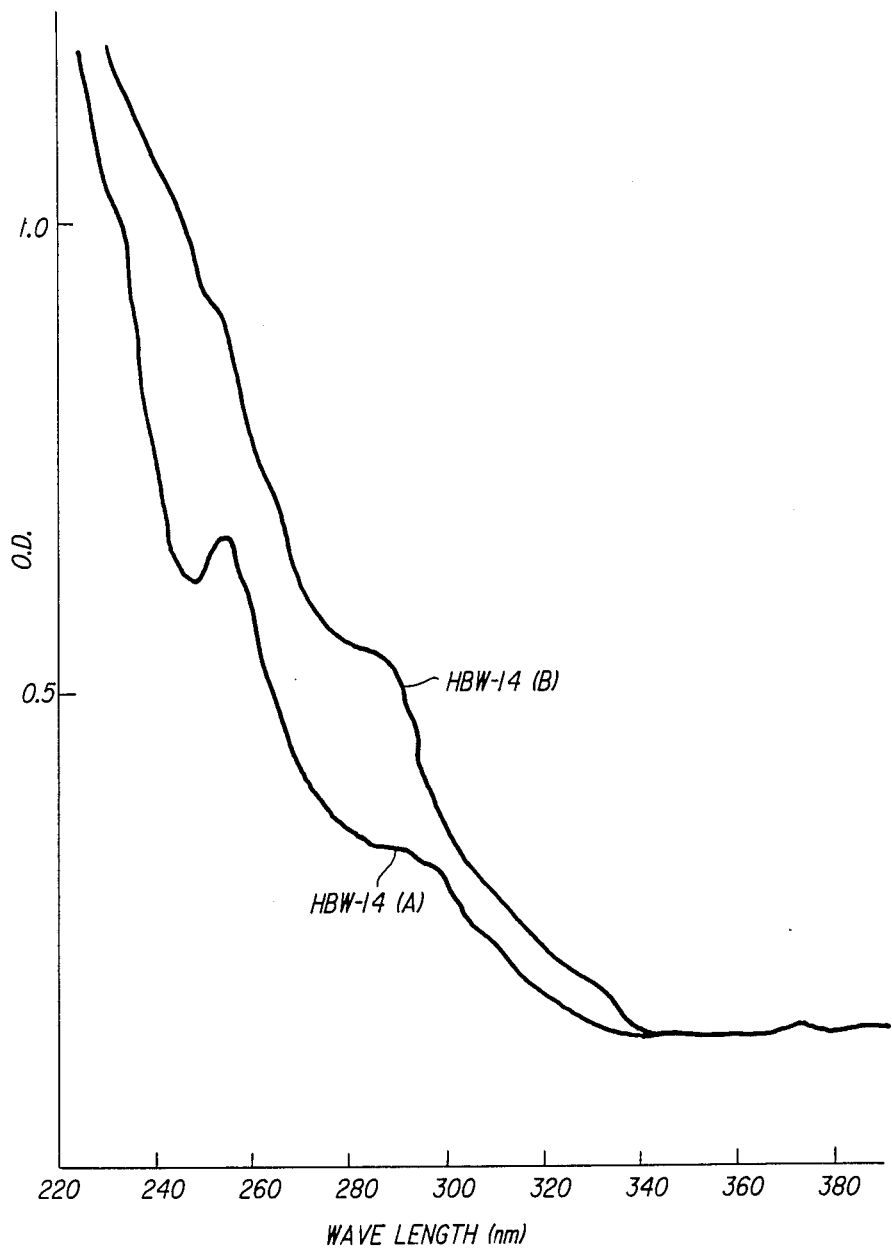
Figure 26:
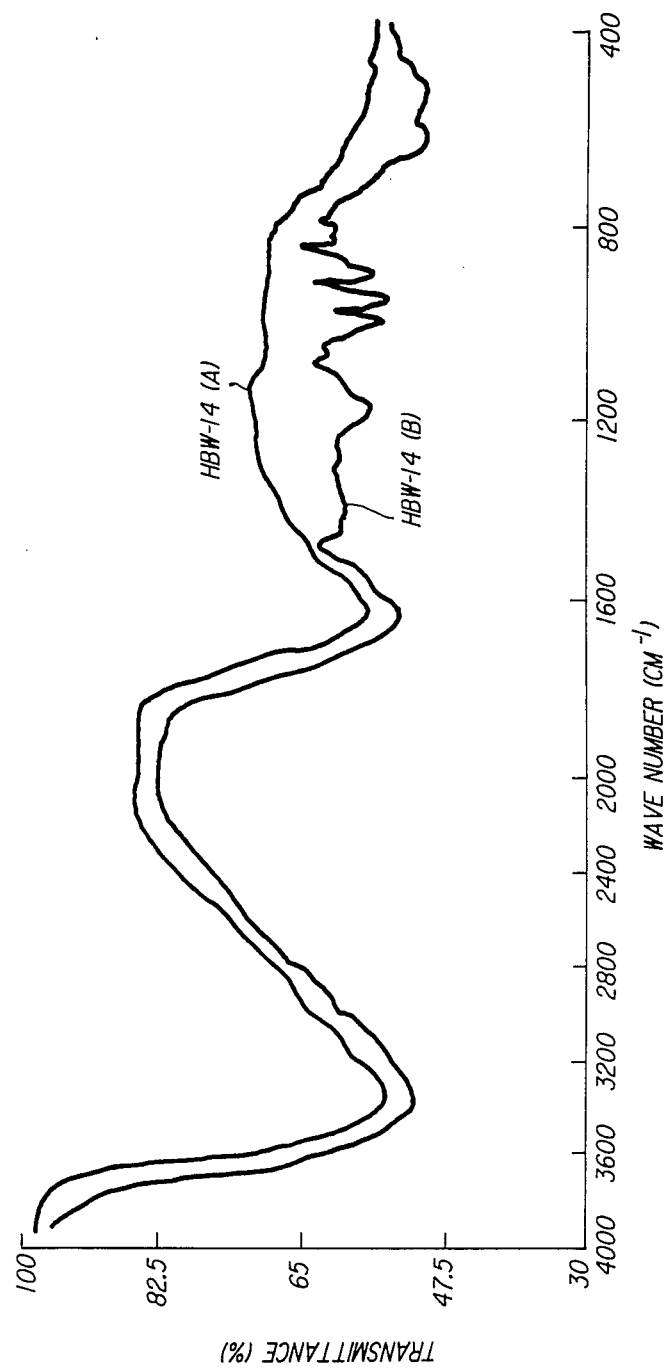
Figure 27:
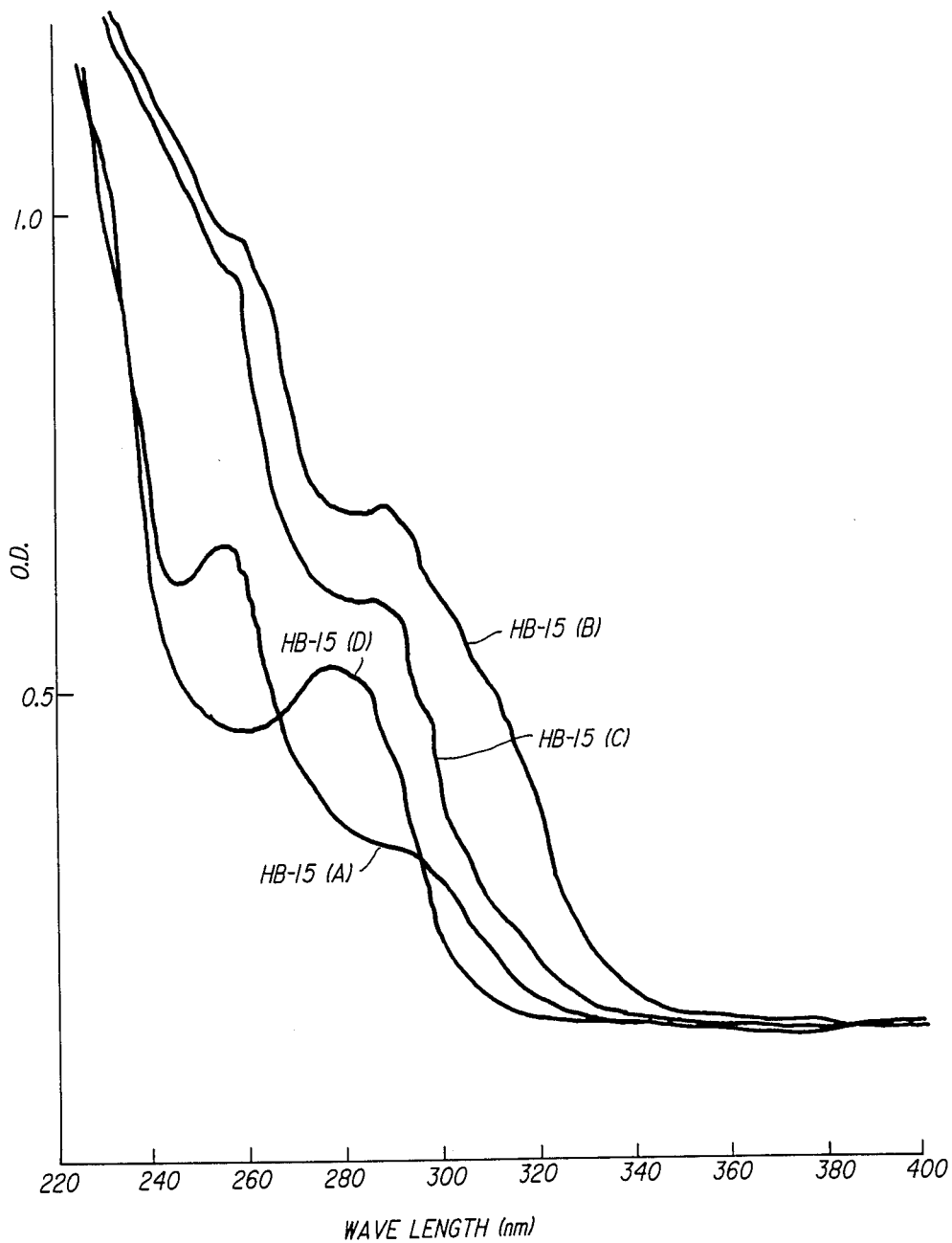
Figure 28:
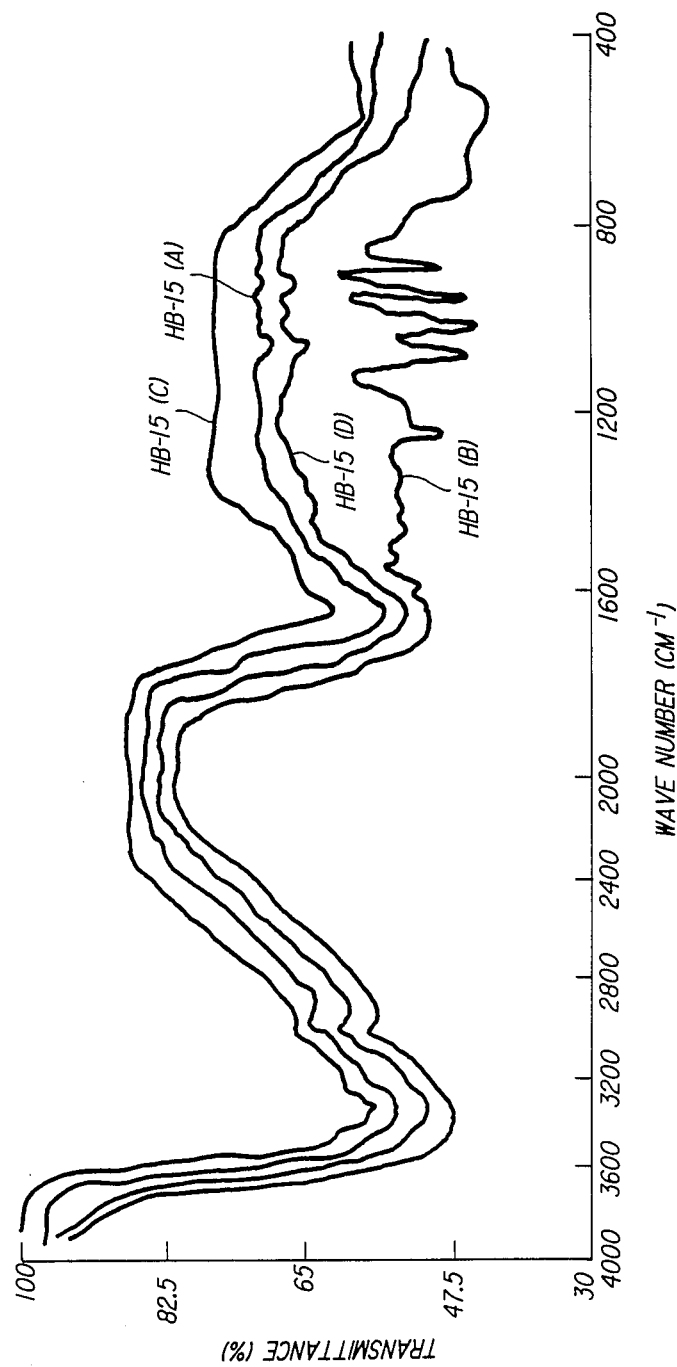
Figure 29:
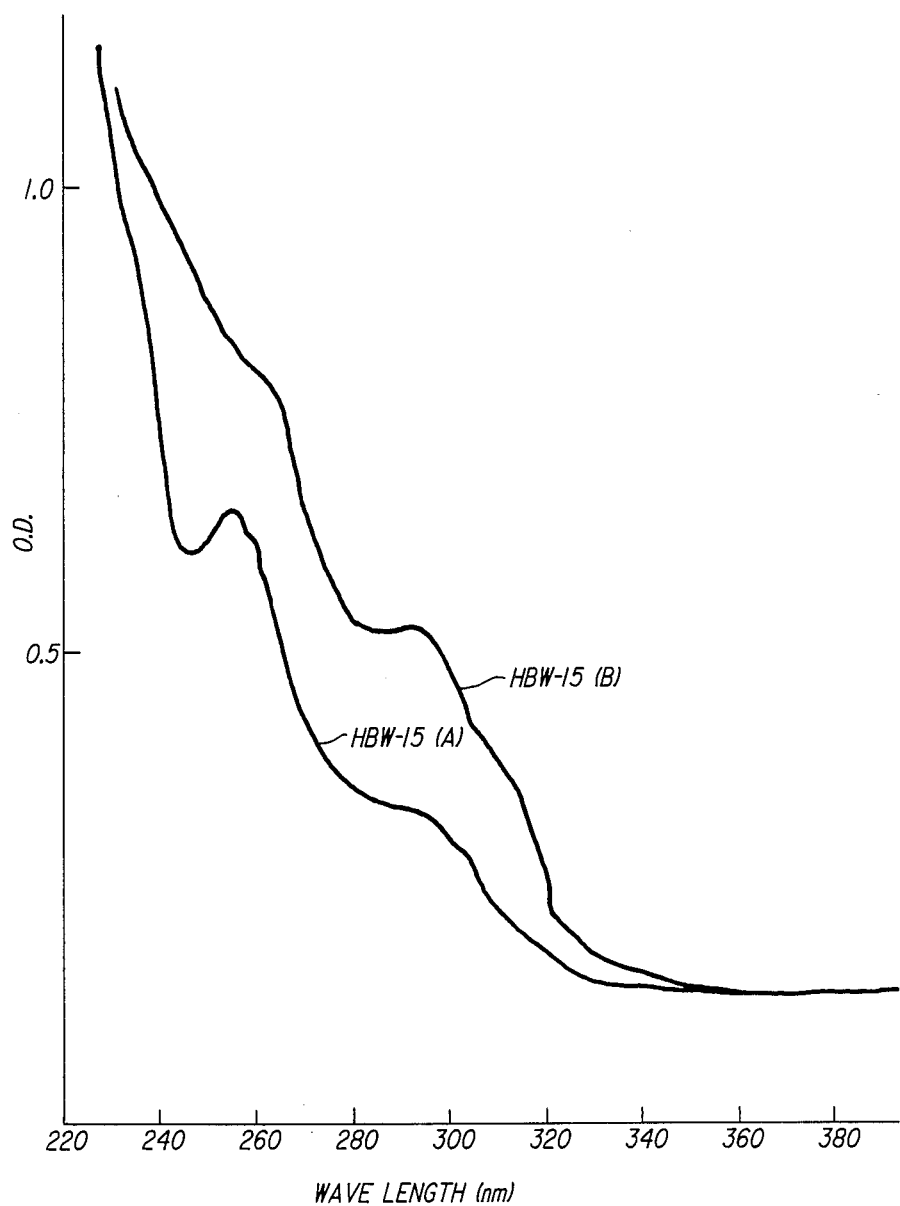
Figure 30:
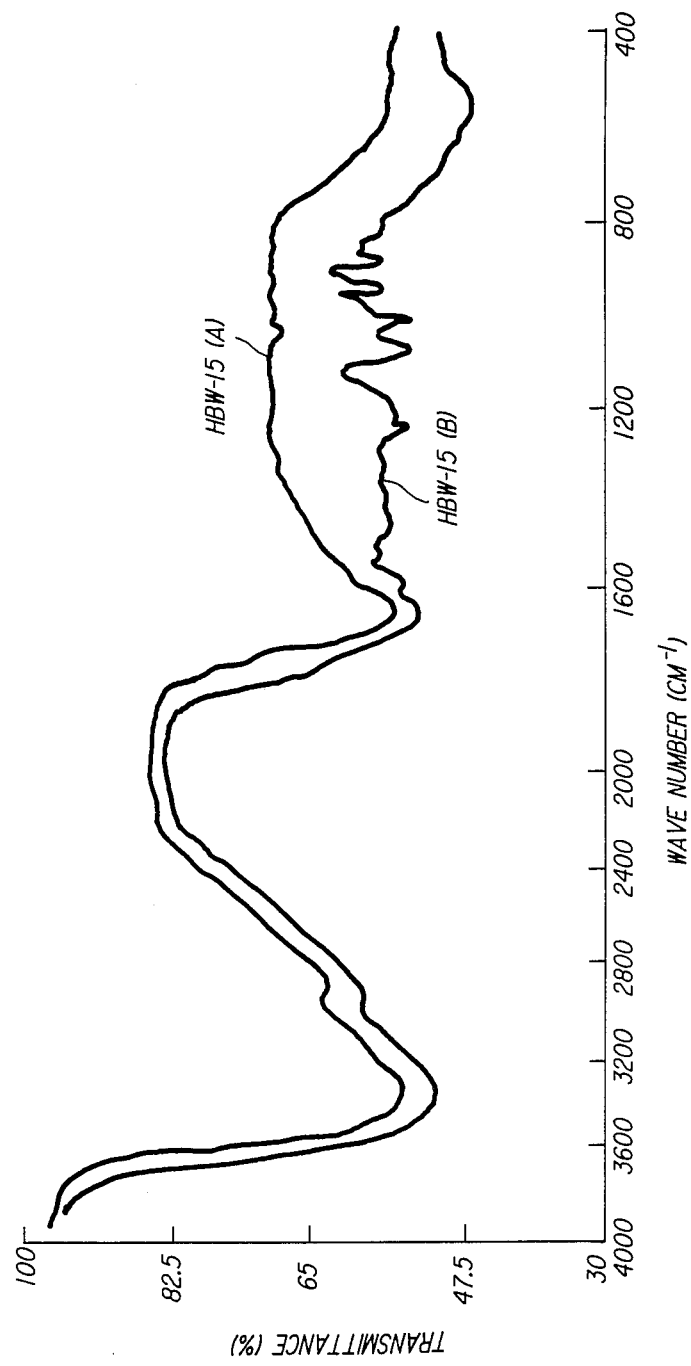
Figure 31:
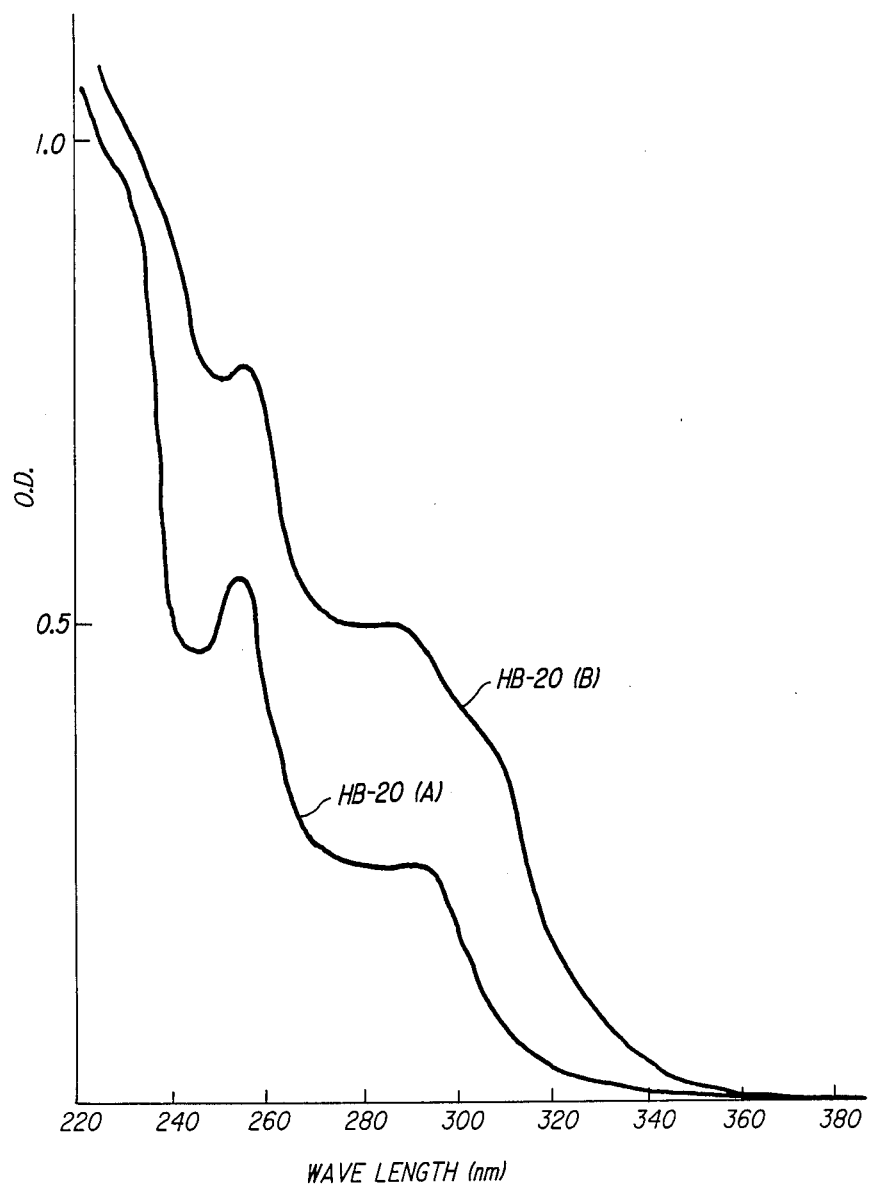
Figure 32:
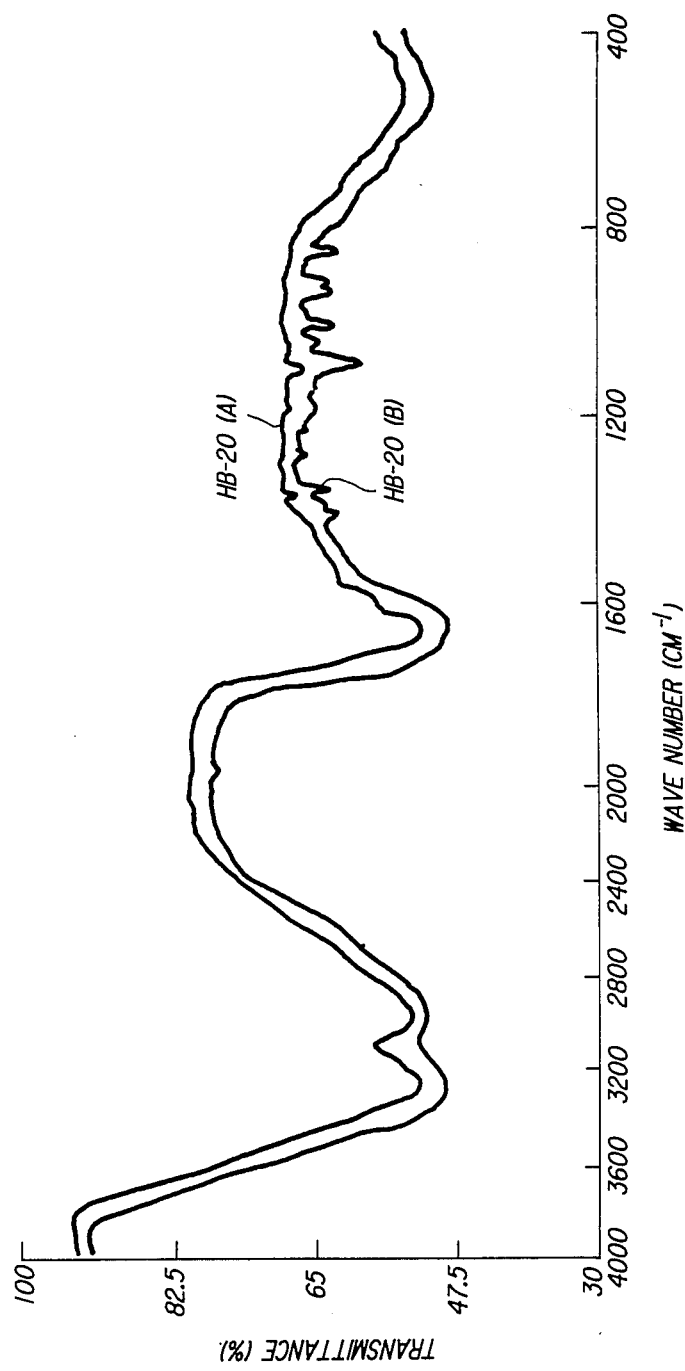
Figure 33:
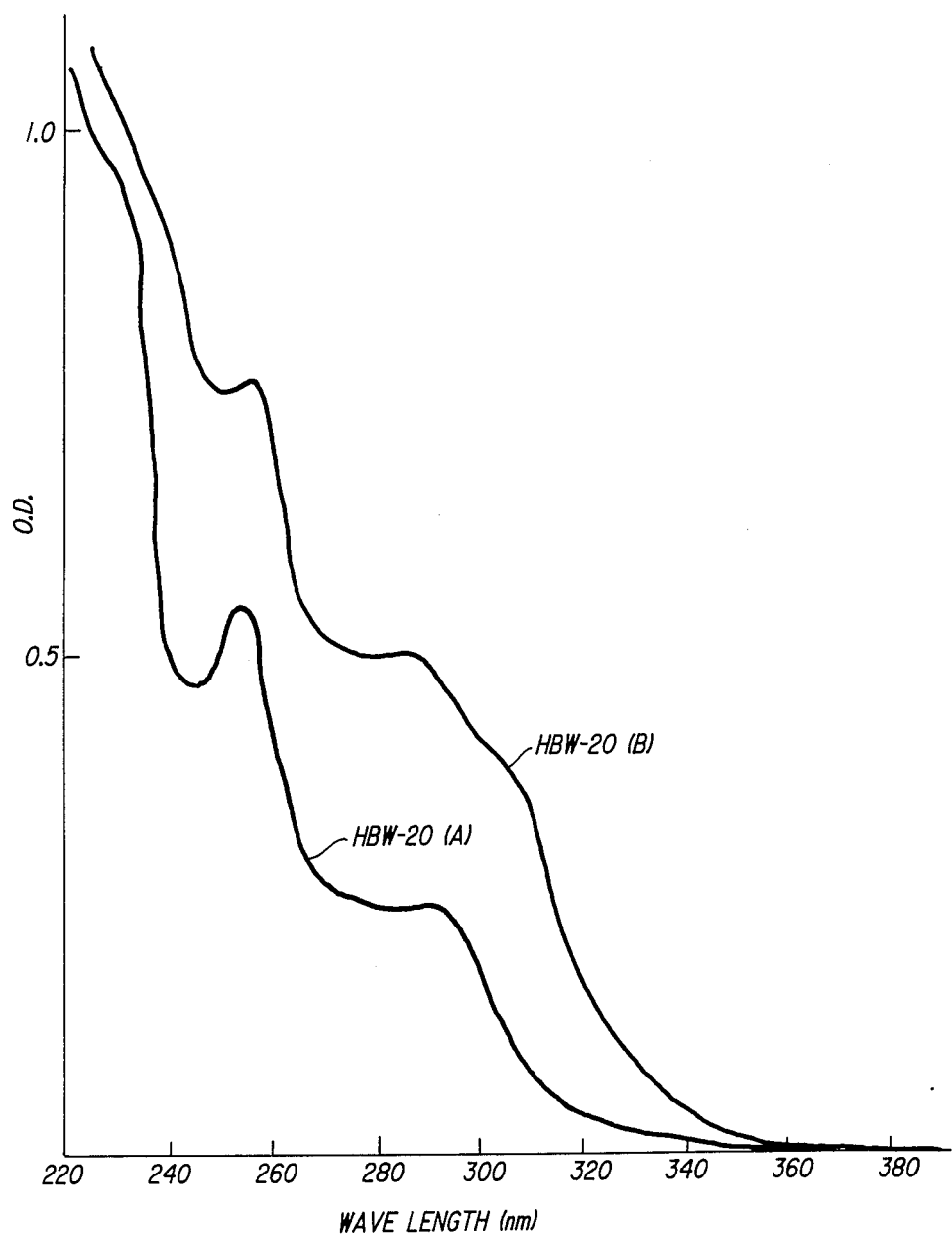
Figure 34:
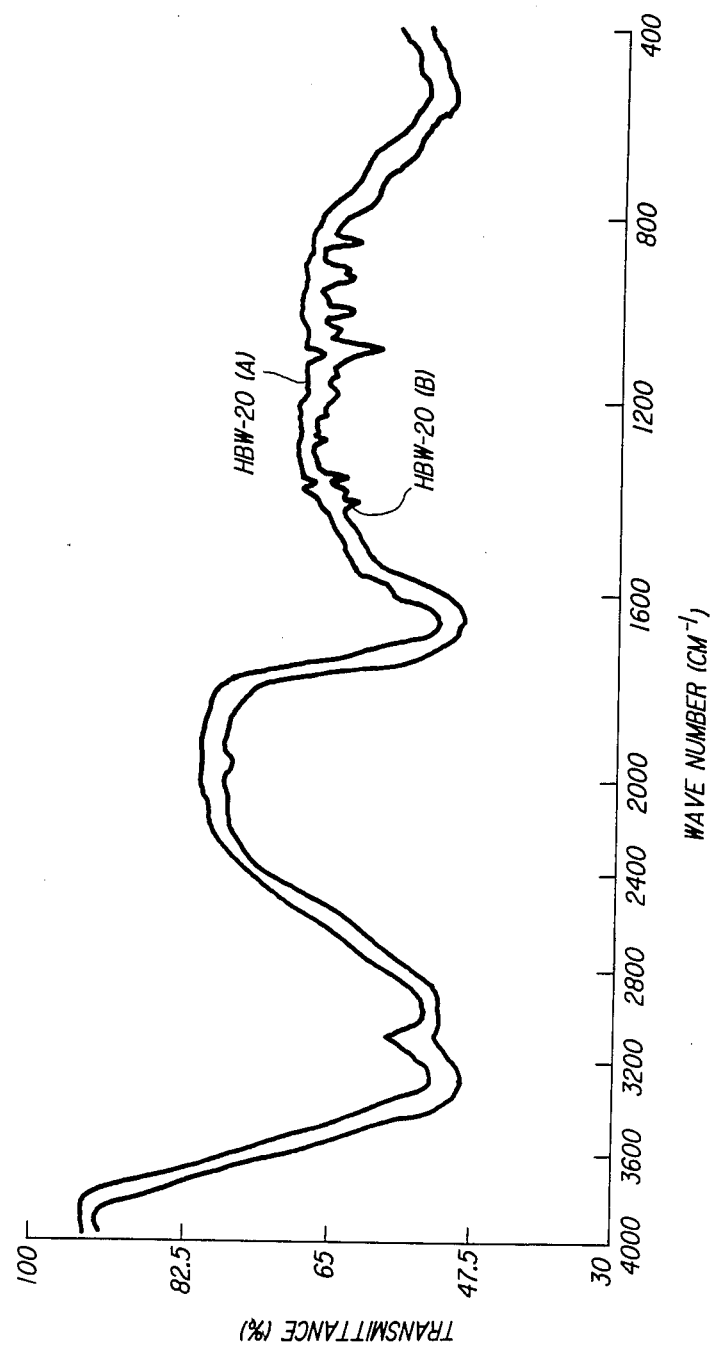
Figure 35:
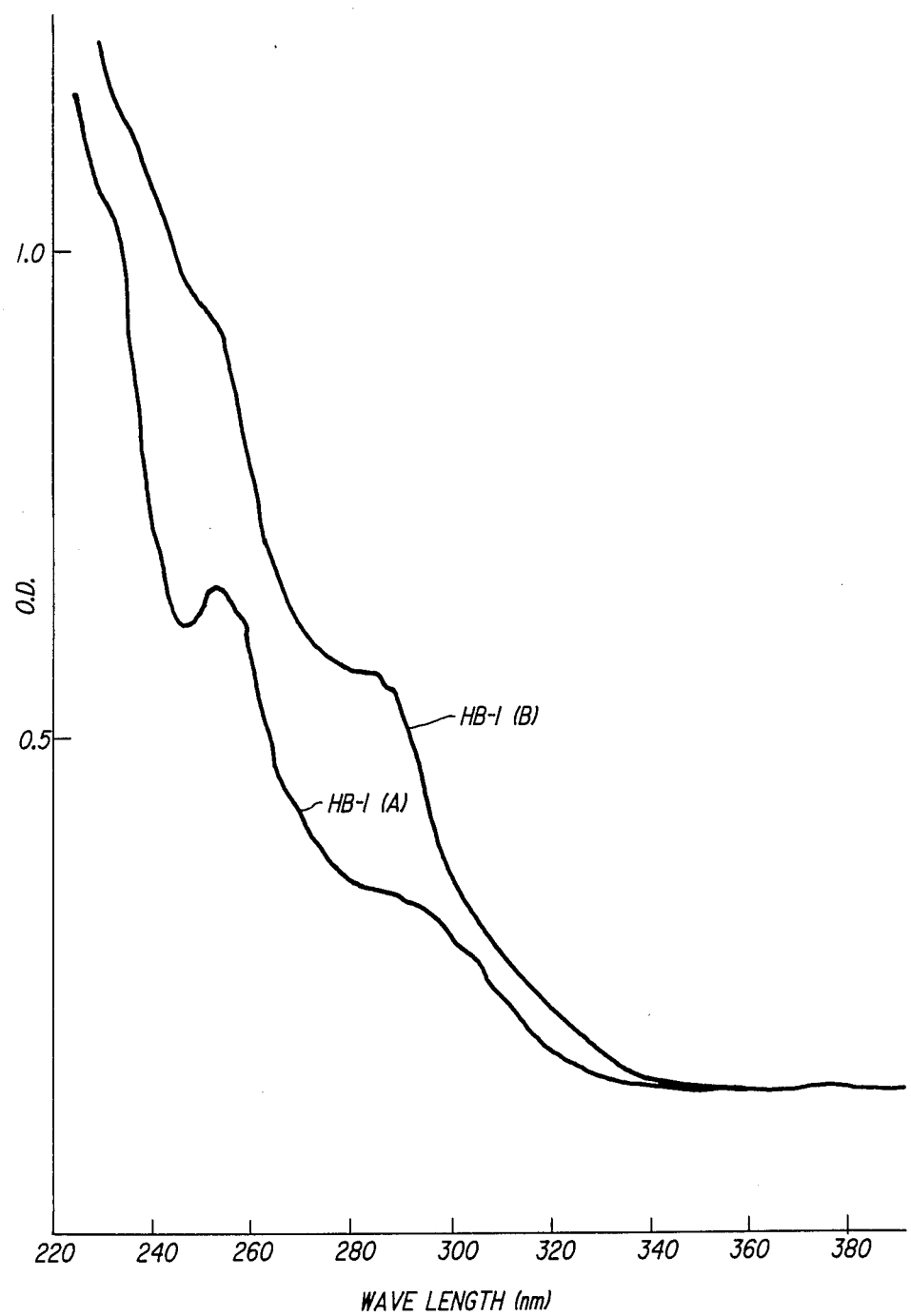
Figure 36:
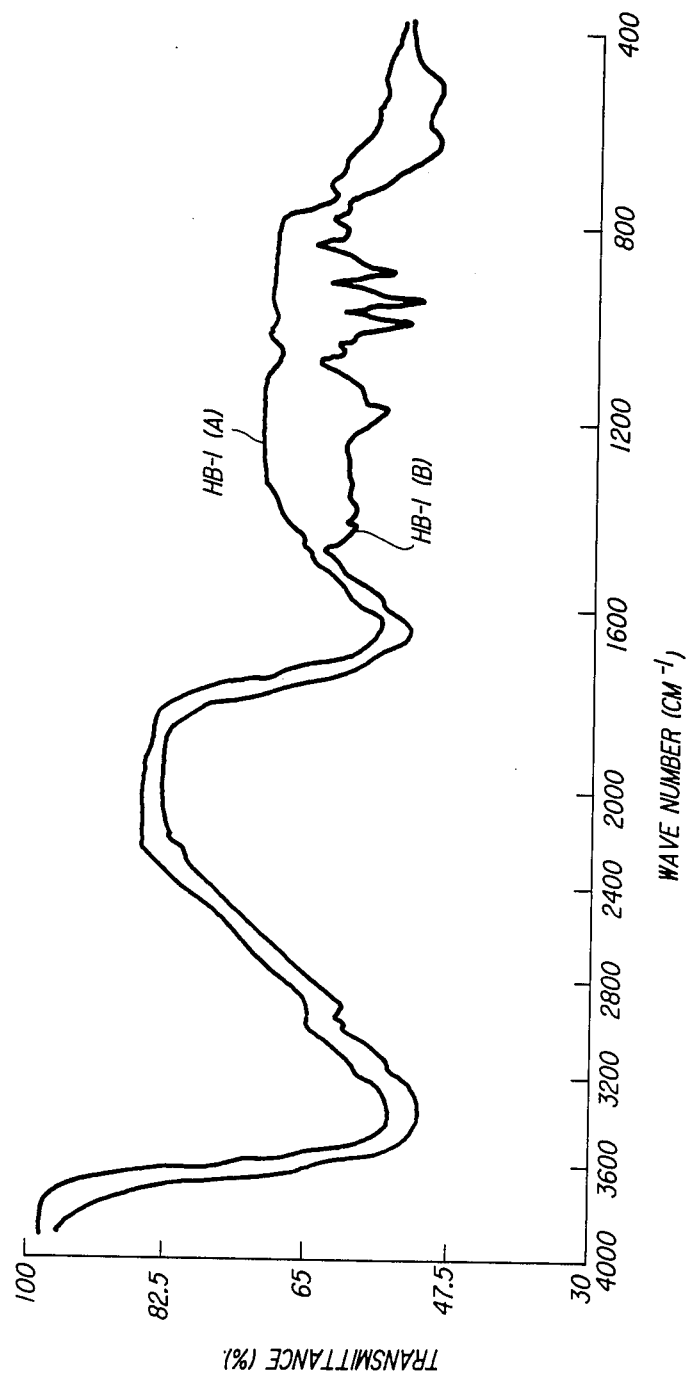
Figure 37:
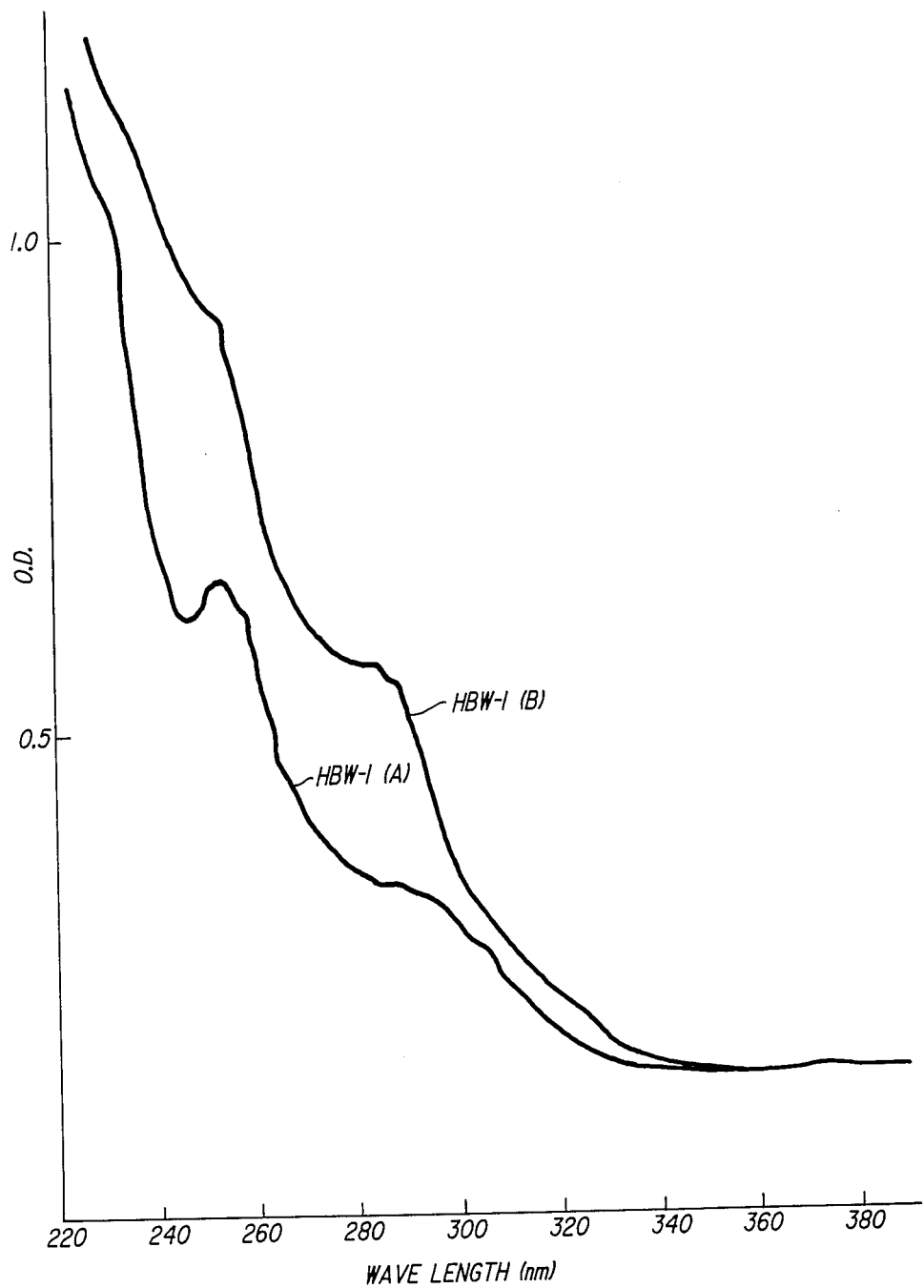
Figure 38:
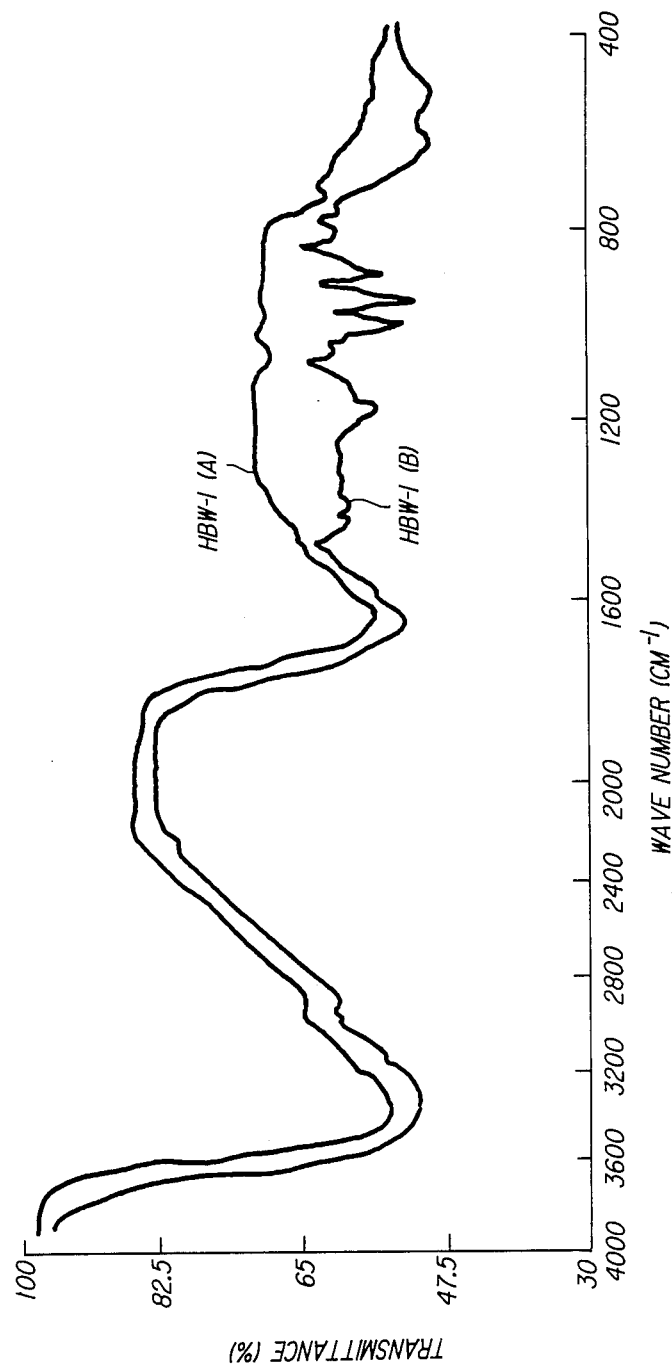
Figure 39:
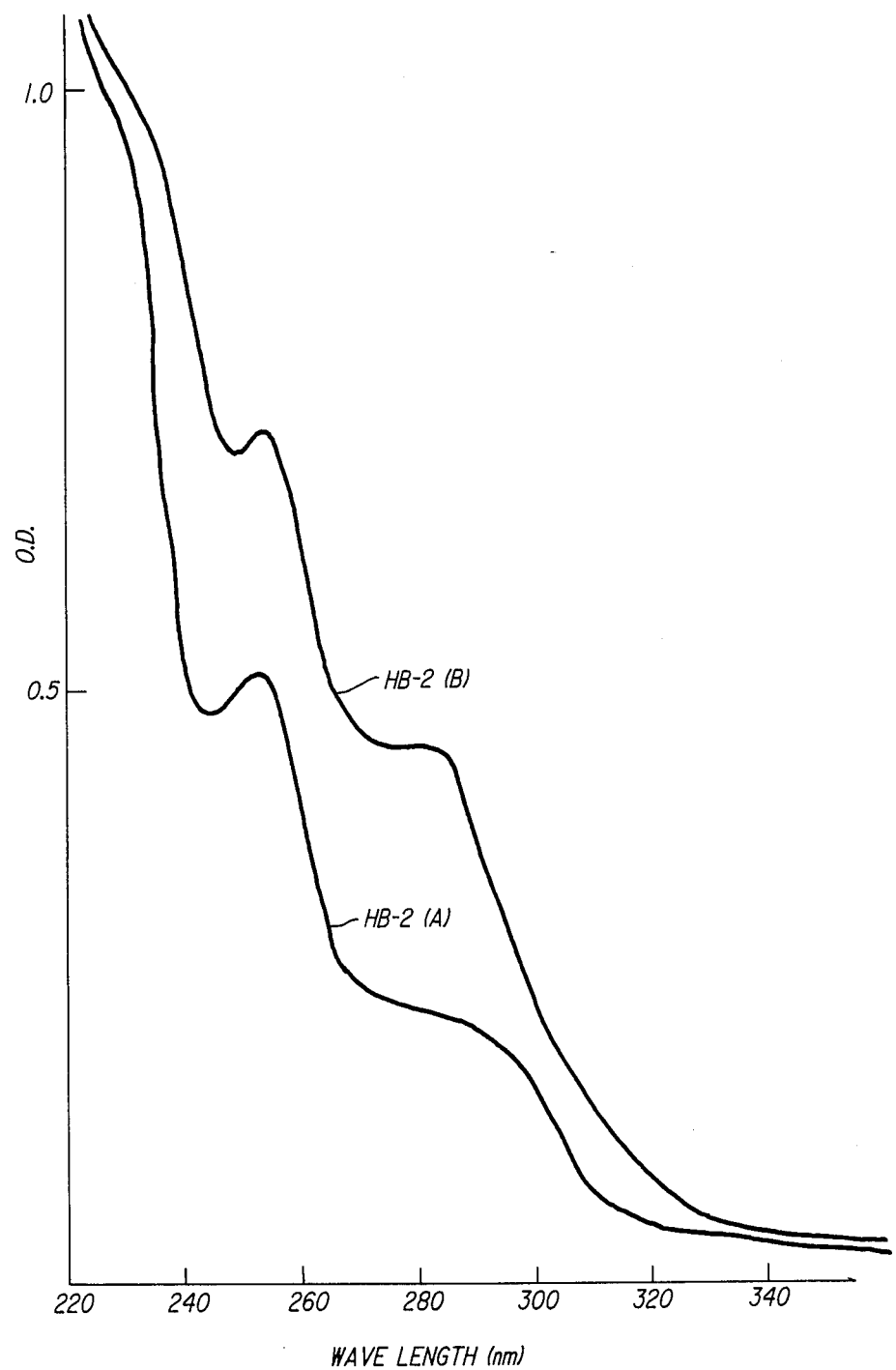
Figure 40:
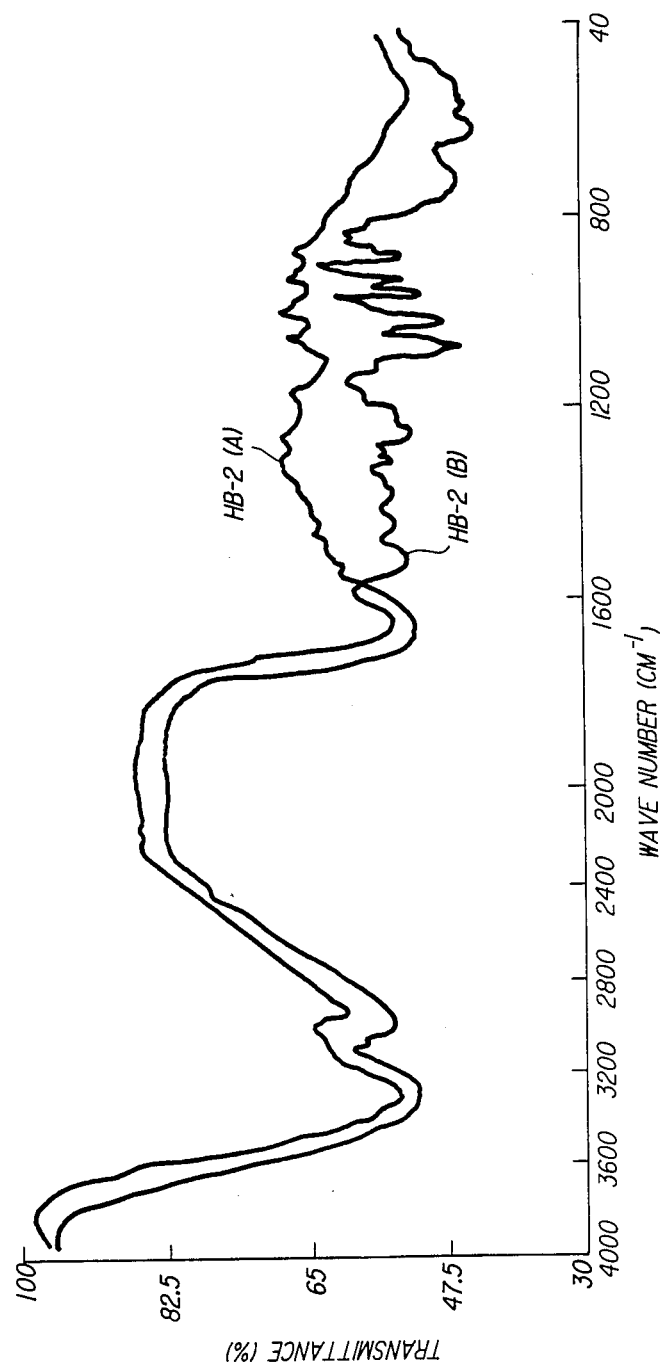
Figure 41:
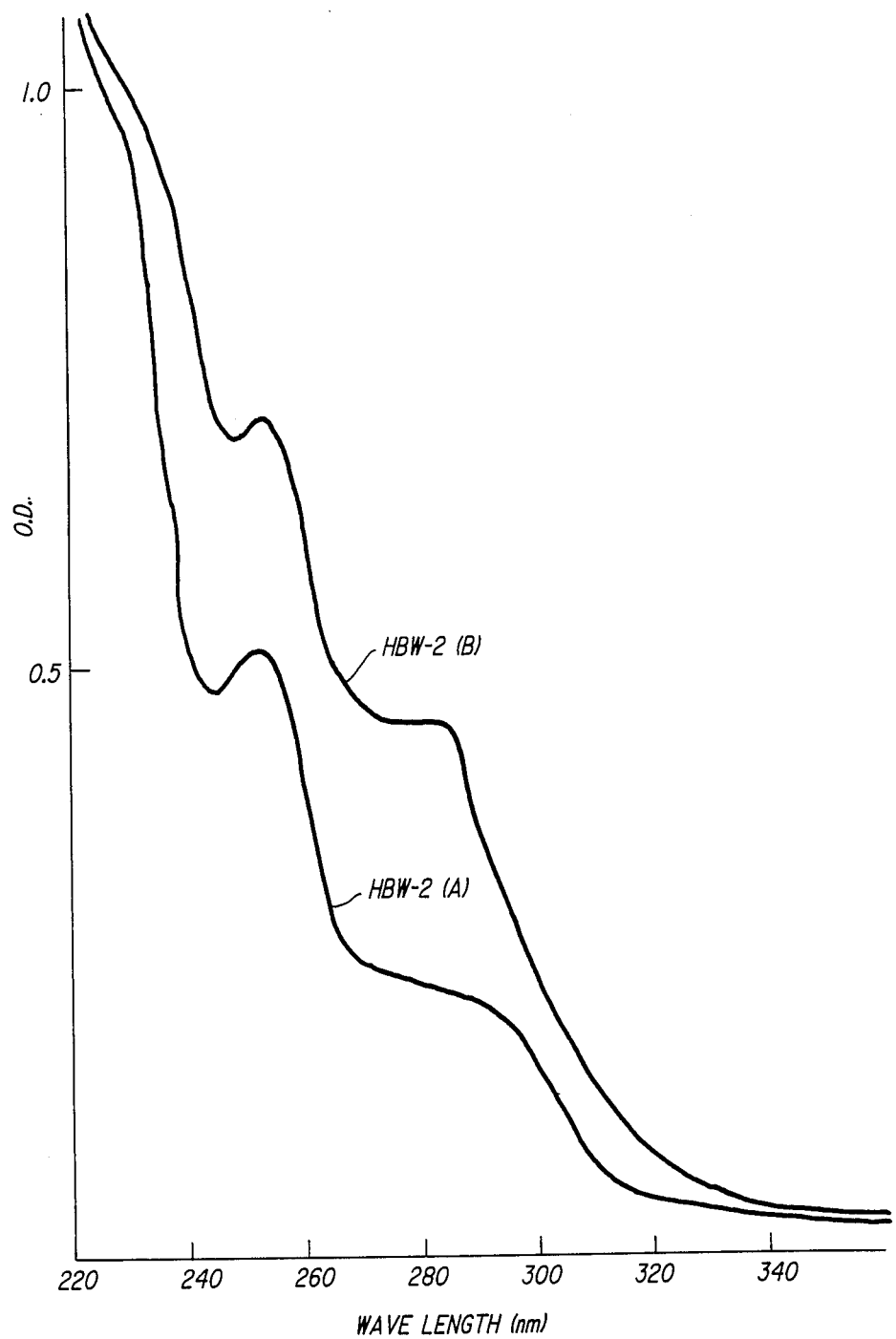
Figure 42:
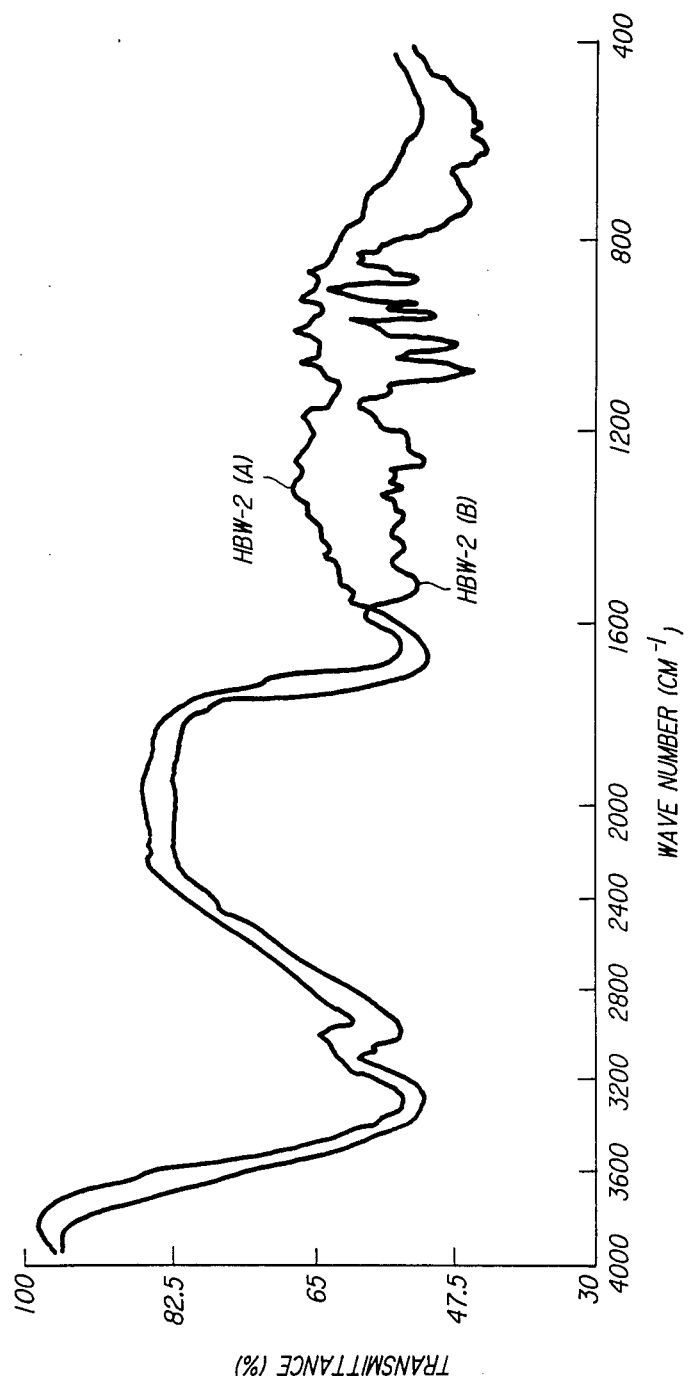
Figure 43:
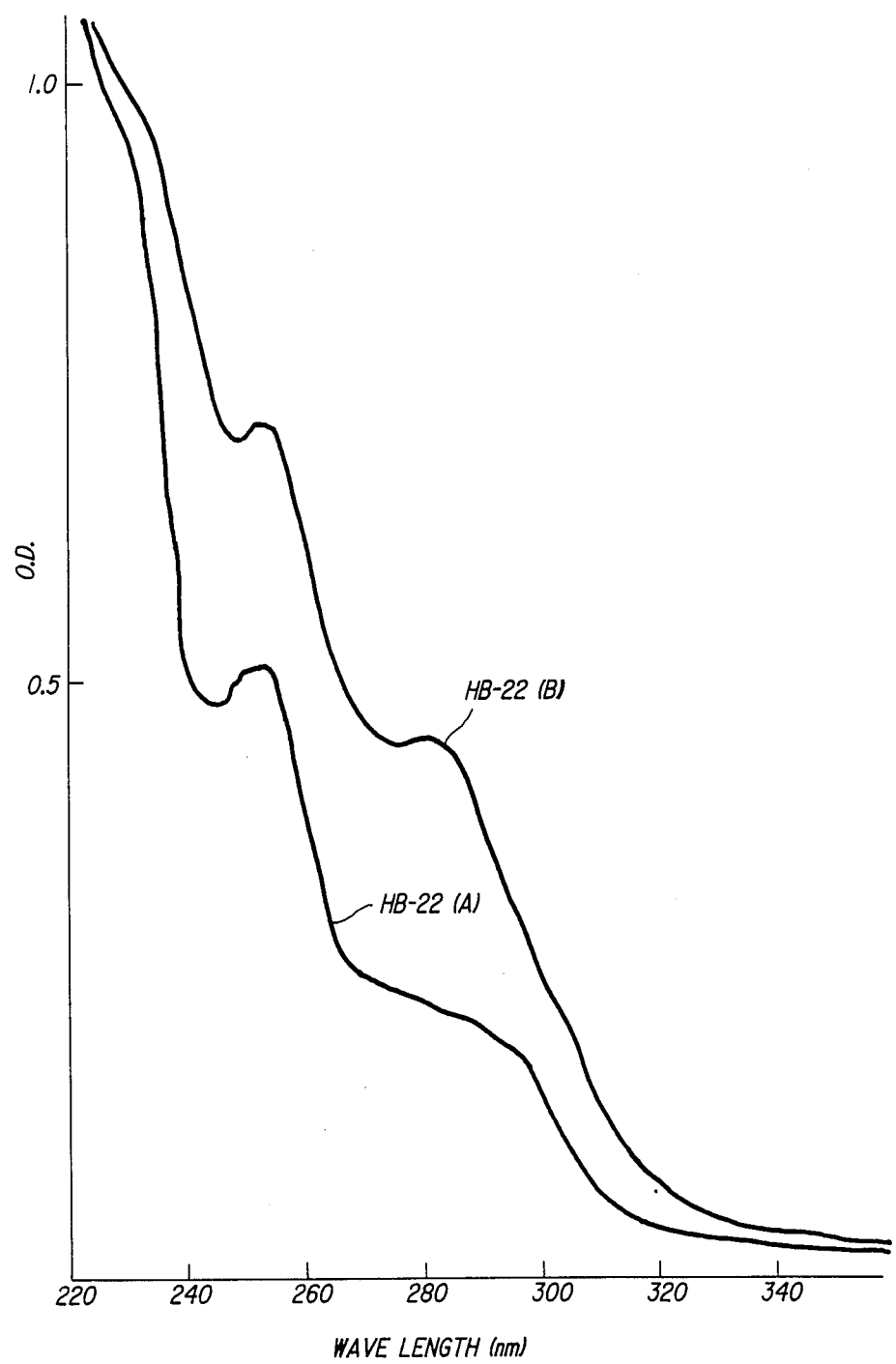
Figure 44:
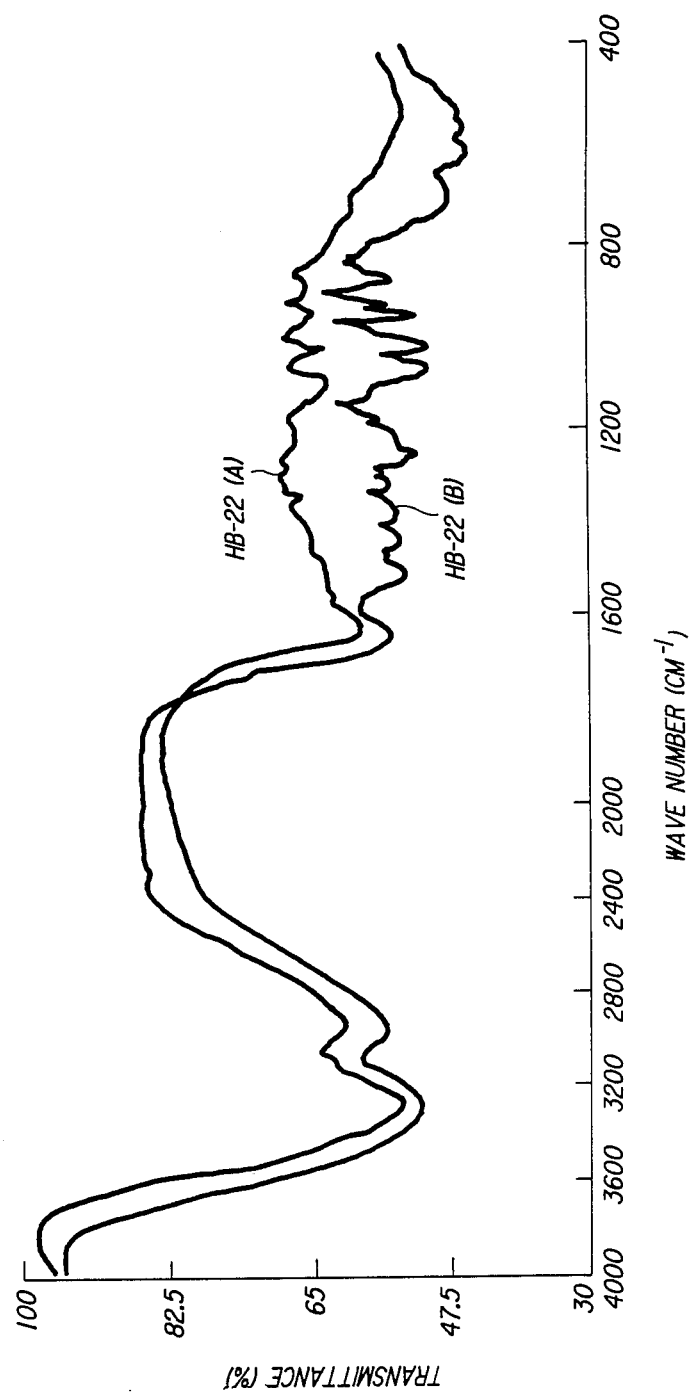
Figure 45:
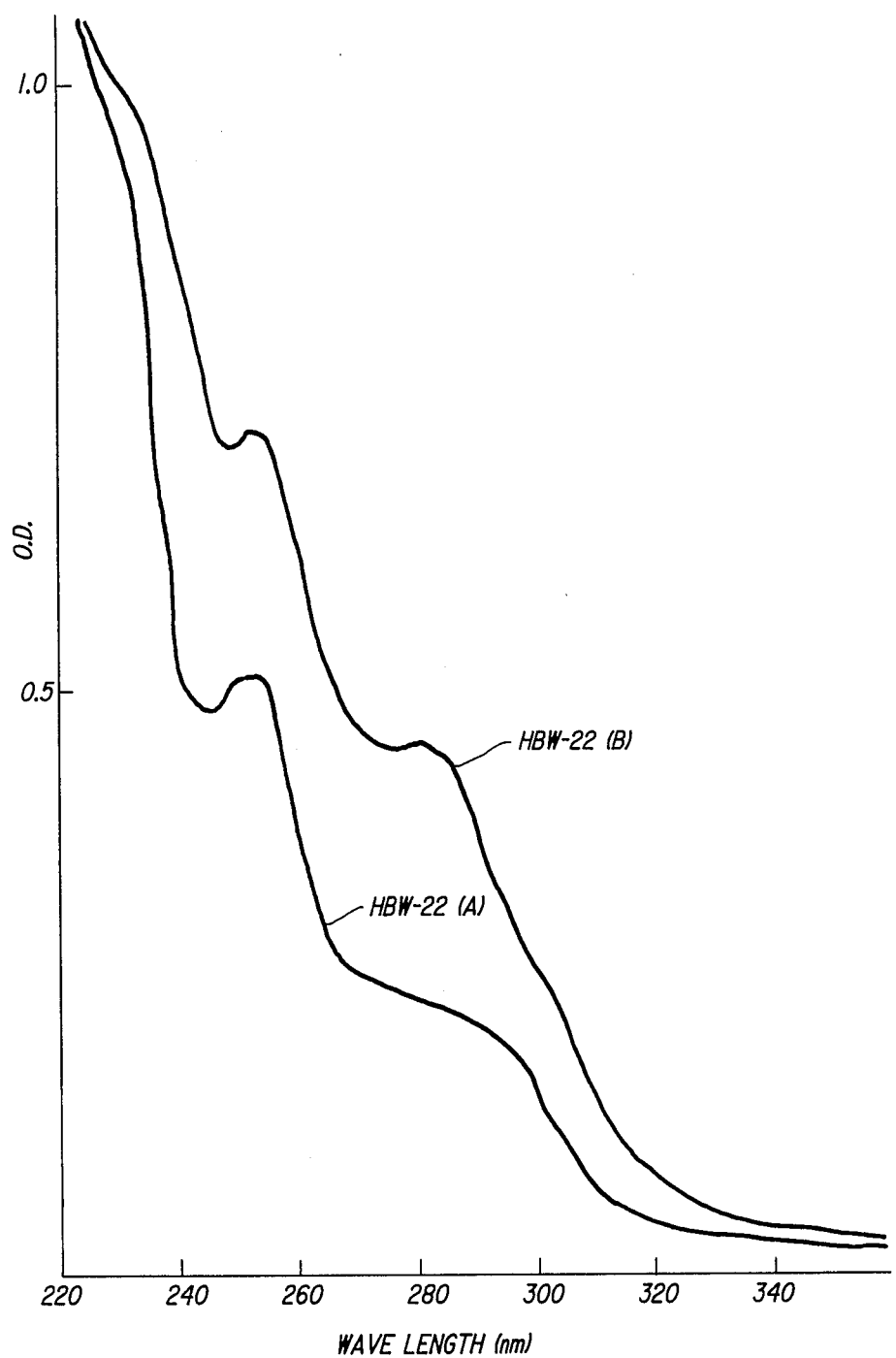
Figure 46:
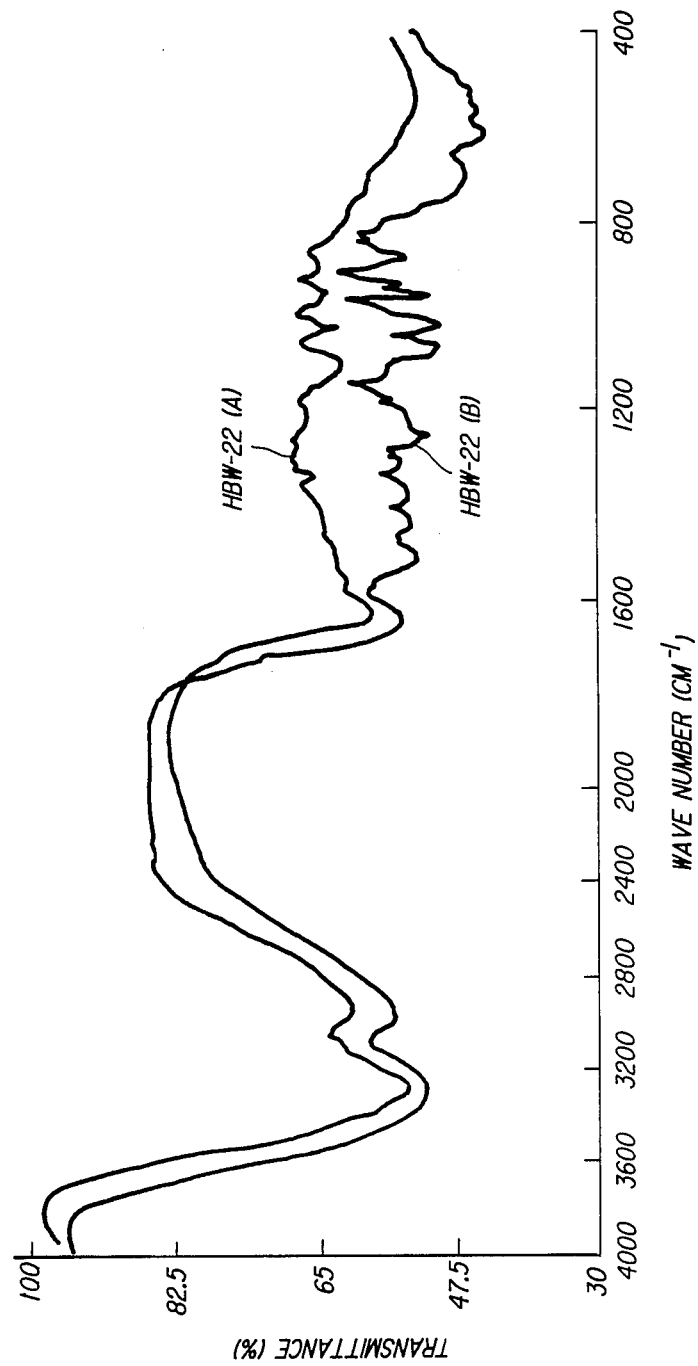
Figure 47:
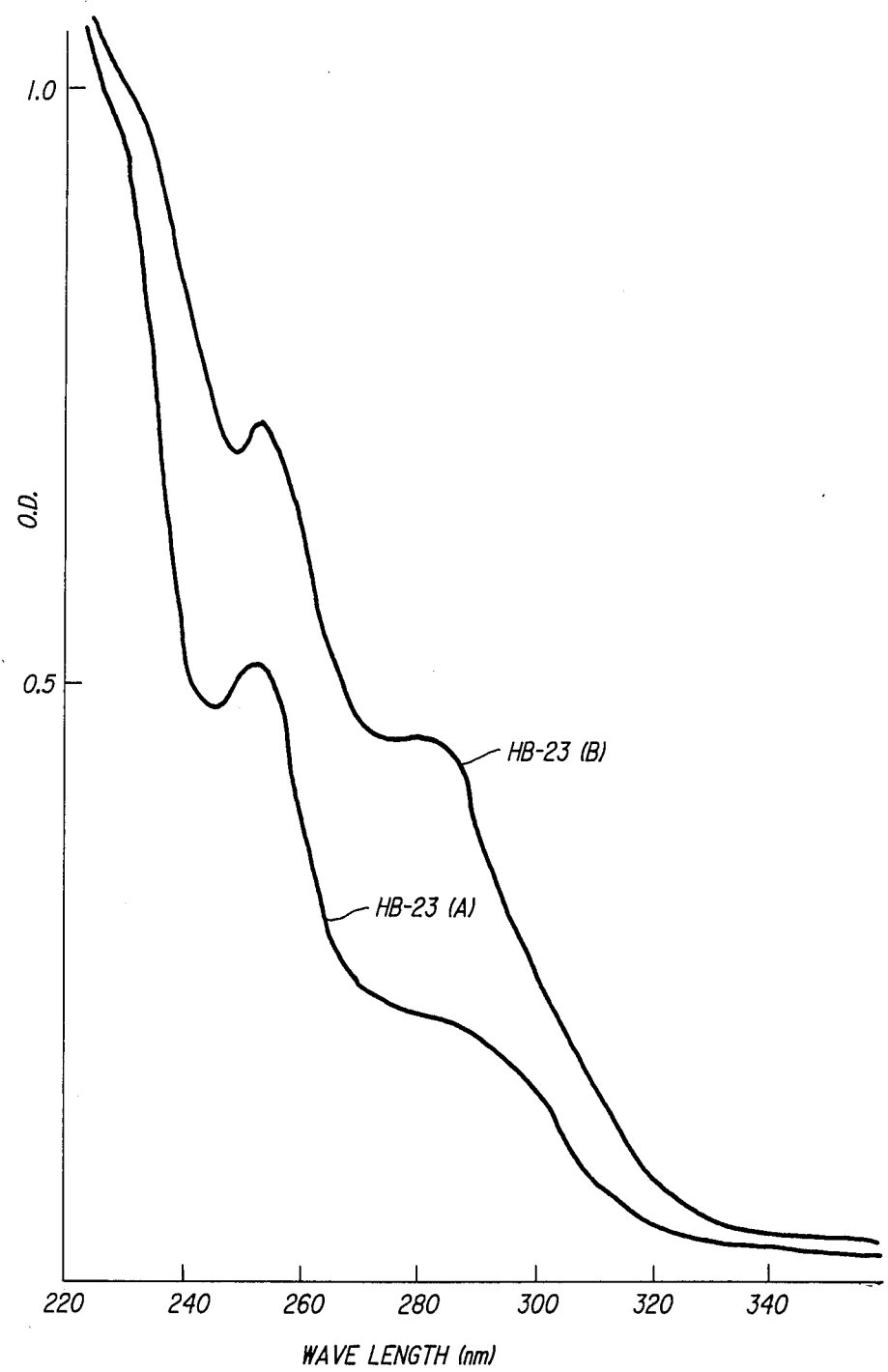
Figure 48:
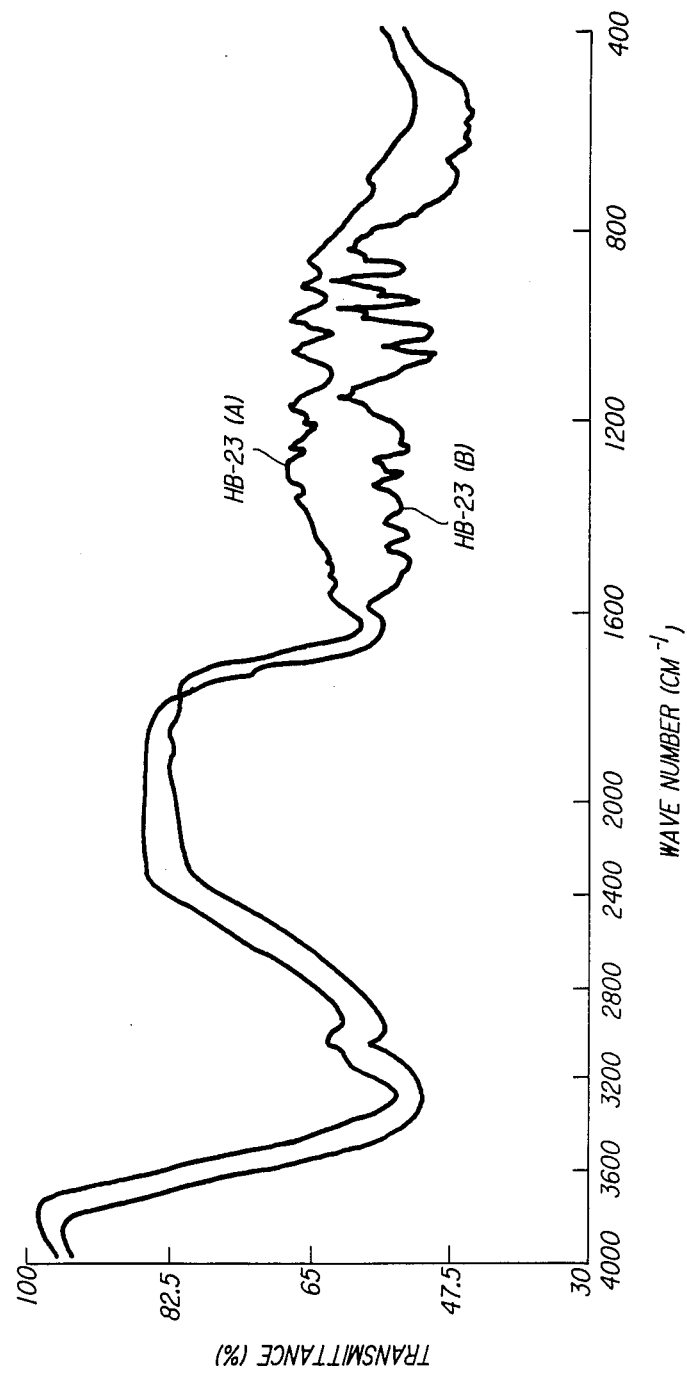
Figure 49:
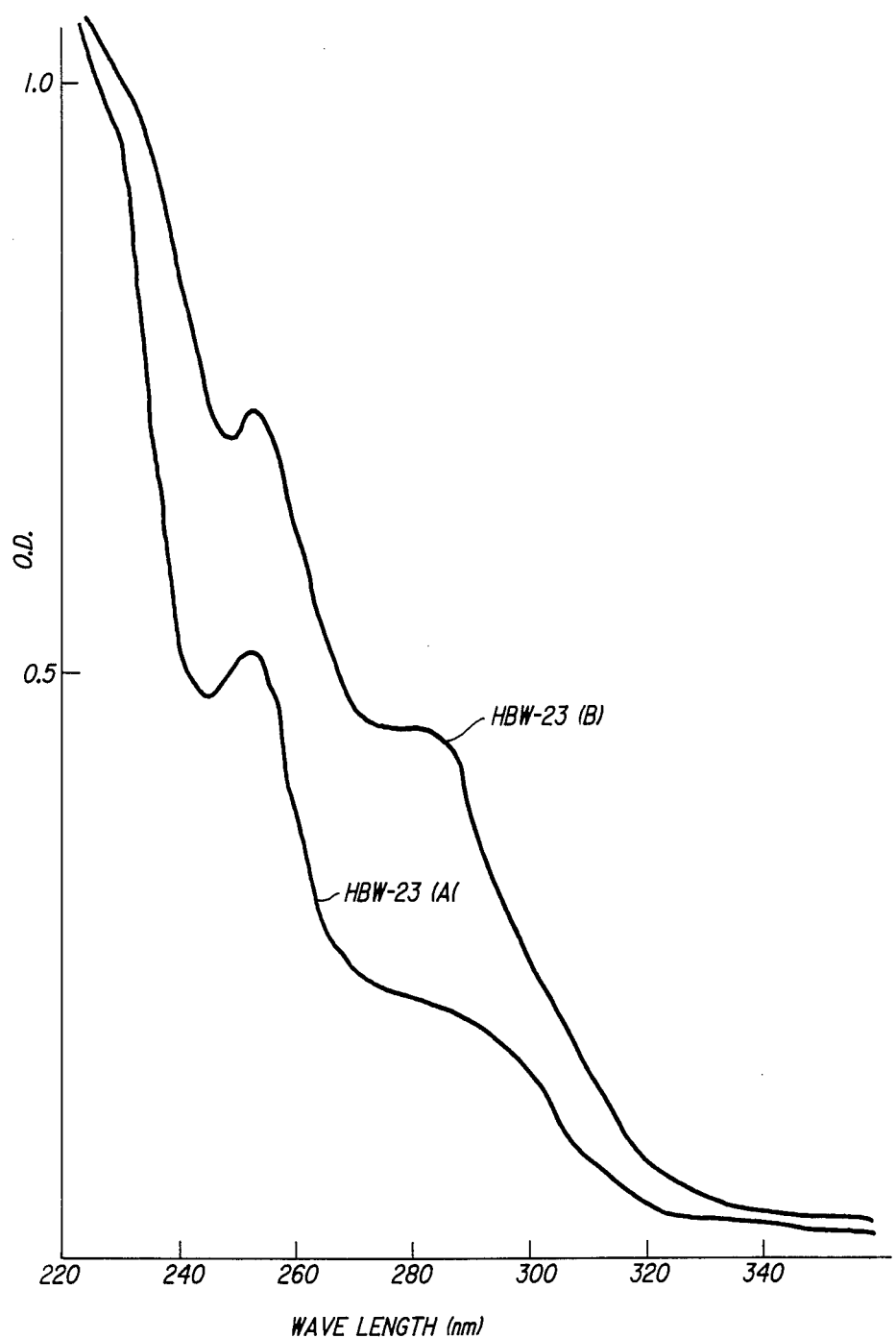
Figure 50:
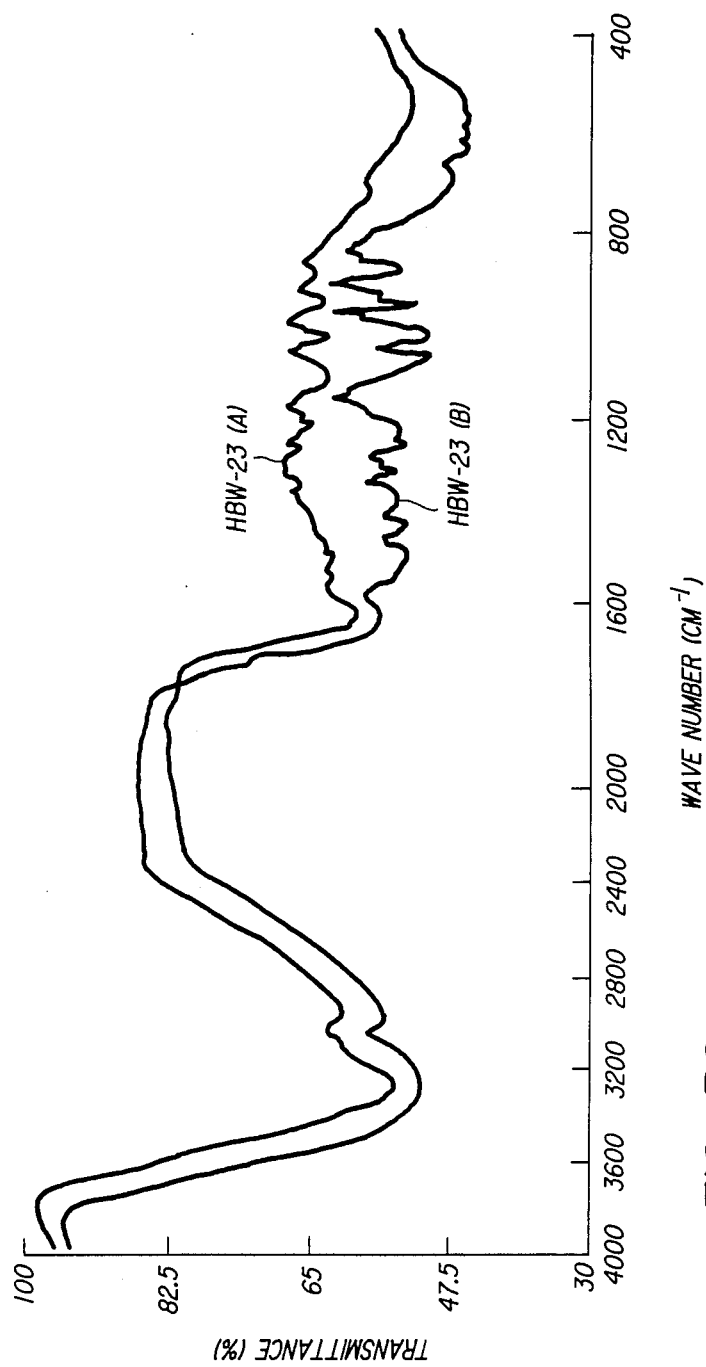
Figure 51:
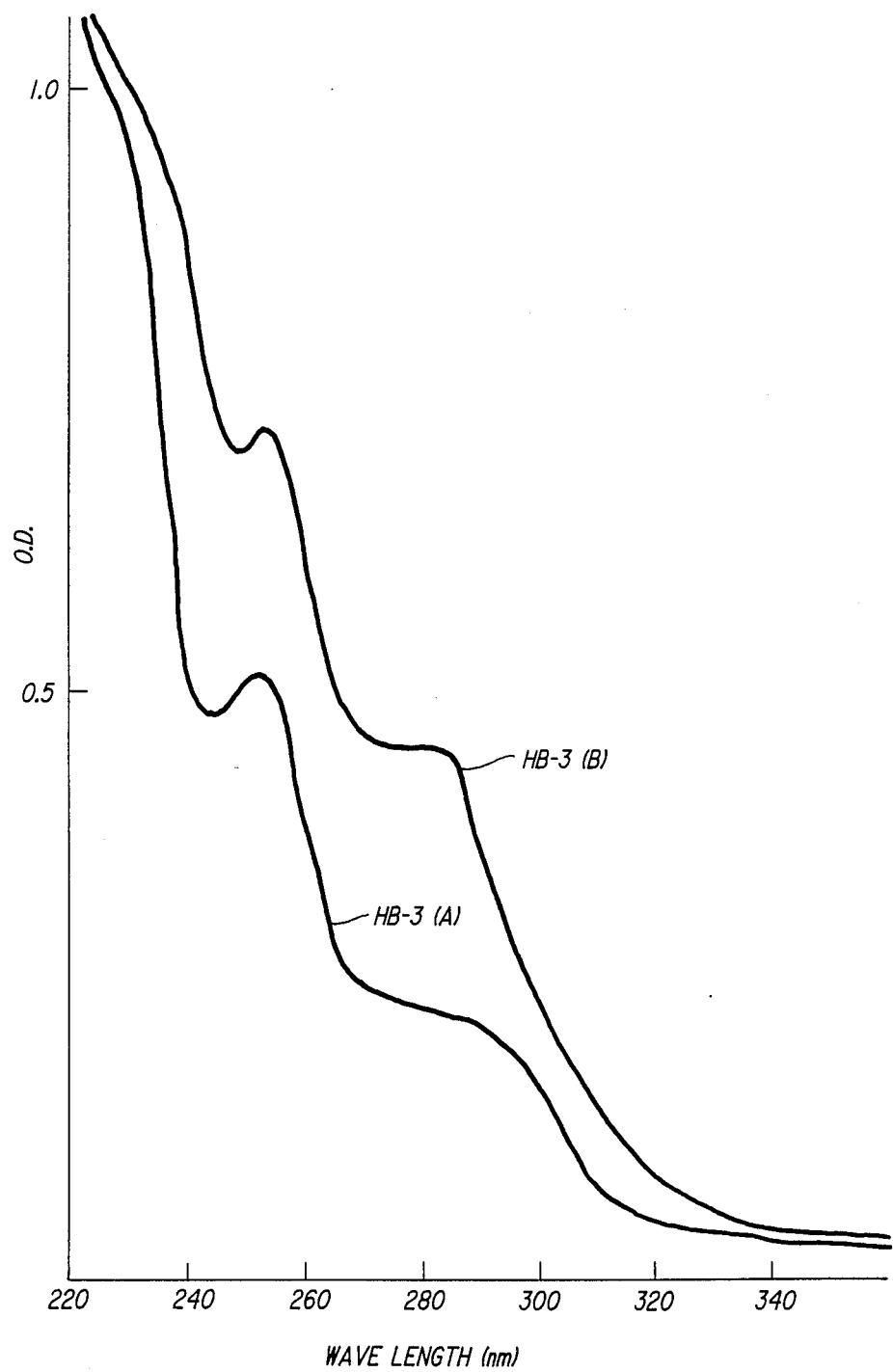
Figure 52:
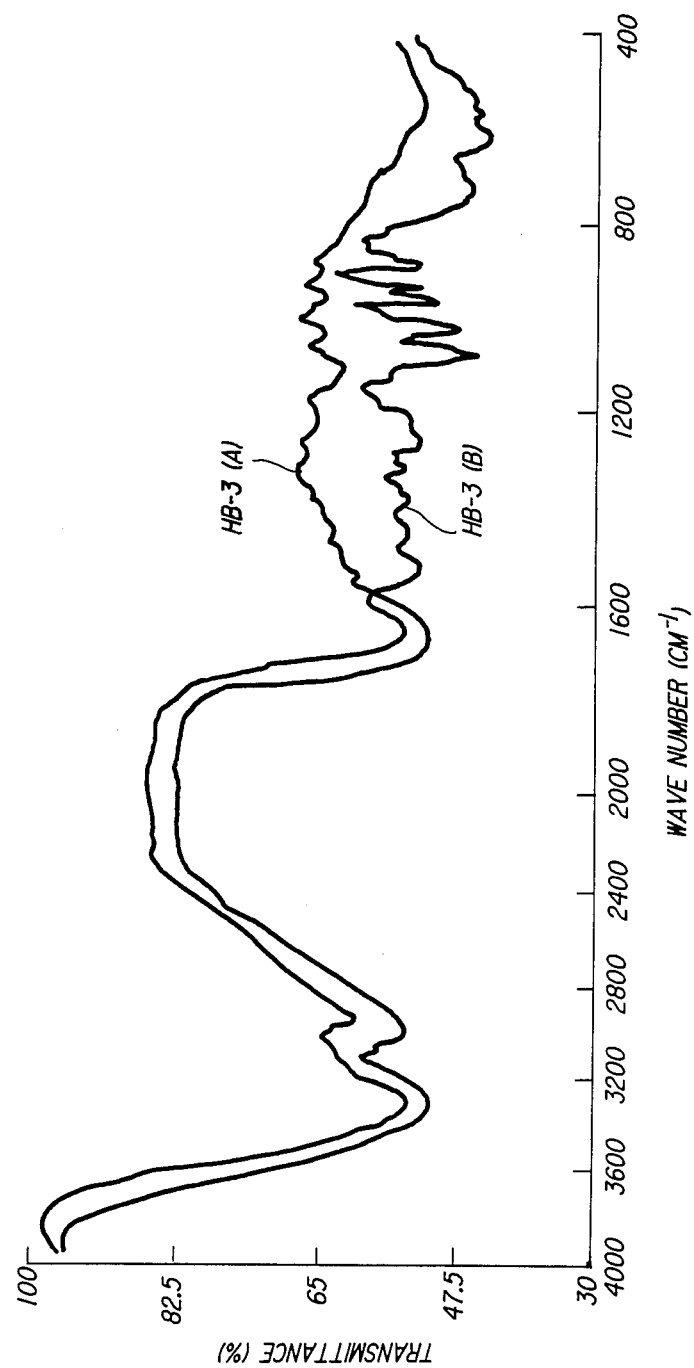
Figure 53:
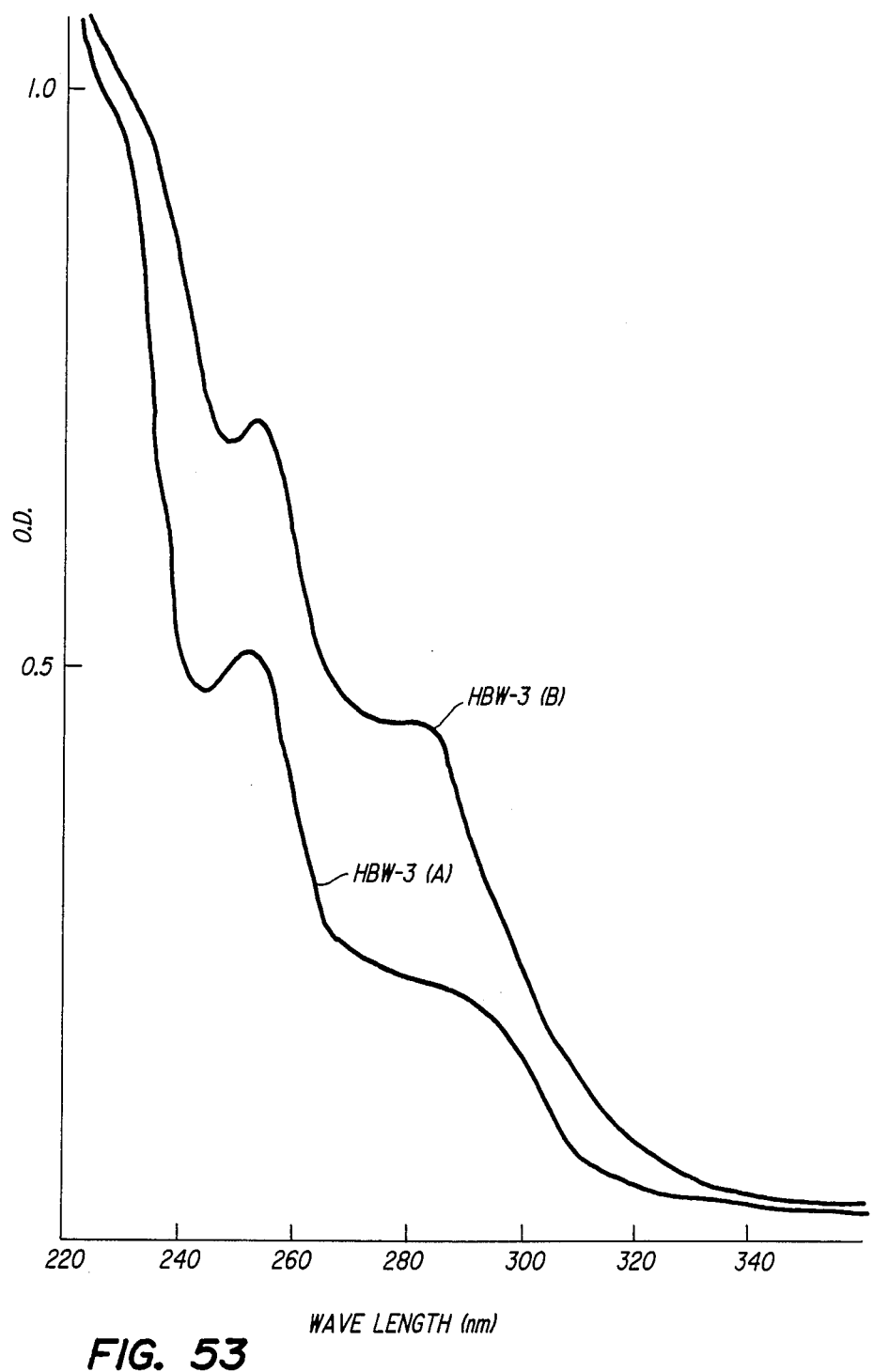
Figure 54:
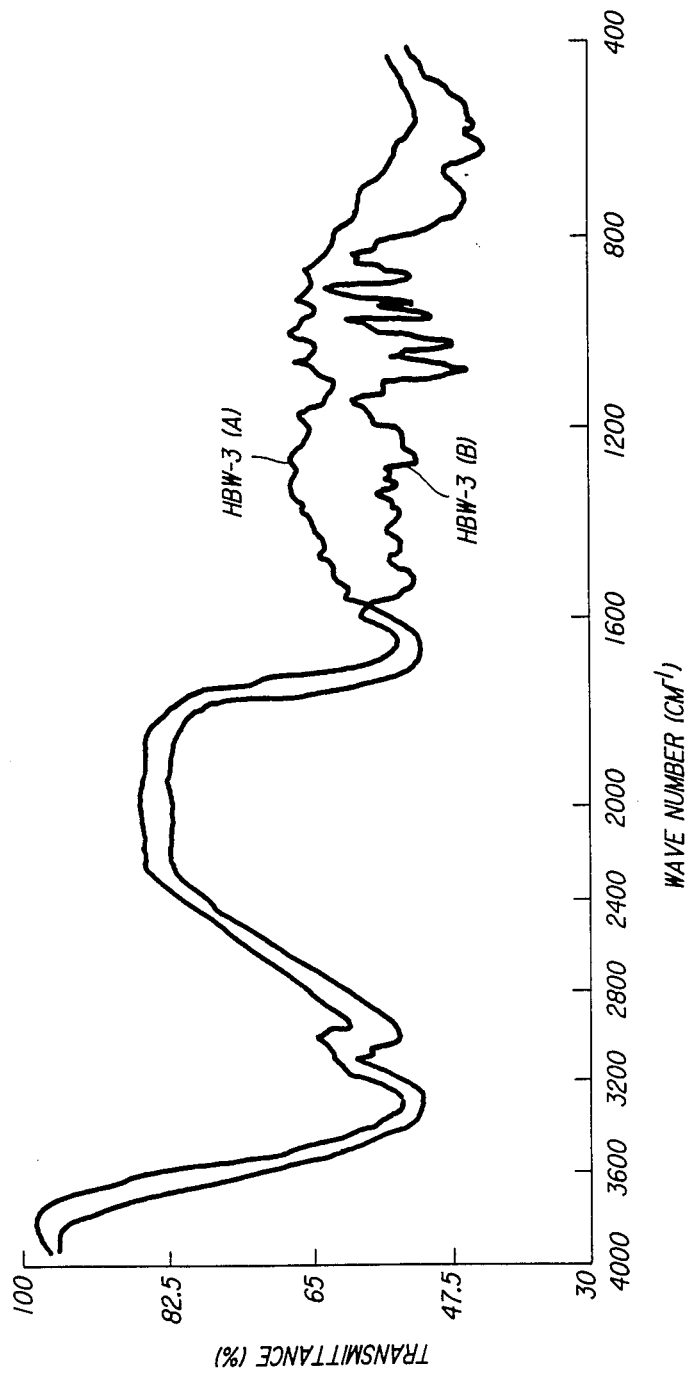
Figure 55:
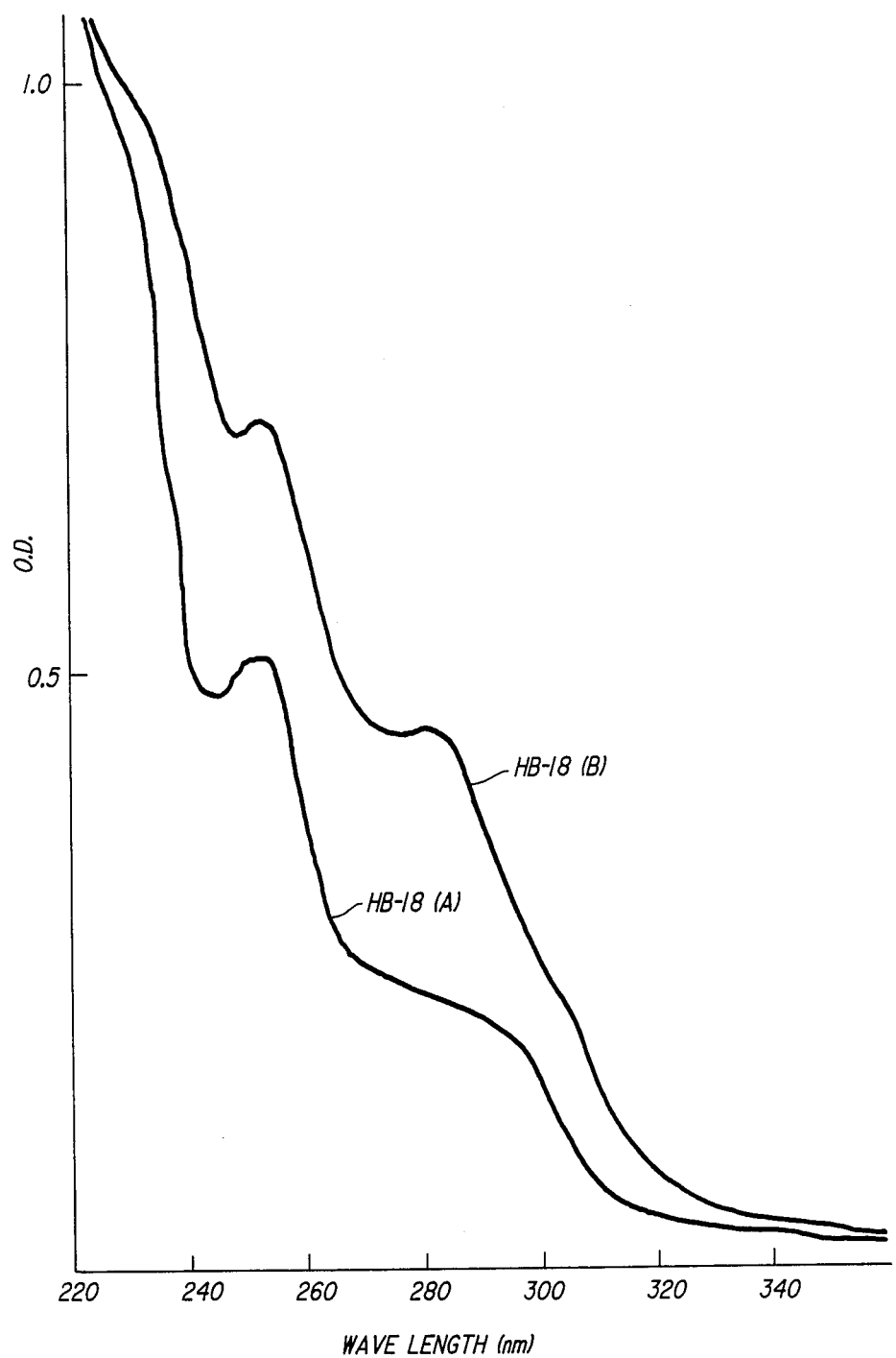
Figure 56:
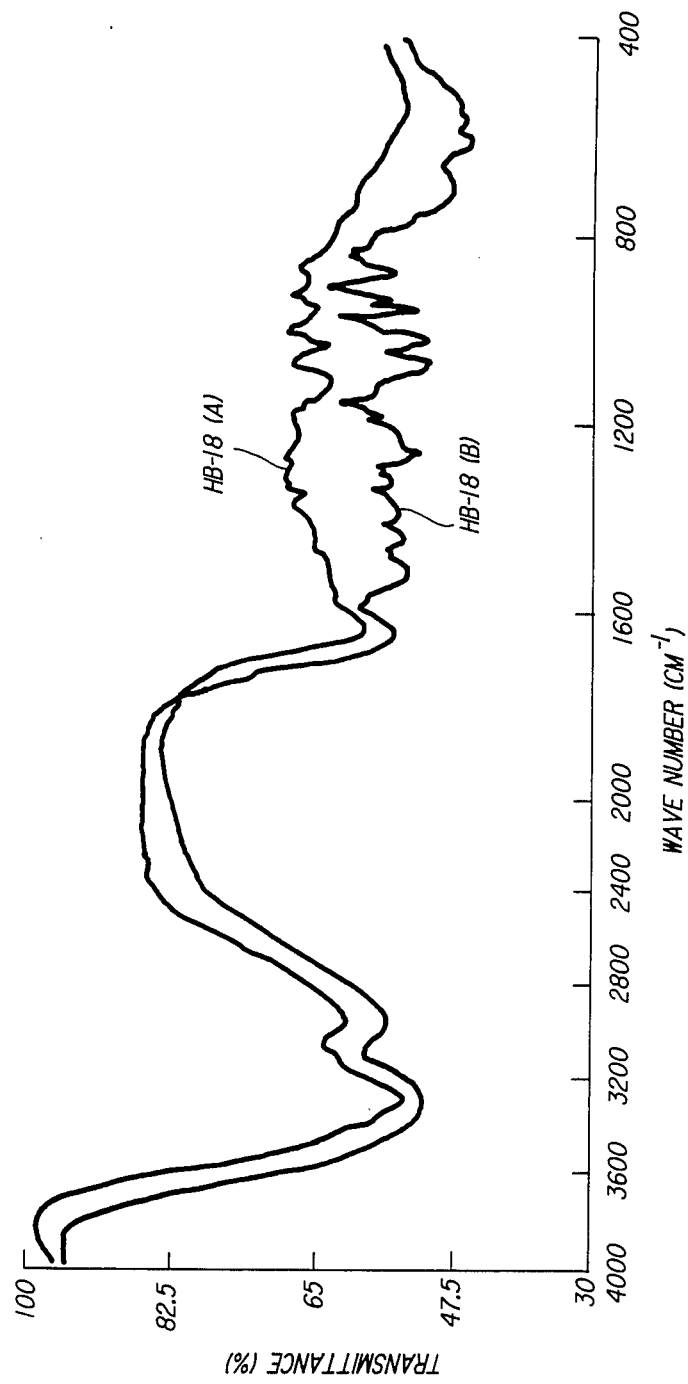
Figure 57:
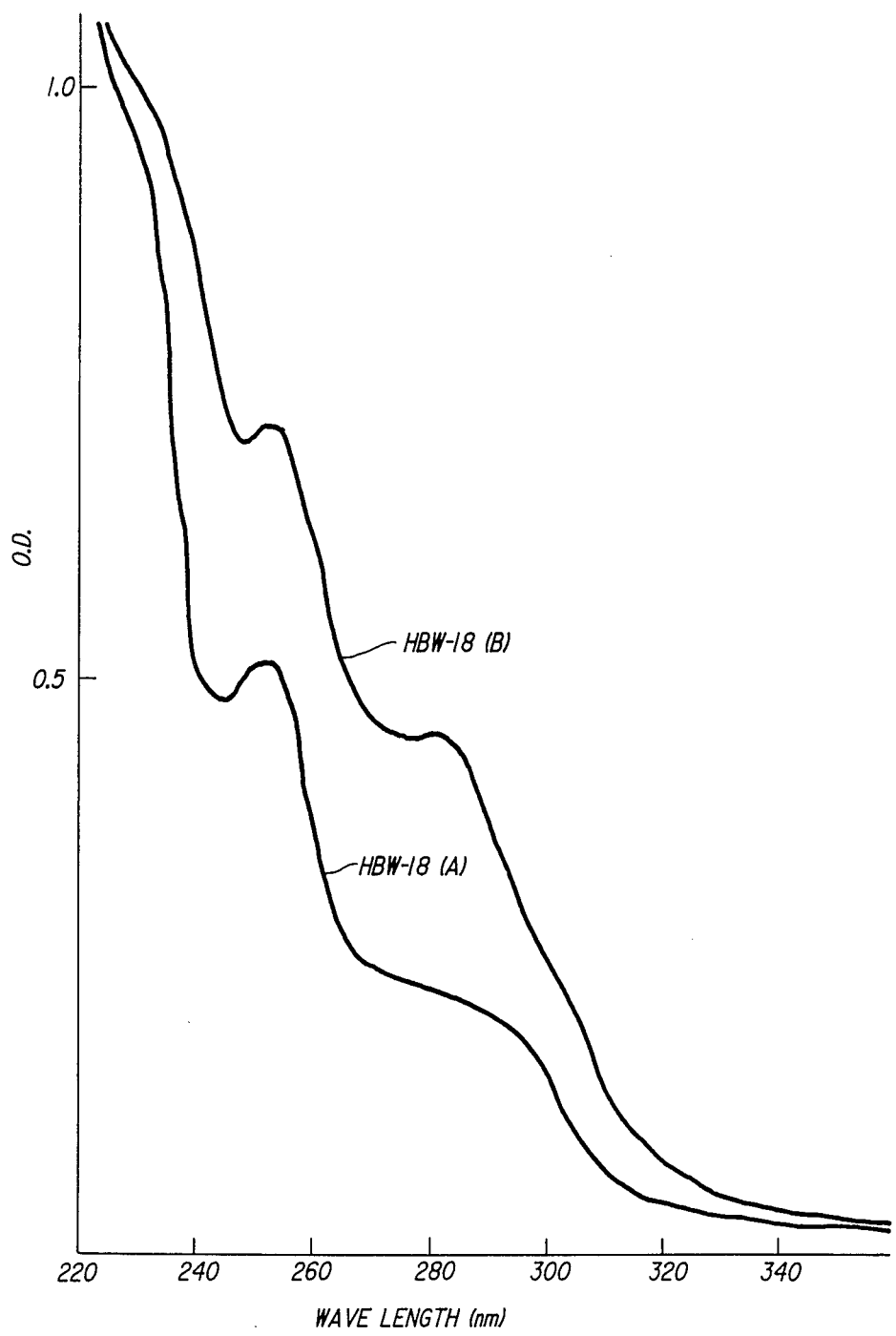
Figure 58:
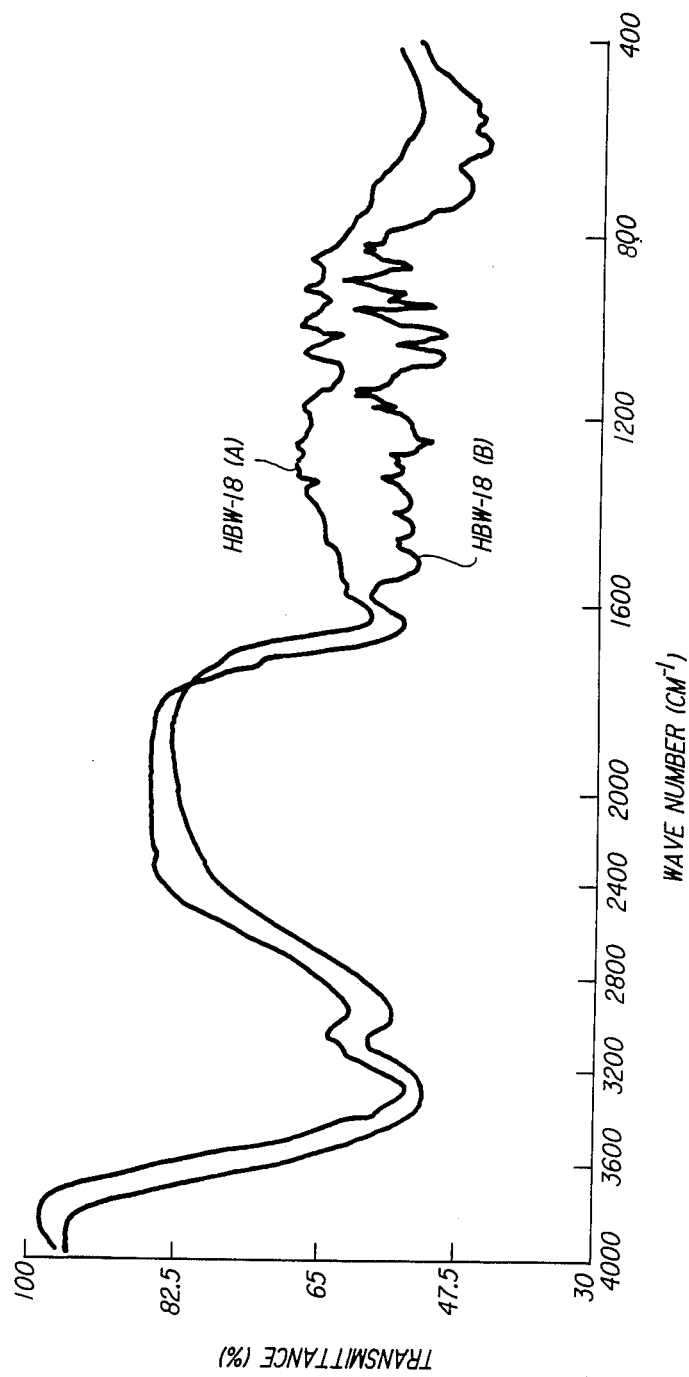
Figure 59:
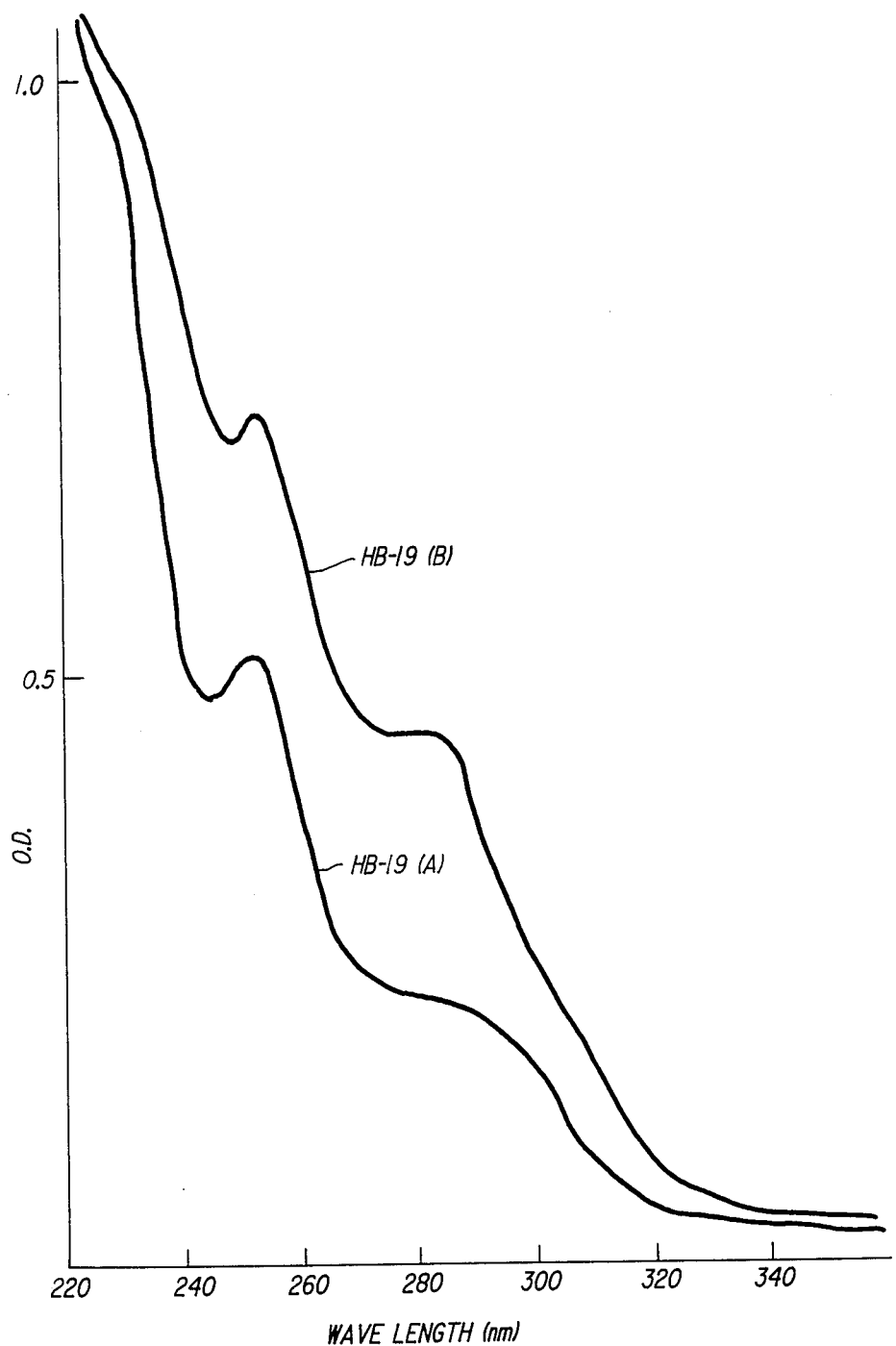
Figure 60:
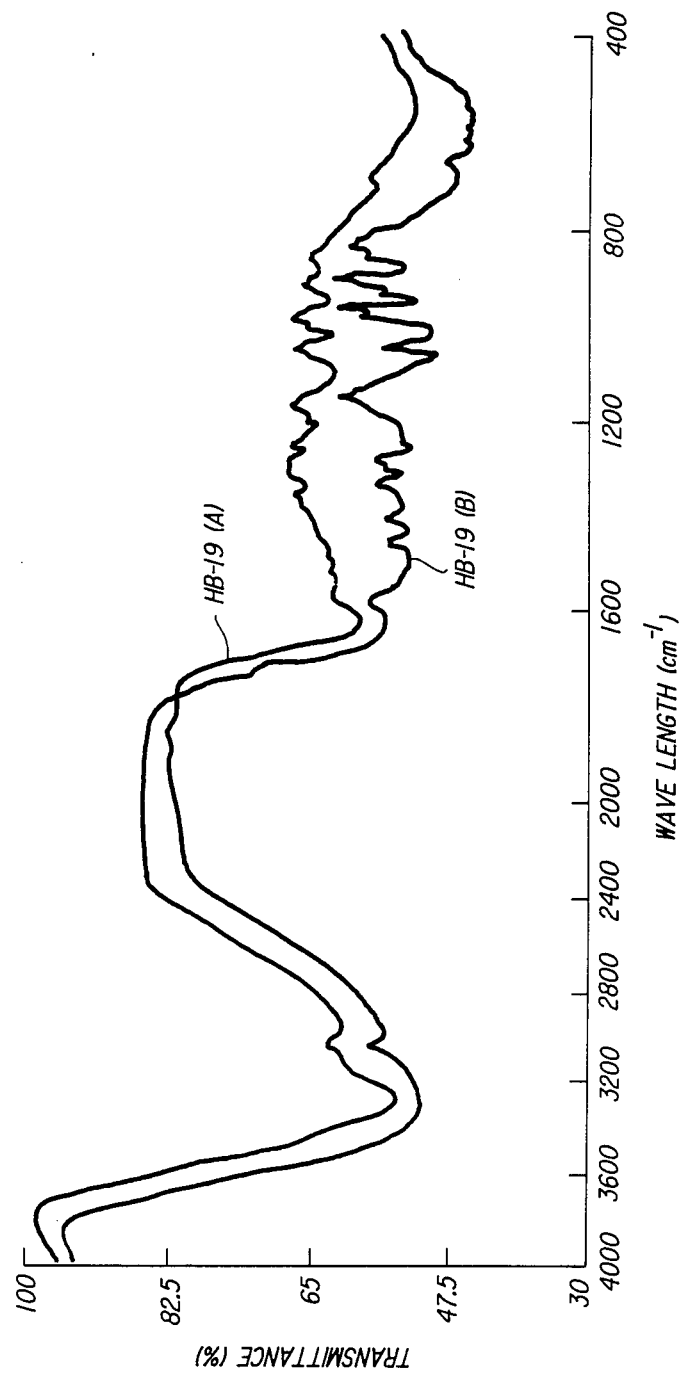
Figure 61:
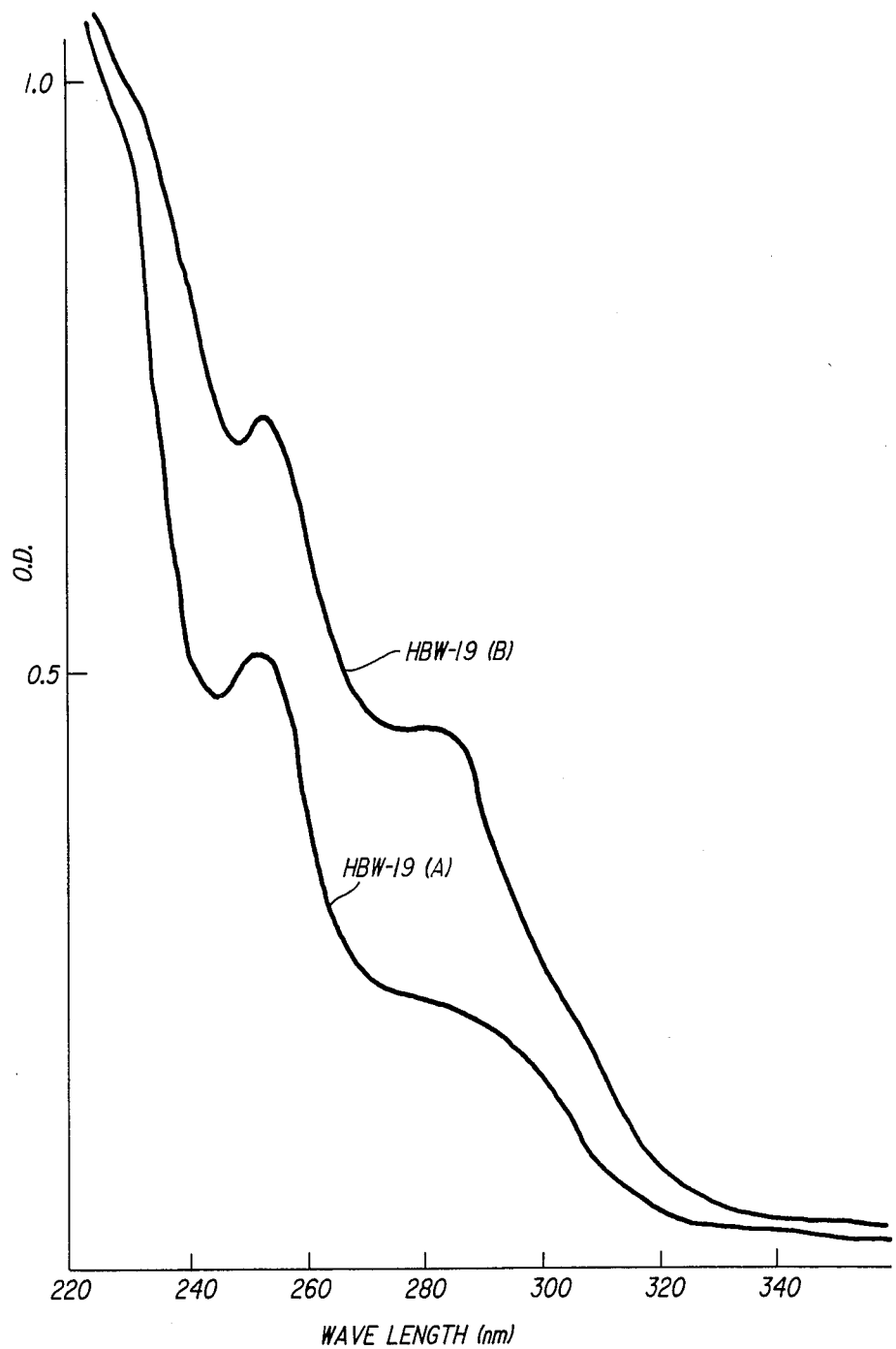
Figure 62:
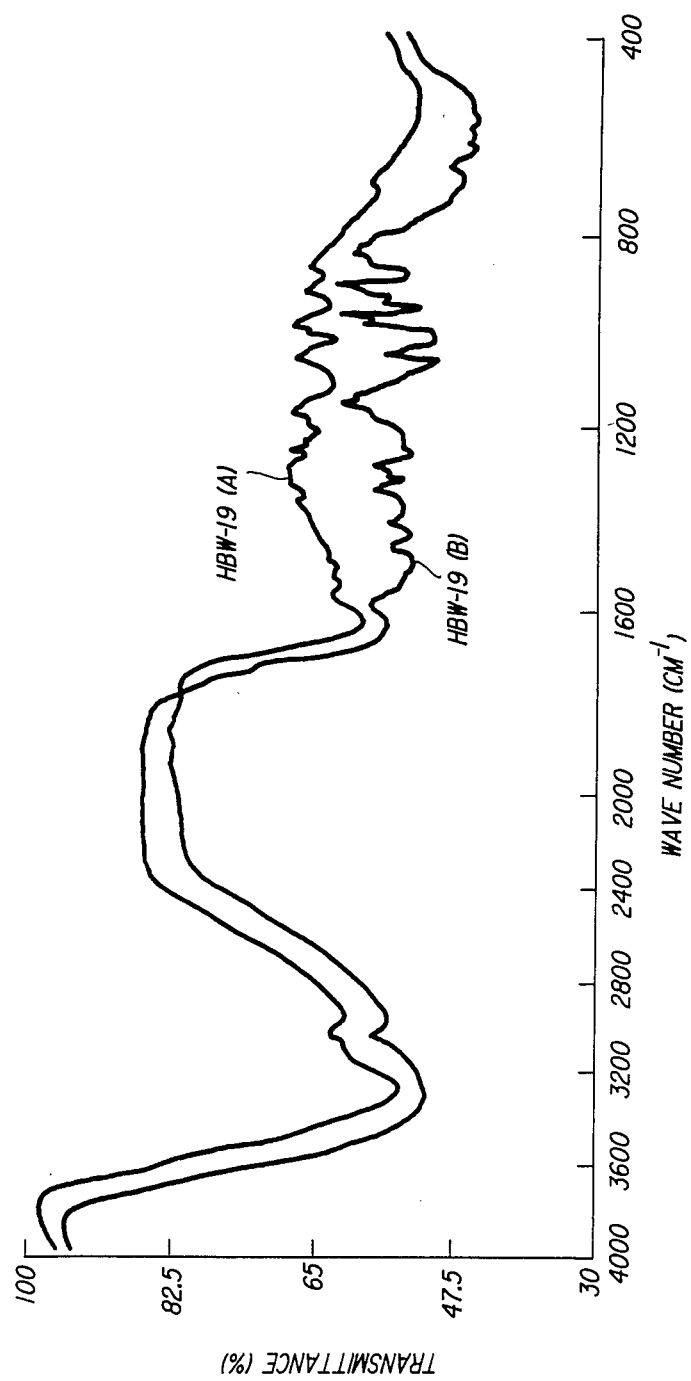
Figure 63:
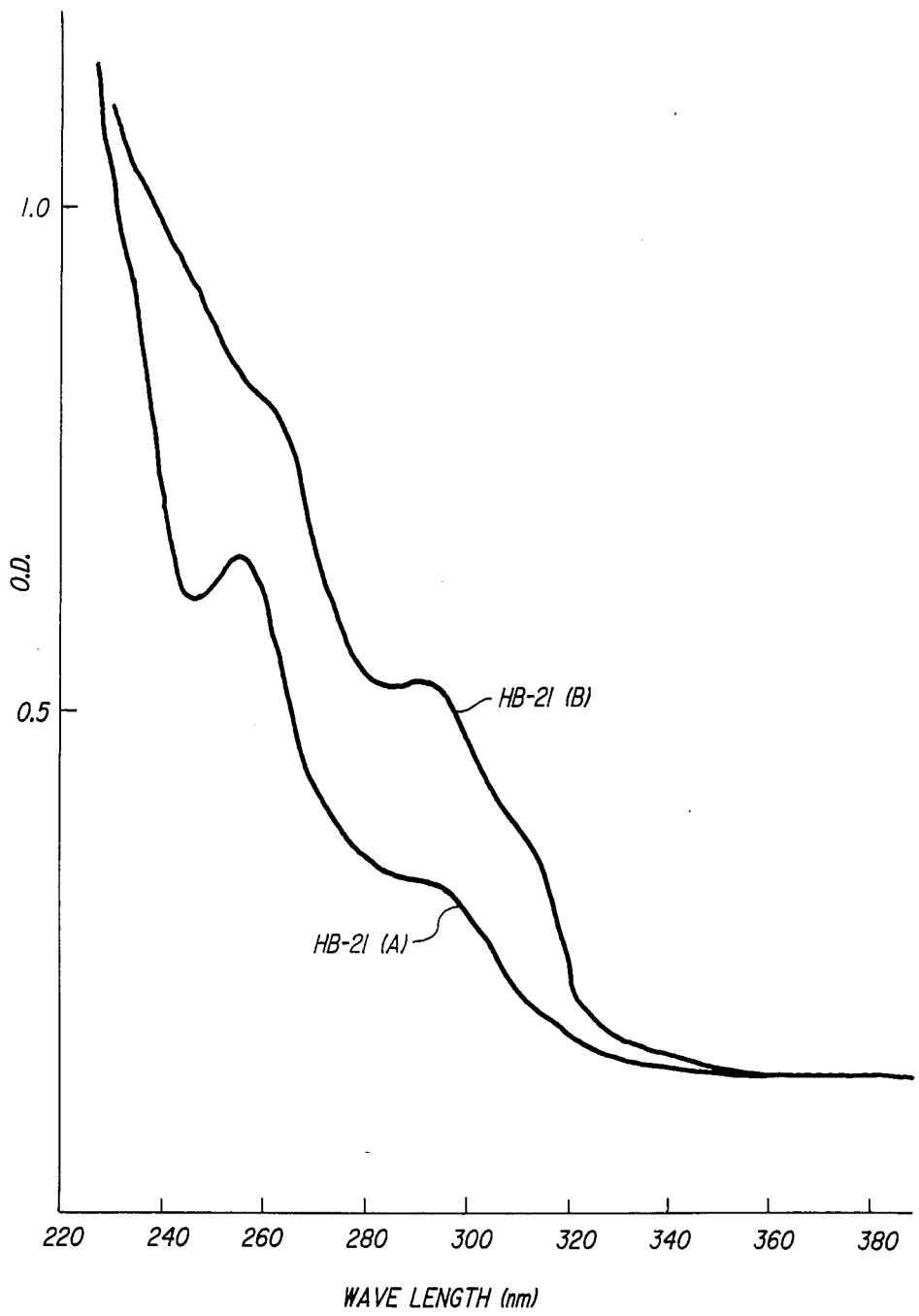
Figure 64:
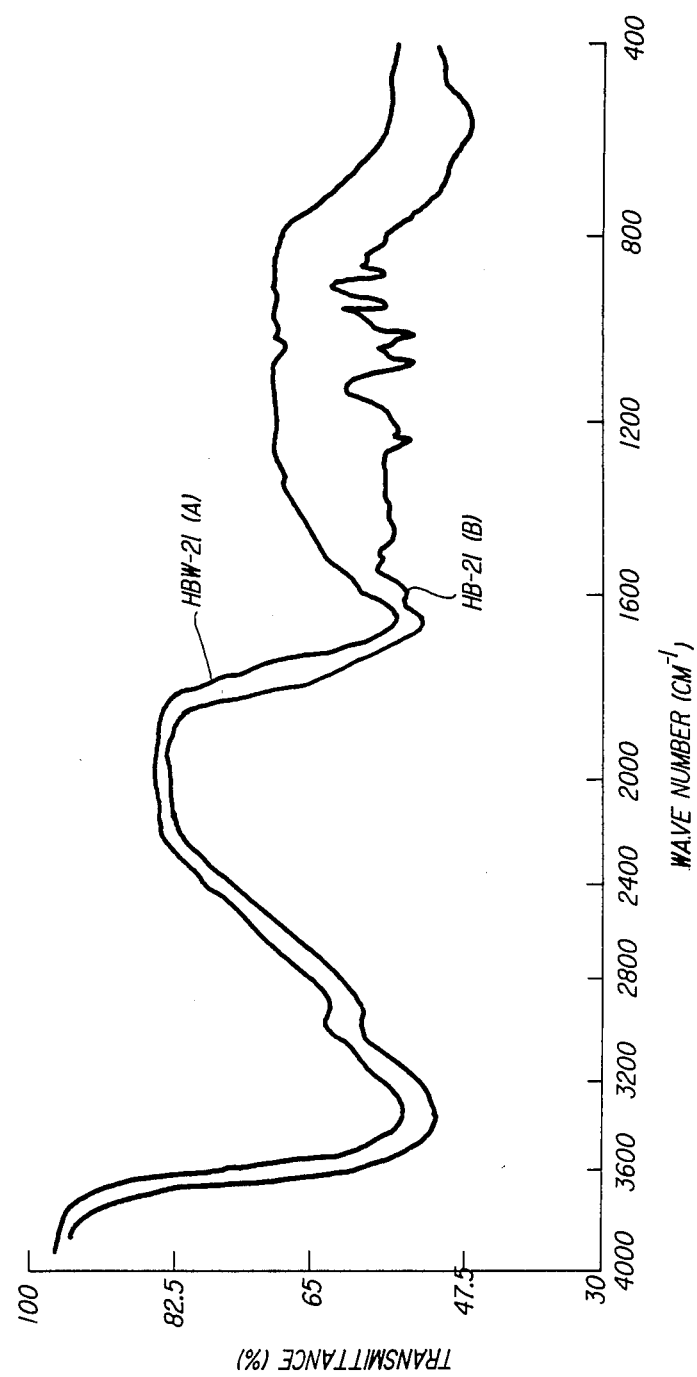
Figure 65:
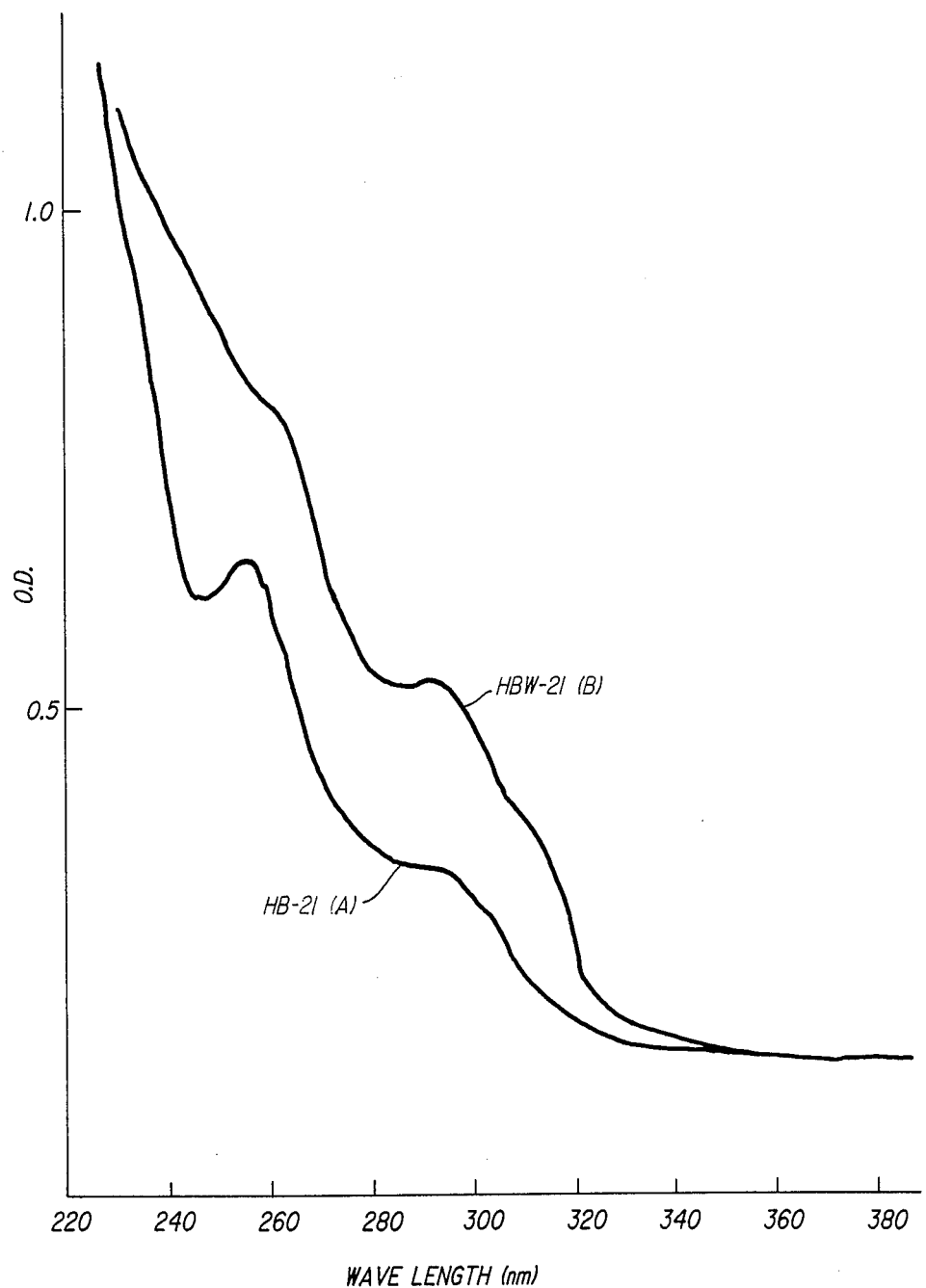
Figure 66:
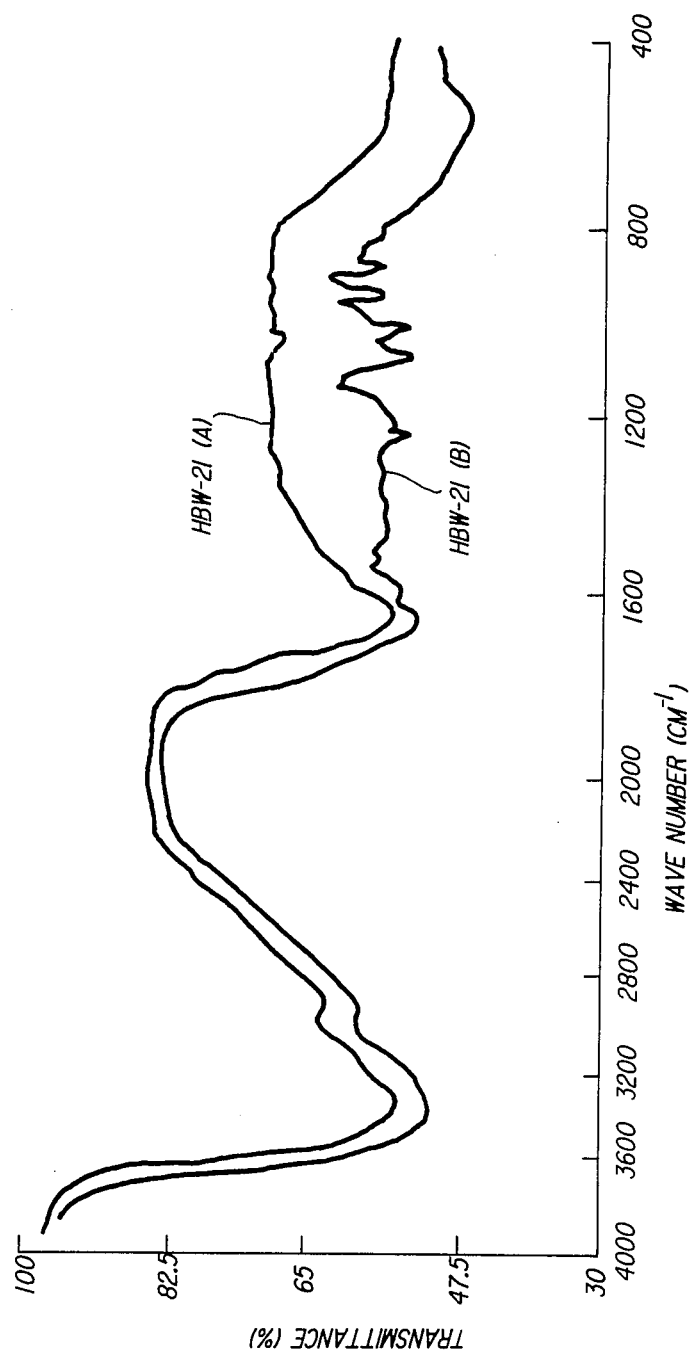

What is claimed is:

1. An anti-tumor composition comprising effective amounts of each of an anthracycline compound and a hydrophilic peptide having a molecular weight in the range of from 10,000-15,000, and anthracycline compound and said peptide being bonded by hydrogen bonding or ionic bonding or a combination thereof, and wherein said anthracycline compound is selected from the group consisting of adriamycin, daunomycin, aclacinomycin, γ-rhodomycin Y and cosmomycin A, and said hydrophilic peptide is selected from the group consisting of neocarzinostatin-apoprotein, macromycin-apoprotein, sporamycin-apoprotein, auromycin-apoprotein, AN-7A-apoprotein, AN-7B-apoprotein, AN-7D-apoprotein and AN-3-apoprotein.

2. The anti-tumor composition according to claim 1, wherein the molar ratio of said peptide to said anthracycline compound is in the range of from 0.25-10.

3. The anti-tumor composition according to claim 1, wherein said hydrophilic peptide is AN-7D-apoprotein and said anthracycline compound is adriamycin.

4. The anti-tumor composition according to claim 1, wherein said hydrophilic peptide is NCS-apoprotein and said anthracycline compound is daunomycin.

5. The anti-tumor composition according to claim 1, wherein aid hydrophilic peptide is AN-7D-apoprotein and said anthracycline compound is aclacinomycin.

6. The anti-tumor composition according to claim 1, wherein said hydrophilic peptide is AN-3-apoprotein and said anthracycline compound is adriamycin.

7. The anti-tumor composition according to claim 1, wherein said hydrophilic peptide is AN-3-apoprotein and said anthracycline compound is daunomycin.

8. The anti-tumor composition according to claim 1, wherein said hydrophilic peptide is AN-3-apoprotein and said anthracycline compound is aclacinomycin.

9. The anti-tumor composition according to claim 1, wherein said hydrophilic peptide is NCS-apoprotein and said anthracycline compound is adriamycin.

10. The anti-tumor composition according to claim 1, wherein said hydrophilic peptide is AN-7D-apoprotein and said anthracycline compound is daunomycin.

11. The anti-tumor composition according to claim 1, wherein said hydrophilic peptide is AN-7D-apoprotein and said anthracycline compound is γ-rhodomycin Y.

12. The anti-tumor composition according to claim 1, wherein said hydrophilic peptide is NCS-apoprotein and said anthracycline compound is γ-rhodomycin Y.

13. The anti-tumor composition according to claim 1, wherein said hydrophilic peptide is AN-3-apoprotein and said anthracycline compound is γ-rhodomycin Y.

14. The anti-tumor composition according to claim 1, wherein said hydrophilic peptide is AN-7D-apoprotein and said anthracycline compound is cosmomycin A.

15. The anti-tumor composition according to claim 1, wherein said hydrophilic peptide is NCS-apoprotein and said anthracycline compound is cosmomycin A.

16. The anti-tumor composition according to claim 1, wherein said hydrophilic peptide is AN-3-apoprotein and said anthracycline compound is cosmomycin A.

17. The anti-tumor composition according to claim 1, wherein said hydrophilic peptide is NCS-apoprotein and said anthracycline compound is aclacinomycin.

* * * * *